United States Patent
Wang et al.

(10) Patent No.: US 9,216,182 B2
(45) Date of Patent: Dec. 22, 2015

(54) CARBAMATE/UREA DERIVATIVES CONTAINING PIPERIDIN AND PIPERAZIN RINGS AS H3 RECEPTOR INHIBITORS

(71) Applicants: Tie-Lin Wang, San Diego, CA (US); Xuechun Zhang, Guilford, CT (US)

(72) Inventors: Tie-Lin Wang, San Diego, CA (US); Xuechun Zhang, Guilford, CT (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/350,159

(22) PCT Filed: Oct. 8, 2012

(86) PCT No.: PCT/IB2012/055424
§ 371 (c)(1),
(2) Date: Apr. 7, 2014

(87) PCT Pub. No.: WO2013/050987
PCT Pub. Date: Apr. 11, 2013

(65) Prior Publication Data
US 2014/0235609 A1  Aug. 21, 2014

(30) Foreign Application Priority Data

Oct. 8, 2011 (WO) ............... PCT/CN2011/080529
Sep. 13, 2012 (WO) ............... PCT/CN2012/081326

(51) Int. Cl.
| | | |
|---|---|---|
| A61K 31/55 | (2006.01) | |
| A61K 31/497 | (2006.01) | |
| C07D 401/14 | (2006.01) | |
| C07D 401/04 | (2006.01) | |
| C07D 417/04 | (2006.01) | |
| A61K 31/496 | (2006.01) | |
| C07D 211/94 | (2006.01) | |
| C07D 471/04 | (2006.01) | |
| A61K 31/501 | (2006.01) | |
| C07D 417/14 | (2006.01) | |
| C07D 487/04 | (2006.01) | |
| C07D 211/46 | (2006.01) | |

(52) U.S. Cl.
CPC ............... *A61K 31/55* (2013.01); *A61K 31/496* (2013.01); *A61K 31/497* (2013.01); *A61K 31/501* (2013.01); *C07D 211/46* (2013.01); *C07D 211/94* (2013.01); *C07D 401/04* (2013.01); *C07D 401/14* (2013.01); *C07D 417/04* (2013.01); *C07D 417/14* (2013.01); *C07D 471/04* (2013.01); *C07D 487/04* (2013.01)

(58) Field of Classification Search
USPC ............ 514/210.2, 217.04, 252.02, 252.11, 514/253.04, 253.09, 253.1, 253.11, 253.12; 540/597; 544/238, 357, 360, 362, 364
See application file for complete search history.

(56) References Cited

U.S. PATENT DOCUMENTS

| 4,613,603 A | 9/1986 | Biziere et al. |
| 5,124,457 A | 6/1992 | Ungemach et al. |

FOREIGN PATENT DOCUMENTS

| EP | 0169139 A1 | 1/1986 |
| EP | 0614664 A1 | 9/1994 |
| EP | 1970373 A1 | 9/2008 |
| EP | 2527340 A1 | 11/2012 |
| WO | 02072570 A2 | 9/2002 |
| WO | 2004101546 A1 | 11/2004 |
| WO | 2006014136 A2 | 2/2006 |
| WO | 2007016496 A2 | 2/2007 |
| WO | 2007052124 A1 | 5/2007 |
| WO | 2011090062 A1 | 7/2011 |
| WO | 2014013469 A1 | 1/2014 |

OTHER PUBLICATIONS

Barrett et al. Novel,potent P2-P3 pyrrolidine derivatives of ketoamide-based cathepsin K inhibitors. Bioorg Med Chem Lett. Mar. 15, 2006;16(6):1735-9.
Database Registry (Online), Chemical Abstracts Service, Columbus, Ohio, US; Database Accession No. 1317671-39-8. Aug. 15, 2011.
Lazewska, et al. Recent advances in histamine H3 receptor antagonists/inverse agonists. Expert Opin Ther Pat. Sep. 2010;20(9):1147-69.
U.S. Appl. No. 13/944,354, filed Jul. 17, 2013, Auberson et al.
Raddatz, et al. Histamine H3 antagonists for treatment of cognitive deficits in CNS diseases. Curr Top Med Chem. 2010;10(2):153-69.
Compounds with CAS Nos. 939978-99-1, 923933-39-5, 923933-35-1, 1299614-29-1, 1281079-81-9, 1280811-06-4 and 1278753-90-4.

*Primary Examiner* — Kristin Vajda
(74) *Attorney, Agent, or Firm* — Shawn D. Britt

(57) ABSTRACT

The invention relates to compound of the formula I (I) or a salt thereof, wherein the substituents are as defined in the specification; to its preparation and to medicaments comprising it for treating diseases connected to the inhibition of H3 receptor.

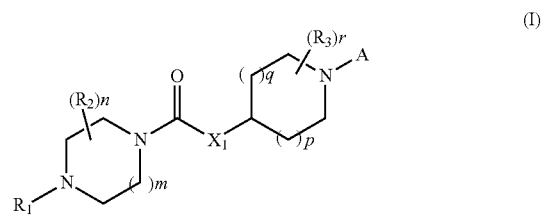

15 Claims, No Drawings

CARBAMATE/UREA DERIVATIVES CONTAINING PIPERIDIN AND PIPERAZIN RINGS AS H3 RECEPTOR INHIBITORS

The invention relates to carbamate/urea derivatives, to their preparation, to their use as medicaments and to medicaments comprising them.

Histamine is a multifunctional chemical transmitter that signals through specific cell surface G-protein-coupled receptors (GPCRs). To date, four histamine receptors subtypes have been identified: H1, H2, H3 and H4. The H3 receptor is a presynaptic GPCR that is found predominantly in the central nervous system, although lower levels are also found in the peripheral nervous system. Genes encoding the H3 receptor have been reported in various organisms, including humans, and alternative splicing of this gene appears to result in multiple isoforms. The H3 receptor is an auto- and heteroreceptor whose activation leads to a decreased release of neurotransmitters (including histamine, acetylcholine, norepinephrine, dopamine and glutamate) from neurons in the brain, and is involved in the regulation of processes such as sleep and wakefulness, feeding and memory. In certain systems, the H3 receptor may be constitutively active.

Antagonists of H3 receptor increase release of cerebral histamine and other neurotransmitters, which in turn induces an extended wakefulness, an improvement in cognitive processes, a reduction in food intake and a normalization of vestibular reflexes. H3 receptor antagonists are described e.g. in Lazewska and Kiec-Kononowicz, Expert Opin Ther Patents, 2010, 20(9), 1147-1169; Raddatz et al, Current Topics in Medicinal Chemistry, 2010, 10, 153-169; WO2007052124; WO2007016496 and WO2004101546.

As histamine pathways have been implicated in a wide range of disorders, in particular disorders of sleep and wakefulness with excessive daytime sleepiness, e.g. narcolepsy, H3 receptor antagonists are considered to be useful for pharmacotherapy of said disorders.

There is a need to provide new H3 receptor antagonists that are good drug candidates. In particular, preferred compounds should bind potently to H3 receptors whilst showing little affinity for other receptors, e.g. receptors mediating significant side-effects, such as hERG channels which may induce cardiovascular side-effects. They should be well absorbed from the gastrointestinal tract, be sufficiently metabolically stable, possess favorable pharmacokinetic properties, sufficient brain uptake, fast onset and sufficiently long duration of action. For e.g. narcolepsy treatment, the pharmacokinetic property of the compound should lead to good wakefulness during daytime, but should equally lead to a minimal impact on night-sleep. The drug candidates should be non-toxic and demonstrate few side-effects. Furthermore, the ideal drug candidate will be able to exist in a physical form that is stable, non-hygroscopic and easily formulated.

The compounds of the invention are H3 receptor antagonists and are therefore potentially useful in the treatment of a wide range of disorders, particularly narcolepsy.

In a first aspect, the invention relates to a compound of the formula I

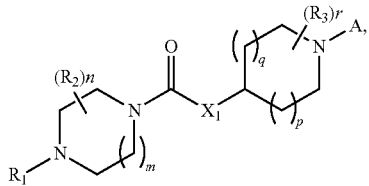

(I)

or a salt thereof, wherein $R_1$ is $C_{1-6}$alkyl, $C_{2-6}$alkenyl, $C_{2-6}$alkinyl, $C_{3-6}$cycloalkyl, $C_{5-6}$cycloalkenyl or $C_{3-6}$cycloalkyl-$C_{1-4}$alkyl; wherein said $C_{1-6}$alkyl, $C_{2-6}$alkenyl, $C_{2-6}$alkinyl or $C_{3-6}$cycloalkyl-$C_{1-4}$alkyl may be substituted once or more than once by halogen, hydroxyl or $C_{1-4}$alkoxy; and wherein said $C_{3-6}$cycloalkyl or $C_{5-6}$cycloalkenyl may be substituted once or more than once by halogen, hydroxyl, $C_{1-4}$alkyl, $C_{1-4}$halogenalkyl, $C_{1-4}$hydroxyalkyl or $C_{1-4}$alkoxy;

m is 1 or 2;

n is 0, 1, 2, 3 or 4;

each $R_2$ independently is halogen, hydroxyl, amino, cyano, nitro, $C_{1-6}$alkyl, $C_{1-6}$halogenalkyl, $C_{1-6}$hydroxyalkyl, $C_{1-4}$alkoxy-$C_{1-6}$alkyl, amino-$C_{1-6}$alkyl, $C_{1-4}$alkyl-amino-$C_{1-6}$lkyl, di($C_{1-4}$alkyl)-amino-$C_{1-6}$alkyl, $C_{1-6}$alkoxy, $C_{1-6}$halogenalkoxy, $C_{1-4}$alkylamino, di($C_{1-6}$alkyl)amino, $C_{2-6}$alkenyl, $C_{2-6}$halogenalkenyl, $C_{2-6}$alkinyl or $C_{2-6}$halogenalkinyl; or $C_{3-6}$cycloalkyl, wherein one carbon atom may be replaced by an oxygen atom, wherein the $C_{3-6}$cycloalkyl may be attached directly to the methylene or via a $C_{1-2}$alkylene, and wherein the $C_{3-6}$cycloalkyl may be substituted once or more than once by halogen;

or two $R_2$ at the same carbon atom form together with said carbon atom a $C_{3-6}$cycloalkyl;

$X_1$ is oxygen or —N($R_4$)—;

$R_4$ is hydrogen, $C_{1-6}$alkyl, $C_{3-6}$cycloalkyl, or $C_{3-6}$cycloalkyl-$C_{1-2}$alkyl;

p is 1 and q is 1;

p is 0 and q is 1; or p is 0 and q is 0;

r is 0, 1, 2, 3 or 4;

each $R_3$ independently is halogen, hydroxyl, amino, cyano, nitro, $C_{1-6}$alkyl, $C_{1-6}$halogenalkyl, $C_{1-6}$hydroxyalkyl, $C_{1-4}$alkoxy-$C_{1-6}$alkyl, amino-$C_{1-6}$alkyl, $C_{1-4}$alkyl-amino-$C_{1-6}$ alkyl, di($C_{1-4}$alkyl)-amino-$C_{1-6}$alkyl, $C_{1-6}$alkoxy, $C_{1-6}$halogenalkoxy, $C_{1-6}$alkylamino, di($C_{1-6}$alkyl)amino, $C_{2-6}$alkenyl, $C_{2-6}$halogenalkenyl, $C_{2-6}$alkinyl or $C_{2-6}$halogenalkinyl;

or $C_{3-6}$cycloalkyl, wherein one carbon atom may be replaced by an oxygen atom, wherein the $C_{3-6}$cycloalkyl may be attached directly to the methylene or via a $C_{1-2}$alkylene, and wherein the $C_{3-6}$cycloalkyl may be substituted once or more than once by halogen;

or two $R_3$ at the same carbon atom form together with said carbon atom a $C_{3-6}$cycloalkyl;

A is a five- to six-membered monocyclic or an eight- to ten-membered fused bicyclic aromatic ring system, wherein said ring system may contain from 1 to 4 hetero atoms selected from nitrogen, oxygen and sulfur, and wherein said ring system may be substituted once or more than once by $R_5$;

each $R_5$ independently is halogen; cyano; nitro; hydroxy; amino; —C(O)H; —C(O)NH$_2$; —C(O)OH; —X$_2$—R$_6$; or —X$_3$—B$_1$;

$X_2$ is selected from bond; carbonyl; oxygen; sulfur; —S(O)—; —S(O)$_2$—; amino, which may be substituted by $C_{1-4}$alkyl; —N($R_a$)—C(O)—; —C(O)—N($R_b$)—; —C(O)—O—; —O—C(O)—; —N($R_c$)—S(O)$_2$—; —S(O)$_2$—N($R_d$)—; and —NHC(O)NH—;

$R_a$, $R_b$, $R_c$ and $R_d$ each independently is hydrogen or $C_{1-4}$alkyl;

$R_6$ is $C_{1-6}$alkyl; $C_{1-6}$halogenalkyl; $C_{1-6}$-cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-4}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$ alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{2-6}$alkinyl; $C_{2-6}$halogenalkinyl;

$X_3$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; N($R_e$)—C(O)—; —C(O)—N($R_f$)—; —C(O)—O—; —O—C(O)—; —N($R_g$)—S(O)$_2$—; —S(O)$_2$—N($R_h$)—; and —NHC(O)NH—;

$R_e$, $R_f$, $R_g$ and $R_h$ each independently is hydrogen or $C_{1-4}$alkyl;

$B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_7$;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo;

or two $R_5$ at adjacent ring atoms form together with said ring atoms a fused five- to seven-membered monocyclic unsaturated non-aromatic ring system which may contain from 1 to 4 hetero atoms selected from nitrogen, oxygen and sulfur, wherein the ring system may in turn be substituted once or more than once by $R_6$, and wherein each $R_8$ independently is halogen, $C_{1-4}$alkyl or $C_{1-4}$alkoxy, or two $R_8$ at the same ring atom together are oxo; and provided that the compounds N-[(3R)-1-[7-[[(2,4-dichlorophenyl)methyl]amino]pyrazolo[1,5-a]pyrimidin-5-yl]-3-pyrrolidinyl]-4-methyl-1-piperazinecarboxamide;

4-cyclopentyl-N-[1-[5-(trifluoromethyl)-2-pyridinyl]-3-azetidinyl]-1-piperazinecarboxamide;

4-cyclopentyl-N-[1-[5-(trifluoromethyl)-2-pyridinyl]-3-pyrrolidinyl]-1-piperazinecarboxamide;

4-(1,1-dimethylethyl)hexahydro-N-[1-(2-pyrimidinyl)-4-piperidinyl]-1H-1,4-diazepine-1-carboxamide;

4-ethyl-N-[1-(2-pyrimidinyl)-4-piperidinyl]-1-piperazinecarboxamide;

hexahydro-4-methyl-N-[1-(2-pyrimidinyl)-4-piperidinyl]-1H-1,4-diazepine-1-carboxamide;

4-(2,2-difluoroethyl)-N-[1-(2-pyrimidinyl)-4-piperidinyl]-1-piperazinecarboxamide;

N-(1-(4-acetylphenyl)piperidin-4-yl)-4-cyclo pentylpiperazine-1-carboxamide; and N-(1-(4-acetylphenyl)piperidin-4-yl)-4-cyclobutylpiperazine-1-carboxamide are excluded.

Unless specified otherwise, the term "compounds of the invention" refers to compounds of formula (I) and subformulae thereof (e.g. compounds of formula (I-1)); prodrugs thereof; salts of the compounds and/or prodrugs; hydrates or solvates of the compounds, salts and/or prodrugs; as well as all stereoisomers (including diastereoisomers and enantiomers), tautomers and isotopically labeled compounds (including deuterium substitutions); as well as inherently formed moieties (e.g. polymorphs, solvates and/or hydrates).

Unless indicated otherwise, the expressions used in this invention have the following meaning:

"Alkyl" represents a straight-chain or branched-chain alkyl group and, for example, may be methyl, ethyl, n- or iso-propyl, n-, iso-, sec- or tert-butyl, n-pentyl, n-hexyl; $C_{1-6}$alkyl preferably represents a straight-chain or branched-chain $C_{1-4}$alkyl with particular preference given to methyl, ethyl, n-propyl, iso-propyl and tert-butyl.

Each alkyl part of "alkoxy", "halogenalkyl" and so on shall have the same meaning as described in the above-mentioned definition of "alkyl", especially regarding linearity and preferential size.

"$C_{3-6}$cycloalkyl" represents a saturated alicyclic moiety having from three to six carbon atoms. This term refers to groups such as cyclopropyl, cyclobutyl, cyclopentyl and cyclohexyl.

A substituent being substituted "once or more than once", e.g. as defined for A, is preferably substituted by one to three substituents.

Halogen is generally fluorine, chlorine, bromine or iodine; preferably fluorine, chlorine or bromine. Halogenalkyl groups preferably have a chain length of 1 to 4 carbon atoms and are, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,2-trichloroethyl, 1,1,2,2-tetrafluoroethyl, 2,2,3,3-tetrafluoropropyl, 2,2,3,3,3-pentafluoropropyl or 2,2,3,4,4,4-hexafluorobutyl.

In the context of the invention, the definition of A as a "five- to six-membered monocyclic aromatic ring system which may contain from 1 to 4 hetero atoms" encompasses phenyl or a five- to six-membered monocyclic heterocyclic aromatic ring system.

In the context of the invention, the definition of A as an "eight- to ten-membered fused bicyclic aromatic ring system which may contain from 1 to 4 heteroatoms" encompasses naphthyl or an eight- to ten-membered heterocyclic aromatic ring system.

In the context of the invention, the definition of $B_1$ as a "three- to seven-membered monocyclic ring system which may be aromatic, saturated or unsaturated non-aromatic and which may contain from 1 to 4 hetero atoms" encompasses three- to seven-membered monocyclic aromatic or non-aromatic hydrocarbon groups and aromatic or non-aromatic heterocyclic ring systems of the same sizes.

In the context of the invention, the definition of two $R_5$ as a "fused five- to seven-membered monocyclic unsaturated non-aromatic ring system which may contain from 1 to 4 hetero atoms" encompasses a five- to seven-membered monocyclic unsaturated non-aromatic hydrocarbon group or a five- to seven-membered monocyclic heterocyclic unsaturated non-aromatic ring system. All said groups/ring systems comprise at least one double-bond, which is shared with the aromatic ring system A they are fused to.

Examples of heterocyclic ring systems are: pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, oxadiazole, dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, isothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pteridine.

Compounds of formula I may exist in optically active form or in form of mixtures of optical isomers, e.g. in form of racemic mixtures or diastereomeric mixtures. In particular, asymmetrical carbon atom(s) may be present in the compounds of formula I and their salts. Unless otherwise provided herein, all optical isomers and their mixtures, including the racemic mixtures, are embraced by the invention.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. The compounds described herein may contain one or more asymmetric centers and may thus give rise to enantiomers, diastereomers, and other stereoisomeric forms that may be defined, in terms of absolute stereochemistry, as (R)- or (S)-. Unless otherwise provided herein, the invention is meant to include all such possible isomers, including racemic mixtures, optically pure forms and intermediate mixtures. Optically active (R)- and (S)-isomers may be prepared using chiral synthons or chiral reagents, or resolved using conventional techniques.

If the compound contains a double bond, the substituent may be E or Z configuration.

If the compound contains a disubstituted cycloalkyl, the cycloalkyl substituent may have a cis- or trans-configuration.

Any asymmetric atom (e.g. carbon or the like) of the compound(s) of the invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein, a compound of the invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Depending on substituent definition, compounds of formula I may occur in various tautomeric forms. All tautomeric forms of the compounds of formula I are embraced by the invention.

As used herein, the terms "salt" or "salts" refers to an acid addition or base addition salt of a respective compound, e.g. a compound of the invention or of a compound of formula II-1. "Salts" include in particular "pharmaceutically acceptable salts". The term "pharmaceutically acceptable salts" refers to salts that retain the biological effectiveness and properties of the compounds of this invention and, which typically are not biologically or otherwise undesirable. The compounds of the invention may be capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

When both a basic group and an acid group are present in the same molecule, the compounds of the invention may also form internal salts, e.g., zwitterionic molecules.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}$H, $^{3}$H, $^{11}$C, $^{13}$C, $^{14}$C, $^{15}$N, $^{18}$F $^{31}$P, $^{32}$P, $^{35}$S, $^{36}$Cl, $^{125}$I respectively. The invention includes various isotopically labeled compounds as defined herein, for example those into which radioactive isotopes, such as $^{3}$H and $^{14}$C, or those into which non-radioactive isotopes, such as $^{2}$H and $^{13}$C are present. Such isotopically labelled compounds are useful in metabolic studies (with $^{14}$C), reaction kinetic studies (with, for example $^{2}$H or $^{3}$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Further, substitution with heavier isotopes, particularly deuterium (i.e., $^{2}$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d_6$-acetone, $d_6$-DMSO.

Compounds of the invention that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula I with the co-crystal former under crystallization conditions and isolating co-crystals thereby formed. Suitable co-crystal formers include those described in WO 2004/078163. Hence the invention further provides co-crystals comprising a compound of formula (I).

The invention also provides pro-drugs of the compounds of the invention that convert in vivo to the compounds of the invention. A pro-drug is an active or inactive compound that is modified chemically through in vivo physiological action, such as hydrolysis, metabolism and the like, into a compound of the invention following administration of the prodrug to a subject. The suitability and techniques involved in making and using pro-drugs are well known by those skilled in the art. See The Practice of Medicinal Chemistry, Ch. 31-32 (Ed. Wermuth, Academic Press, San Diego, Calif., 2001).

Furthermore, the compounds of the invention, including their salts, can also be obtained in the form of their hydrates, or include other solvents used for their crystallization. The compounds of the invention may inherently or by design form solvates with pharmaceutically acceptable solvents (including water); therefore, it is intended that the invention embrace both solvated and unsolvated forms. The term "solvate" refers to a molecular complex of a compound of the invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water. The compounds of the invention, including salts, hydrates and solvates thereof, may inherently or by design form polymorphs.

Preferred substituents, preferred ranges of numerical values or preferred ranges of the radicals present in compounds of the formula I and the corresponding intermediate compounds are defined below. The definition of the substituents applies to the end-products as well as to the corresponding intermediates. The definitions of the substituents may be combined at will, e.g. preferred substituents A and particularly preferred substituents $R_1$.

In one embodiment, the invention provides a compound of formula I, wherein $R_1$ is $C_{1-6}$alkyl, $C_{2-6}$alkenyl, $C_{2-6}$alkinyl, $C_{3-6}$cycloalkyl, $C_{5-6}$cycloalkenyl or $C_{3-6}$cycloalkyl-$C_{1-4}$alkyl; wherein said $C_{1-6}$alkyl, $C_{2-6}$alkenyl, $C_{2-6}$alkinyl or $C_{3-6}$cycloalkyl-$C_{1-4}$ alkyl may be substituted once or more than once by halogen; and wherein said $C_{3-6}$cycloalkyl or $C_{5-6}$cycloalkenyl may be substituted once or more than once by halogen, $C_{1-4}$alkyl or $C_{1-4}$halogenalkyl;

m is 1 or 2;

n is 0, 1, 2, 3 or 4;

each $R_2$ independently is halogen, hydroxyl, amino, cyano, nitro, $C_{1-6}$alkyl, $C_{1-6}$halogenalkyl, $C_{1-6}$hydroxyalkyl, $C_{1-4}$alkoxy-$C_{1-6}$alkyl, amino-$C_{1-6}$alkyl, $C_{1-4}$alkyl-amino-$C_{1-6}$ alkyl, di($C_{1-4}$alkyl)-amino-$C_{1-6}$alkyl, $C_{1-6}$alkoxy, $C_{1-6}$halogenalkoxy, $C_{1-6}$alkylamino, di($C_{1-6}$alkyl)amino, $C_{2-6}$alkenyl, $C_{2-6}$halogenalkenyl, $C_{2-6}$alkinyl or $C_{2-6}$halogenalkinyl;

or $C_{3-6}$cycloalkyl, wherein one carbon atom may be replaced by an oxygen atom, wherein the $C_{3-6}$cycloalkyl may be attached directly to the methylene or via a $C_{1-2}$alkylene, and wherein the $C_{3-6}$cycloalkyl may be substituted once or more than once by halogen;

or two $R_2$ at the same carbon atom form together with said carbon atom a $C_{3-6}$cycloalkyl;

$X_1$ is oxygen or —$N(R_4)$—;

$R_4$ is hydrogen, $C_{1-6}$alkyl, $C_{3-6}$cycloalkyl, or $C_{3-6}$cycloalkyl-$C_{1-2}$alkyl;

p is 1 and q is 1;

p is 0 and q is 1; or p is 0 and q is 0;

r is 0, 1, 2, 3 or 4;

each $R_3$ independently is halogen, hydroxyl, amino, cyano, nitro, $C_{1-6}$alkyl, $C_{1-6}$halogenalkyl, $C_{1-6}$hydroxyalkyl, $C_{1-4}$alkoxy-$C_{1-6}$alkyl, amino-$C_{1-6}$alkyl, $C_{1-4}$alkyl-amino-$C_{1-6}$ alkyl, di($C_{1-4}$alkyl)-amino-$C_{1-6}$alkyl, $C_{1-6}$alkoxy, $C_{1-6}$halogenalkoxy, $C_{1-6}$alkylamino, di($C_{1-6}$alkyl)amino, $C_{2-6}$alkenyl, $C_{2-6}$halogenalkenyl, $C_{2-6}$alkinyl or $C_{2-6}$halogenalkinyl;

or $C_{3-6}$cycloalkyl, wherein one carbon atom may be replaced by an oxygen atom, wherein the $C_{3-6}$cycloalkyl may be attached directly to the methylene or via a $C_{1-2}$alkylene, and wherein the $C_{3-6}$cycloalkyl may be substituted once or more than once by halogen;

or two $R_3$ at the same carbon atom form together with said carbon atom a $C_{3-6}$cycloalkyl;

A is a five- to six-membered monocyclic or an eight- to ten-membered fused bicyclic aromatic ring system, wherein said ring system may contain from 1 to 4 hetero atoms selected from nitrogen, oxygen and sulfur, and wherein said ring system may be substituted once or more than once by $R_5$;

each $R_5$ independently is halogen; cyano; nitro; hydroxy; amino; —C(O)H; —C(O)NH$_2$; —$X_2$—$R_6$; or —$X_3$—$B_1$;

$X_2$ is selected from bond; carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$R_6$ is $C_{1-6}$alkyl; $C_{1-6}$halogenalkyl; $C_{1-6}$-cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$ alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl;

$C_{2-6}$alkenyl; $C_{2-6}$halogenalkenyl; $C_{1-6}$alkinyl; $C_{2-6}$halogenalkinyl;

$X_3$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; —NH—C(O)—; —C(O)—NH—; —C(O)—O—; —O—C(O)—; —NH—S(O)$_2$—; —S(O)$_2$—NH—; and —NHC(O)NH—;

$B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_7$;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo;

or two $R_5$ at adjacent ring atoms form together with said ring atoms a fused five- to seven-membered monocyclic unsaturated non-aromatic ring system which may contain from 1 to 4 hetero atoms selected from nitrogen, oxygen and sulfur, wherein the ring system may in turn be substituted once or more than once by $R_8$, and wherein each $R_8$ independently is halogen, $C_{1-4}$alkyl or $C_{1-4}$alkoxy, or two $R_8$ at the same ring atom together are oxo;

and provided that the compounds

N-[(3R)-1-[7-[[(2,4-dichlorophenyl)methyl]amino]pyrazolo[1,5-a]pyrimidin-5-yl]-3-pyrrolidinyl]-4-methyl-1-piperazinecarboxamide;

4-cyclopentyl-N-[1-[5-(trifluoromethyl)-2-pyridinyl]-3-azetidinyl]-1-piperazinecarboxamide;

4-cyclopentyl-N-[1-[5-(trifluoromethyl)-2-pyridinyl]-3-pyrrolidinyl]-1-piperazinecarboxamide;

4-(1,1-dimethylethyl)hexahydro-N-[1-(2-pyrimidinyl)-4-piperidinyl]-1H-1,4-diazepine-1-carboxamide;

4-ethyl-N-[1-(2-pyrimidinyl)-4-piperidinyl]-1-piperazinecarboxamide;

hexahydro-4-methyl-N-[1-(2-pyrimidinyl)-4-piperidinyl]-1H-1,4-diazepine-1-carboxamide;

4-(2,2-difluoroethyl)-N-[1-(2-pyrimidinyl)-4-piperidinyl]-1-piperazinecarboxamide;

N-(1-(4-acetylphenyl)piperidin-4-yl)-4-cyclopentylpiperazine-1-carboxamide; and

N-(1-(4-acetylphenyl)piperidin-4-yl)-4-cyclobutylpiperazine-1-carboxamide are excluded.

In one embodiment, the invention provides a compound of formula I, wherein $R_1$ is $C_{1-6}$alkyl, $C_{3-6}$cycloalkyl, $C_{3-6}$cycloalkyl-$C_{1-2}$alkyl.

In one embodiment, the invention provides a compound of formula I, wherein $R_1$ is $C_{3-4}$alkyl or $C_{3-5}$cycloalkyl.

In one embodiment, the invention provides a compound of formula I, wherein $R_1$ is isopropyl, cyclopropyl, cyclobutyl or cyclopentyl.

In one embodiment, the invention provides a compound of formula I, wherein $R_1$ is isopropyl.

In one embodiment, the invention provides a compound of formula I, wherein m is 1.

In one embodiment, the invention provides a compound of formula I, wherein m is 2.

In one embodiment, the invention provides a compound of formula I, wherein n is 0, 1 or 2 and wherein each $R_2$ independently is halogen, $C_{1-6}$alkyl, $C_{1-6}$halogenalkyl, $C_{1-4}$alkoxy-$C_{1-6}$alkyl, $C_{1-6}$alkoxy, $C_{1-6}$halogenalkoxy or $C_{3-6}$cycloalkyl; or two $R_2$ at the same carbon atom form together with said carbon atom a $C_{3-6}$cycloalkyl.

In one embodiment, the invention provides a compound of formula I, wherein n is 0, 1 or 2 and wherein each $R_2$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_2$ at the same carbon atom form together with said carbon atom a $C_{3-4}$cycloalkyl.

In one embodiment, the invention provides a compound of formula I, wherein n is 0.

In one embodiment, the invention provides a compound of formula I, wherein $X_1$ is oxygen.

In one embodiment, the invention provides a compound of formula I, wherein $X_1$ is —$N(R_4)$— and $R_4$ is hydrogen, $C_{1-6}$alkyl, $C_{3-6}$cycloalkyl, or $C_{3-6}$cycloalkyl-$C_{1-2}$alkyl.

In one embodiment, the invention provides a compound of formula I, wherein $X_1$ is —$N(R_4)$— and $R_4$ is hydrogen.

In one embodiment, the invention provides a compound of formula I, wherein p is 1 and q is 1.

In one embodiment, the invention provides a compound of formula I, wherein p is 0 and q is 1.

In one embodiment, the invention provides a compound of formula I, wherein p is 0 and q is 0.

In one embodiment, the invention provides a compound of formula I, wherein r is 0, 1 or 2 and wherein each $R_3$ independently is halogen, $C_{1-6}$alkyl, $C_{1-6}$halogenalkyl, $C_{1-4}$alkoxy-$C_{1-6}$alkyl, $C_{1-6}$alkoxy, $C_{1-6}$halogenalkoxy or $C_{3-6}$cycloalkyl; or two $R_3$ at the same carbon atom form together with said carbon atom a $C_{3-6}$cycloalkyl.

In one embodiment, the invention provides a compound of formula I, wherein r is 0, 1 or 2 and wherein each $R_3$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_3$ at the same carbon atom form together with said carbon atom a $C_{3-4}$cycloalkyl.

In one embodiment, the invention provides a compound of formula I, wherein r is 0.

In one embodiment, the invention provides a compound of formula I, wherein A is a five- to six-membered monocyclic aromatic ring system, wherein said ring system may contain from 1 to 3 hetero atoms selected from nitrogen, oxygen and sulfur, and wherein said ring system may be substituted once or more than once by $R_5$.

In one embodiment, the invention provides a compound of formula I, wherein A is a five- to six-membered monocyclic aromatic ring system, wherein said ring system contains from 1 to 3 hetero atoms selected from nitrogen, oxygen and sulfur, and wherein said ring system may be substituted once or more than once by $R_5$.

In one embodiment, the invention provides a compound of formula I, wherein A is a five-membered monocyclic aromatic ring system, wherein said ring system contains from 1 to 3 hetero atoms selected from nitrogen, oxygen and sulfur, and wherein said ring system may be substituted once or more than once by $R_5$.

In one embodiment, the invention provides a compound of formula I, wherein A is a six-membered monocyclic aromatic ring system, wherein said ring system contains from 1 to 3 nitrogen atoms and wherein said ring system may be substituted once or more than once by $R_5$.

In one embodiment, the invention provides a compound of formula I, wherein A is phenyl, wherein said phenyl may be substituted once or more than once by $R_5$.

In one embodiment, the invention provides a compound of formula I, wherein A is an eight- to ten-membered fused bicyclic aromatic ring system, wherein said ring system may contain from 1 to 4 hetero atoms selected from nitrogen, oxygen and sulfur, and wherein said ring system may be substituted once or more than once by $R_5$.

In one embodiment, the invention provides a compound of formula I, wherein A is an eight- to ten-membered fused bicyclic aromatic ring system, wherein said ring system may contain from 1 to 4 hetero atoms selected from nitrogen, oxygen and sulfur, and wherein said ring system may be substituted once or more than once by $R_5$.

In one embodiment, the invention provides a compound of formula I, wherein A is a nine-membered fused bicyclic aromatic ring system, wherein said ring system contains from 1 to 4 hetero atoms selected from nitrogen, oxygen and sulfur, and wherein said ring system may be substituted once or more than once by $R_5$.

In one embodiment, the invention provides a compound of formula I, wherein A is a ten-membered fused bicyclic aromatic ring system, wherein said ring system contains from 1 to 4 nitrogen atoms, and wherein said ring system may be substituted once or more than once by $R_5$.

In one embodiment, the invention provides a compound of formula I, wherein A is naphthyl, wherein said naphthyl may be substituted once or more than once by $R_5$.

In one embodiment, the invention provides a compound of formula I, wherein each $R_5$ independently is halogen; cyano; —C(O)NH$_2$; or —X$_2$—R$_6$;
$X_2$ is selected from bond; carbonyl; oxygen; —C(O)—NH—; and —C(O)—O—;
$R_6$ is $C_{1-6}$alkyl; $C_{1-6}$halogenalkyl; or $C_{1-4}$alkoxy-$C_{1-6}$alkyl.

In one embodiment, the invention provides a compound of formula I, wherein A is a six-membered monocyclic aromatic ring system, wherein said ring system contains from 1 to 3 nitrogen atoms, and wherein said ring system may be substituted once or more than once by $R_5$; and wherein each $R_5$ independently is halogen; cyano; —C(O)NH$_2$; or —X$_2$—R$_6$;
$X_2$ is selected from bond; carbonyl; oxygen; —C(O)—NH—; and —C(O)—O—;
$R_6$ is $C_{1-6}$alkyl; $C_{1-6}$halogenalkyl; or $C_{1-4}$alkoxy-$C_{1-6}$alkyl.

In one embodiment, the invention provides a compound of formula I, wherein A is selected from

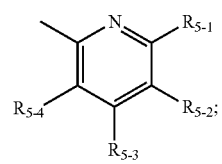

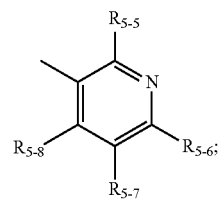

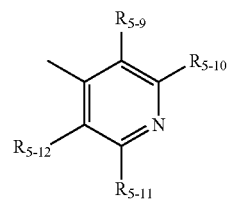

each of $R_{5-1}$, $R_{5-3}$ and $R_{5-4}$ independently is hydrogen or halogen;
$R_{5-2}$ is hydrogen; halogen; cyano; —C(O)NH$_2$; or —X$_2$—R$_6$;
$X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl; each of $R_{5-5}$, $R_{5-7}$ and $R_{5-8}$ independently is hydrogen or halogen;
$R_{5-6}$ is hydrogen; halogen; cyano; —C(O)NH$_2$; or —X$_2$—R$_5$;
$X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl; each of $R_{5-9}$, $R_{5-10}$, $R_{5-11}$ and $R_{5-12}$ independently is hydrogen or halogen.

In one embodiment, the invention provides a compound of formula I, wherein A is $A_1$; each of $R_{5-1}$, $R_{5-3}$ and $R_{5-4}$ independently is hydrogen or halogen; $R_{5-2}$ is hydrogen; halogen; cyano; —C(O)NH$_2$; or —X$_2$—R$_6$; $X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl.

In embodiment E1, the invention provides a compound of formula I, wherein
$R_1$ is isopropyl, cyclopropyl, cyclobutyl or cyclopentyl;
m is 1 or 2;

n is 0, 1 or 2 and wherein each $R_2$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_2$ at the same carbon atom form together with said carbon atom a $C_{3-4}$cycloalkyl;

$X_1$ is oxygen;

p is 1 and q is 1;

p is 0 and q is 1; or p is 0 and q is 0;

r is 0, 1 or 2 and wherein each $R_2$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_2$ at the same carbon atom form together with said carbon atom a $C_{3-4}$cycloalkyl;

A is a five- to six-membered monocyclic aromatic ring system, wherein said ring system may contain from 1 to 3 hetero atoms selected from nitrogen, oxygen and sulfur, and wherein said ring system may be substituted once or more than once by $R_5$;

each $R_5$ independently is halogen; cyano; —C(O)NH$_2$; or —X$_2$—R$_6$;

$X_2$ is selected from bond; carbonyl; oxygen; —C(O)—NH—; and —C(O)—O—; and $R_6$ is $C_{1-6}$alkyl; $C_{1-6}$halogenalkyl; or $C_{1-4}$alkoxy-$C_{1-6}$alkyl.

Within said embodiment E1, the invention further provides a compound of formula I, wherein $R_1$ is isopropyl.

Within said embodiment E1, the invention further provides a compound of formula I, wherein m is 1.

Within said embodiment E1, the invention further provides a compound of formula I, wherein m is 2.

Within said embodiment E1, the invention further provides a compound of formula I, wherein p is 1 and q is 1.

Within said embodiment E1, the invention further provides a compound of formula I, wherein n is 0.

Within said embodiment E1, the invention further provides a compound of formula I, wherein p is 1 and q is 1.

Within said embodiment E1, the invention further provides a compound of formula I, wherein p is 0 and q is 1.

Within said embodiment E1, the invention further provides a compound of formula I, wherein p is 0 and q is 0.

Within said embodiment E1, the invention further provides a compound of formula I, wherein A is a six-membered monocyclic aromatic ring system, wherein said ring system contains from 1 to 3 nitrogen atoms and wherein said ring system may be substituted once or more than once by $R_5$.

Within said embodiment E1, the invention further provides a compound of formula I, wherein A is selected from

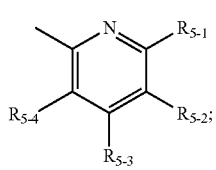

$A_1$

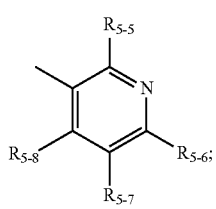

$A_2$

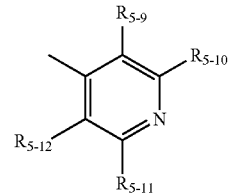

$A_3$ each of $R_{5-1}$, $R_{5-3}$ and $R_{5-4}$ independently is hydrogen or halogen;

$R_{5-2}$ is hydrogen; halogen; cyano; —C(O)NH$_2$; or —X$_2$—R$_6$;

$X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl; each of $R_{5-5}$, $R_{5-7}$ and $R_{5-8}$ independently is hydrogen or halogen;

$R_{5-8}$ is hydrogen; halogen; cyano; —C(O)NH$_2$; or —X$_2$—R$_6$;

$X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl; each of $R_{5-9}$, $R_{5-10}$, $R_{5-11}$ and $R_{5-12}$ independently is hydrogen or halogen.

Within said embodiment E1, the invention further provides a compound of formula I, wherein A is $A_1$; each of $R_{5-1}$, $R_{5-3}$ and $R_{5-4}$ independently is hydrogen or halogen; $R_{5-2}$ is hydrogen; halogen; cyano; —C(O)NH$_2$; or —X$_2$—R$_6$; $X_2$ is selected from bond; carbonyl; oxygen; —C(O)—NH—; and —C(O)—O—; $R_6$ is $C_{1-8}$alkyl; $C_{1-6}$halogenalkyl; or $C_{1-4}$alkoxy-$C_{1-6}$alkyl.

Within said embodiment E1, the invention further provides a compound of formula I, wherein $R_1$ is isopropyl, cyclopropyl, cyclobutyl or cyclopentyl; m is 1 or 2; $X_1$ is oxygen; p is 1 and q is 1; n is 0; p is 1 and q is 1; A is $A_1$; each of $R_{5-1}$, $R_{5-3}$ and $R_{5-4}$ independently is hydrogen or halogen; $R_{5-2}$ is hydrogen; halogen; cyano; —C(O)NH$_2$; or —X$_2$—R$_6$; $X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl.

Within said embodiment E1, the invention further provides a compound of formula I, wherein $R_1$ is isopropyl; m is 1; $X_1$ is oxygen; p is 1 and q is 1; n is 0; p is 1 and q is 1; A is $A_1$; each of $R_{5-1}$, $R_{5-3}$ and $R_{5-4}$ is hydrogen; $R_{5-2}$ is hydrogen; halogen; cyano; —C(O)NH$_2$; or —X$_2$—R$_6$; $X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl.

Within said embodiment E1, the invention further provides a compound of formula I, wherein $R_1$ is isopropyl; m is 1; $X_1$ is oxygen; p is 1 and q is 1; n is 0; p is 1 and q is 1; A is $A_1$; each of $R_{5-1}$, $R_{5-3}$ and $R_{5-4}$ is hydrogen; $R_{5-2}$ is halogen; cyano; —C(O)NH$_2$; or —X$_2$—R$_6$; $X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl.

In embodiment E2, the invention provides a compound of formula I, wherein $R_1$ is isopropyl, cyclopropyl, cyclobutyl or cyclopentyl;

m is 1 or 2;

n is 0, 1 or 2 and wherein each $R_2$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_2$ at the same carbon atom form together with said carbon atom a $C_{3-4}$cycloalkyl;

$X_1$ is —N(R$_4$)— and $R_4$ is hydrogen, $C_{1-6}$alkyl, $C_{3-6}$cycloalkyl, or $C_{3-6}$cycloalkyl-$C_{1-2}$alkyl;

p is 1 and q is 1;

p is 0 and q is 1; or p is 0 and q is 0;

r is 0, 1 or 2 and wherein each $R_2$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_2$ at the same carbon atom form together with said carbon atom a $C_{3-4}$cycloalkyl;

A is a five- to six-membered monocyclic aromatic ring system, wherein said ring system may contain from 1 to 3 hetero atoms selected from nitrogen, oxygen and sulfur, and wherein said ring system may be substituted once or more than once by $R_5$;

each $R_5$ independently is halogen; cyano; —C(O)NH$_2$; or —X$_2$—R$_6$;

$X_2$ is selected from bond; carbonyl; oxygen; —C(O)—NH—; and —C(O)—O—; and $R_6$ is $C_{1-6}$alkyl; $C_{1-6}$halogenalkyl; or $C_{1-4}$alkoxy-$C_{1-6}$alkyl.

Within said embodiment E2, the invention further provides a compound of formula I, wherein $R_1$ is isopropyl.

Within said embodiment E2, the invention further provides a compound of formula I, wherein m is 1.

Within said embodiment E2, the invention further provides a compound of formula I, wherein m is 2.

Within said embodiment E2, the invention further provides a compound of formula I, wherein p is 1 and q is 1.

Within said embodiment E2, the invention further provides a compound of formula I, wherein n is 0.

Within said embodiment E2, the invention further provides a compound of formula I, wherein $X_1$ is —N($R_4$)— and $R_4$ is hydrogen.

Within said embodiment E2, the invention further provides a compound of formula I, wherein p is 1 and q is 1.

Within said embodiment E2, the invention further provides a compound of formula I, wherein p is 0 and q is 1.

Within said embodiment E2, the invention further provides a compound of formula I, wherein p is 0 and q is 0.

Within said embodiment E2, the invention further provides a compound of formula I, wherein A is a six-membered monocyclic aromatic ring system, wherein said ring system contains from 1 to 3 nitrogen atoms and wherein said ring system may be substituted once or more than once by $R_5$.

Within said embodiment E2, the invention further provides a compound of formula I, wherein A is selected from

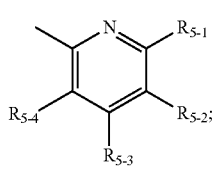

$A_1$

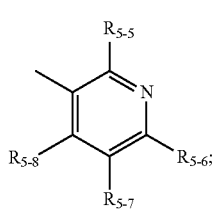

$A_2$

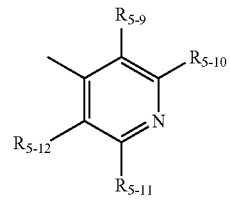

$A_3$ each of $R_{5-1}$, $R_{5-3}$ and $R_{5-4}$ independently is hydrogen or halogen;
$R_{5-2}$ is hydrogen; halogen; cyano; —C(O)NH$_2$; or —X$_2$—R$_6$;
$X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl; each of $R_{5-5}$, $R_{5-7}$ and $R_{5-8}$ independently is hydrogen or halogen;
$R_{5-6}$ is hydrogen; halogen; cyano; —C(O)NH$_2$; or —X$_2$—R$_6$;
$X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl; each of $R_{5-9}$, $R_{5-10}$, $R_{5-11}$ and $R_{5-12}$ independently is hydrogen or halogen.

Within said embodiment E2, the invention further provides a compound of formula I, wherein A is $A_1$; each of $R_{5-1}$, $R_{5-3}$ and $R_{5-4}$ independently is hydrogen or halogen; $R_{5-2}$ is hydrogen; halogen; cyano; —C(O)NH$_2$; or —X$_2$—R$_6$; $X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl.

Within said embodiment E2, the invention further provides a compound of formula I, wherein $R_1$ is isopropyl, cyclopropyl, cyclobutyl or cyclopentyl; m is 1 or 2; $X_1$ is —N($R_4$)— and $R_4$ is hydrogen; p is 1 and q is 1; n is 0; p is 1 and q is 1; A is $A_1$; each of $R_{5-1}$, $R_{5-3}$ and $R_{5-4}$ independently is hydrogen or halogen; $R_{5-2}$ is hydrogen; halogen; cyano; —C(O)NH$_2$; or —X$_2$—R$_6$; $X_2$ is selected from bond; carbonyl; oxygen; —C(O)—NH—; and —C(O)—O—; $R_5$ is $C_{1-6}$alkyl; $C_{1-6}$halogenalkyl; or $C_{1-4}$alkoxy-$C_{1-6}$alkyl.

Within said embodiment E2, the invention further provides a compound of formula I, wherein $R_1$ is isopropyl; m is 1; $X_1$ is —N($R_4$)— and $R_4$ is hydrogen; p is 1 and q is 1; n is 0; p is 1 and q is 1; A is $A_1$; each of $R_{5-1}$, $R_{5-3}$ and $R_{5-4}$ is hydrogen; $R_{5-2}$ is hydrogen; halogen; cyano; —C(O)NH$_2$; or —X$_2$—R$_6$; $X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl.

Within said embodiment E2, the invention further provides a compound of formula I, wherein $R_1$ is isopropyl; m is 1; $X_1$ is —N($R_4$)— and $R_4$ is hydrogen; p is 1 and q is 1; n is 0; p is 1 and q is 1; A is $A_1$; each of $R_{5-1}$, $R_{5-3}$ and $R_{5-4}$ is hydrogen; $R_{5-2}$ is halogen; cyano; —C(O)NH$_2$; or —X$_2$—R$_6$; $X_2$ is selected from bond; carbonyl; oxygen; —C(O)—NH—; and —C(O)—O—; $R_6$ is $C_1$ alkyl; $C_{1-6}$halogenalkyl; or $C_{1-4}$alkoxy-$C_{1-6}$alkyl.

In preferred embodiments, the invention relates to one or more than one of the compounds of the formula I mentioned in the Examples hereinafter or to a salt thereof.

Further examples of suitable compounds of the invention are compounds selected from the following group P:
Group P: Suitable Compounds of the Invention:
1-(5-carbamoyl pyridin-2-yl)piperidin-4-yl 4-isopropylpiperazine-1-carboxylate;
1-(5-carbamoyl pyridin-2-yl)piperidin-4-yl 4-cyclobutylpiperazine-1-carboxylate;
1-(5-carbamoylpyridin-2-yl)piperidin-4-yl 4-cyclopentylpiperazine-1-carboxylate;

1-(5-carbamoylpyridin-2-yl)piperidin-4-yl 4-cyclopropylpiperazine-1-carboxylate;
1-(5-(dimethylcarbamoyl)pyridin-2-yl)piperidin-4-yl 4-isopropylpiperazine-1-carboxylate;
1-(5-cyanopyridin-2-yl)piperidin-4-yl 4-isopropylpiperazine-1-carboxylate;
1-(5-(methylcarbamoyl)pyridin-2-yl)piperidin-4-yl 4-isopropylpiperazine-1-carboxylate;
1-(pyridin-2-yl)piperidin-4-yl 4-isopropylpiperazine-1-carboxylate;
1-(5-fluoropyridin-2-yl)piperidin-4-yl 4-isopropylpiperazine-1-carboxylate;
1-(5-(trifluoromethyl)pyridin-2-yl)piperidin-4-yl 4-isopropylpiperazine-1-carboxylate;
1-(5-methylpyridin-2-yl)piperidin-4-yl 4-isopropylpiperazine-1-carboxylate;
1-(5-(methoxycarbonyl)pyridin-2-yl)piperidin-4-yl 4-isopropylpiperazine-1-carboxylate;
1-(4-(isopropoxycarbonyl)pyridin-2-yl)piperidin-4-yl 4-isopropylpiperazine-1-carboxylate;
1-(5-(ethoxycarbonyl)pyridin-2-yl)piperidin-4-yl 4-isopropylpiperazine-1-carboxylate;
1-(5-carbamoylpyrazin-2-yl)piperidin-4-yl 4-isopropylpiperazine-1-carboxylate;
1-(5-acetylpyridin-2-yl)piperidin-4-yl 4-isopropylpiperazine-1-carboxylate;
1-(5-carbamoylpyridin-2-yl)piperidin-4-yl 4-isopropyl-1,4-diazepane-1-carboxylate;
1-(5-(hydroxymethyl)pyridin-2-yl)piperidin-4-yl 4-isopropylpiperazine-1-carboxylate;
1-(pyridin-2-yl)piperidin-4-yl 4-cyclobutylpiperazine-1-carboxylate;
1-(3-fluoropyridin-2-yl)piperidin-4-yl 4-isopropylpiperazine-1-carboxylate;
1-(3-(trifluoromethyl)pyridin-2-yl)piperidin-4-yl 4-isopropylpiperazine-1-carboxylate;
1-(3-(trifluoromethyl)pyridin-2-yl)piperidin-4-yl 4-cyclobutylpiperazine-1-carboxylate;
1-(3-cyanopyridin-2-yl)piperidin-4-yl 4-cyclobutylpiperazine-1-carboxylate;
1-(3-(methoxycarbonyl)pyridin-2-yl)piperidin-4-yl 4-isopropylpiperazine-1-carboxylate;
1-(4-fluoropyridin-2-yl)piperidin-4-yl 4-isopropylpiperazine-1-carboxylate;
1-(4-cyanopyridin-2-yl)piperidin-4-yl 4-isopropylpiperazine-1-carboxylate;
1-(4-(trifluoromethyl)pyridin-2-yl)piperidin-4-yl 4-isopropylpiperazine-1-carboxylate;
1-(4-(methoxycarbonyl)pyridin-2-yl)piperidin-4-yl 4-isopropylpiperazine-1-carboxylate;
1-(4-(methoxycarbonyl)pyridin-2-yl)piperidin-4-yl 4-cyclobutylpiperazine-1-carboxylate;
1-(4-methoxypyridin-2-yl)piperidin-4-yl 4-isopropylpiperazine-1-carboxylate;
1-(4-(methoxymethyl)pyridin-2-yl)piperidin-4-yl 4-isopropylpiperazine-1-carboxylate;
1-(4-(hydroxymethyl)pyridin-2-yl)piperidin-4-yl 4-isopropylpiperazine-1-carboxylate;
1-(5-fluoropyridin-2-yl)piperidin-4-yl 4-cyclobutylpiperazine-1-carboxylate;
1-(5-(methoxycarbonyl)pyridin-2-yl)piperidin-4-yl 4-cyclobutylpiperazine-1-carboxylate;
1-(5-methoxypyridin-2-yl)piperidin-4-yl 4-cyclopropylpiperazine-1-carboxylate;
1-(5-methoxypyridin-2-yl)piperidin-4-yl 4-ethylpiperazine-1-carboxylate;
1-(5-methoxypyridin-2-yl)piperidin-4-yl 4-isopropylpiperazine-1-carboxylate;
1-(5-methoxypyridin-2-yl)piperidin-4-yl 4-cyclobutylpiperazine-1-carboxylate;
6-(4-(4-isopropylpiperazine-1-carbonyloxy)piperidin-1-yl) nicotinic acid;
1-(5-acetylpyridin-2-yl)piperidin-4-yl 4-cyclobutylpiperazine-1-carboxylate;
1-(5-(cyclobutylcarbamoyl)pyridin-2-yl)piperidin-4-yl 4-isopropylpiperazine-1-carboxylate;
1-(5-(2-hydroxypropan-2-yl)pyridin-2-yl)piperidin-4-yl 4-isopropylpiperazine-1-carboxylate;
1-(5-(2-oxopyrrolidin-1-yl)pyridin-2-yl)piperidin-4-yl 4-cyclobutylpiperazine-1-carboxylate;
1-(5-(2-oxopyrrolidin-1-yl)pyridin-2-yl)piperidin-4-yl 4-isopropylpiperazine-1-carboxylate;
1-(5-carbamoylpyridin-2-yl)piperidin-4-yl 4-(1-hydroxypropan-2-yl)piperazine-1-carboxylate;
(R)-1-(5-carbamoylpyridin-2-yl)piperidin-4-yl 4-(1-hydroxypropan-2-yl)piperazine-1-carboxylate;
(S)-1-(5-carbamoylpyridin-2-yl)piperidin-4-yl 4-(1-hydroxypropan-2-yl)piperazine-1-carboxylate;
1-(5-carbamoylpyridin-2-yl)piperidin-4-yl 4-(1-methoxypropan-2-yl)piperazine-1-carboxylate;
(R)-1-(5-carbamoylpyridin-2-yl)piperidin-4-yl 4-(1-methoxypropan-2-yl)piperazine-1-carboxylate;
(S)-1-(5-carbamoylpyridin-2-yl)piperidin-4-yl 4-(1-methoxypropan-2-yl)piperazine-1-carboxylate;
1-(5-carbamoylpyridin-2-yl)piperidin-4-yl 4-(2-hydroxyethyl)piperazine-1-carboxylate;
1-(5-(thiazol-2-yl)pyridin-2-yl)piperidin-4-yl 4-isopropylpiperazine-1-carboxylate;
1-(6-(trifluoromethyl)pyridin-2-yl)piperidin-4-yl 4-isopropylpiperazine-1-carboxylate;
1-(6-cyanopyridin-2-yl)piperidin-4-yl 4-cyclobutylpiperazine-1-carboxylate;
1-(6-(methoxycarbonyl)pyridin-2-yl)piperidin-4-yl 4-isopropylpiperazine-1-carboxylate;
1-(6-(methoxycarbonyl)pyridin-2-yl)piperidin-4-yl 4-cyclobutylpiperazine-1-carboxylate;
1-(6-(methoxymethyl)pyridin-2-yl)piperidin-4-yl 4-isopropylpiperazine-1-carboxylate;
1-(6-(methoxymethyl)pyridin-2-yl)piperidin-4-yl 4-cyclobutylpiperazine-1-carboxylate;
1-(6-(hydroxymethyl)pyridin-2-yl)piperidin-4-yl 4-isopropylpiperazine-1-carboxylate;
1-(6-(methoxypyridin-2-yl) piperidin-4-yl 4-isopropylpiperazine-1-carboxylate;
1-(6-cyanopyridin-2-yl)piperidin-4-yl 4-isopropylpiperazine-1-carboxylate;
1-(6-carbamoylpyridin-3-yl)piperidin-4-yl 4-isopropylpiperazine-1-carboxylate;
1-(6-(methoxycarbonyl)pyridin-3-yl)piperidin-4-yl 4-isopropylpiperazine-1-carboxylate;
1-(6-(methoxycarbonyl)pyridin-3-yl)piperidin-4-yl 4-cyclobutylpiperazine-1-carboxylate;
1-(6-(hydroxymethyl)pyridin-3-yl)piperidin-4-yl 4-isopropylpiperazine-1-carboxylate;
1-(6-(hydroxymethyl)pyridin-3-yl)piperidin-4-yl 4-cyclobutylpiperazine-1-carboxylate;
1-(6-(methoxymethyl)pyridin-3-yl)piperidin-4-yl 4-cyclobutylpiperazine-1-carboxylate;
1-(6-(methoxymethyl)pyridin-3-yl)piperidin-4-yl 4-isopropylpiperazine-1-carboxylate;
1-(6-carbamoylpyridin-3-yl)piperidin-4-yl 4-cyclobutylpiperazine-1-carboxylate;

1-(pyridin-4-yl)piperidin-4-yl 4-isopropylpiperazine-1-carboxylate;
1-(pyridin-4-yl)piperidin-4-yl 4-cyclobutylpiperazine-1-carboxylate;
1-(6-methoxypyridazin-3-yl)piperidin-4-yl 4-isopropylpiperazine-1-carboxylate;
1-(6-methoxypyridazin-3-yl)piperidin-4-yl 4-cyclobutylpiperazine-1-carboxylate;
1-(6-methoxypyrazin-2-yl)piperidin-4-yl 4-isopropylpiperazine-1-carboxylate;
1-(6-methoxypyrazin-2-yl)piperidin-4-yl 4-cyclobutylpiperazine-1-carboxylate;
1-(imidazo[1,2-a]pyridin-7-yl)piperidin-4-yl 4-isopropylpiperazine-1-carboxylate;
1-(imidazo[1,2-a]pyridin-7-yl)piperidin-4-yl 4-cyclobutylpiperazine-1-carboxylate;
1-(2-methylimidazo[1,2-a]pyridin-7-yl)piperidin-4-yl 4-isopropylpiperazine-1-carboxylate;
1-(4-carbamoylphenyl)piperidin-4-yl 4-cyclobutylpiperazine-1-carboxylate;
1-(thiazol-4-yl)piperidin-4-yl 4-isopropylpiperazine-1-carboxylate;
1-(thiazol-5-yl)piperidin-4-yl 4-isopropylpiperazine-1-carboxylate;
1-(thiazol-5-yl)piperidin-4-yl 4-cyclobutylpiperazine-1-carboxylate;
1-(thiazol-2-yl)piperidin-4-yl 4-isopropylpiperazine-1-carboxylate;
1-(5-methylthiazol-2-yl)piperidin-4-yl 4-isopropylpiperazine-1-carboxylate;
methyl 2-(4-(4-isopropylpiperazine-1-carbonyloxy)piperidin-1-yl)thiazole-5-carboxylate;
methyl 2-(4-(4-cyclobutylpiperazine-1-carbonyloxy)piperidin-1-yl)thiazole-5-carboxylate;
1-(5-carbamoylthiazol-2-yl)piperidin-4-yl 4-isopropylpiperazine-1-carboxylate;
1-(5-(hydroxymethyl)thiazol-2-yl)piperidin-4-yl 4-isopropylpiperazine-1-carboxylate;
1-(4-methylthiazol-2-yl)piperidin-4-yl 4-isopropylpiperazine-1-carboxylate;
1-(4-methylthiazol-2-yl)piperidin-4-yl 4-cyclobutylpiperazine-1-carboxylate;
methyl 2-(4-(4-isopropylpiperazine-1-carbonyloxy)piperidin-1-yl)thiazole-4-carboxylate;
1-(4-(hydroxymethyl)thiazol-2-yl)piperidin-4-yl 4-isopropylpiperazine-1-carboxylate;
1-(4-carbamoylthiazol-2-yl)piperidin-4-yl 4-isopropylpiperazine-1-carboxylate;
methyl 2-(4-(4-cyclobutylpiperazine-1-carbonyloxy)piperidin-1-yl)thiazole-4-carboxylate;
1-(1,3,4-thiadiazol-2-yl)piperidin-4-yl 4-isopropylpiperazine-1-carboxylate;
1-(1,3,4-thiadiazol-2-yl)piperidin-4-yl 4-cyclobutylpiperazine-1-carboxylate;
1-(5-methyl-1,3,4-thiadiazol-2-yl)piperidin-4-yl 4-isopropylpiperazine-1-carboxylate;
1-(5-morpholino-1,3,4-thiadiazol-2-yl)piperidin-4-yl 4-cyclobutylpiperazine-1-carboxylate;
1-(5-morpholino-1,3,4-thiadiazol-2-yl)piperidin-4-yl 4-isopropylpiperazine-1-carboxylate;
1-(5-carbamoylpyridin-2-yl)pyrrolidin-3-yl 4-isopropylpiperazine-1-carboxylate;
(R)-1-(5-carbamoylpyridin-2-yl)pyrrolidin-3-yl 4-isopropylpiperazine-1-carboxylate;
(S)-1-(5-carbamoylpyridin-2-yl)pyrrolidin-3-yl 4-isopropylpiperazine-1-carboxylate;
1-(5-(trifluoromethyl)pyridin-2-yl)pyrrolidin-3-yl 4-isopropylpiperazine-1-carboxylate;
(R)-1-(5-(trifluoromethyl)pyridin-2-yl)pyrrolidin-3-yl 4-isopropylpiperazine-1-carboxylate;
(S)-1-(5-(trifluoromethyl)pyridin-2-yl)pyrrolidin-3-yl 4-isopropylpiperazine-1-carboxylate;
1-(5-cyanopyridin-2-yl)pyrrolidin-3-yl 4-isopropylpiperazine-1-carboxylate;
(R)-1-(5-cyanopyridin-2-yl)pyrrolidin-3-yl 4-isopropylpiperazine-1-carboxylate;
(S)-1-(5-cyanopyridin-2-yl)pyrrolidin-3-yl 4-isopropylpiperazine-1-carboxylate;
1-(6-carbamoylpyridin-3-yl)pyrrolidin-3-yl 4-isopropylpiperazine-1-carboxylate;
(R)-1-(6-carbamoylpyridin-3-yl)pyrrolidin-3-yl 4-isopropylpiperazine-1-carboxylate;
(S)-1-(6-carbamoylpyridin-3-yl)pyrrolidin-3-yl 4-isopropylpiperazine-1-carboxylate;
1-(5-carbamoylpyridin-2-yl)azetidin-3-yl 4-isopropylpiperazine-1-carboxylate;
1-(5-cyanopyridin-2-yl)azetidin-3-yl 4-isopropylpiperazine-1-carboxylate;
1-(5-(trifluoromethyl)pyridin-2-yl)azetidin-3-yl 4-isopropylpiperazine-1-carboxylate; or
N-(1-(5-carbamoylpyridin-2-yl)piperidin-4-yl)-4-isopropylpiperazine-1-carboxamide;
or salts of these compounds.

In a further aspect, the invention also provides a process for the production of compounds of the formula I-1. Compounds of the formula I-1 are obtainable according to the following process as described in scheme 1:

Scheme 1:

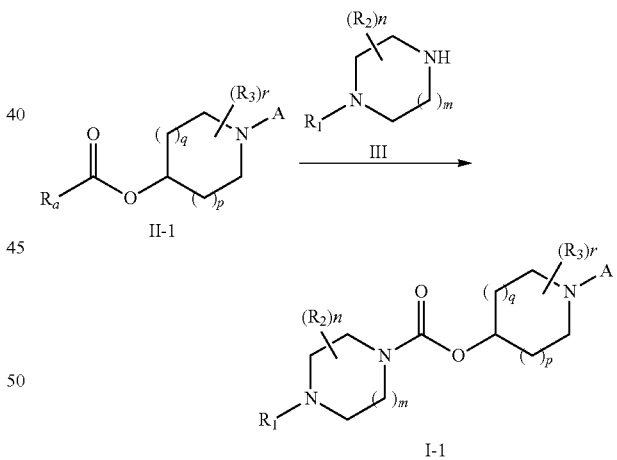

A compound of formula I-1, in which A, $R_1$, $R_2$, $R_3$, m, n, p, q and r are as defined under formula I, may be obtained by reacting a compound of formula II-1, in which A, $R_3$, p, q and r are as defined under formula I and $R_a$ is a leaving group, e.g. halogen, such as chloro, or 4-nitrophenyloxy (preferably $R_a$ is 4-nitrophenyloxy), with a compound of formula III, in which $R_1$, $R_2$, m and n are as defined under formula I, in the presence of a suitable base, e.g. diisopropylethylamine, in the presence of a suitable solvent, e.g. pyridine.

In a further aspect, the invention also provides a process for the production of compounds of the formula I-2. Compounds of the formula I-2 are obtainable according to the following process as described in scheme 2:

Scheme 2:

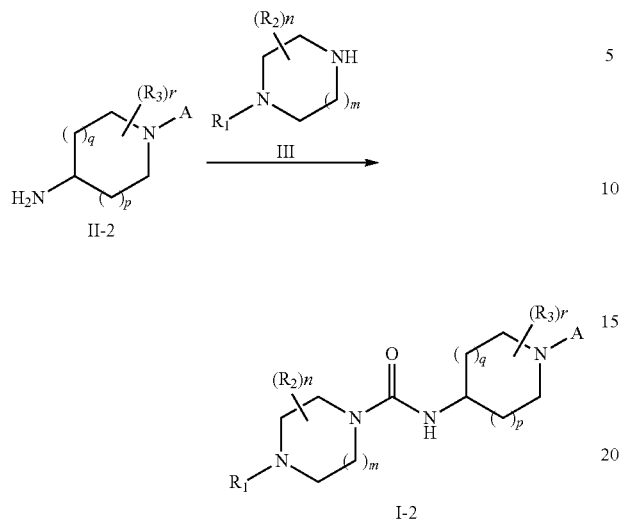

Scheme 3:

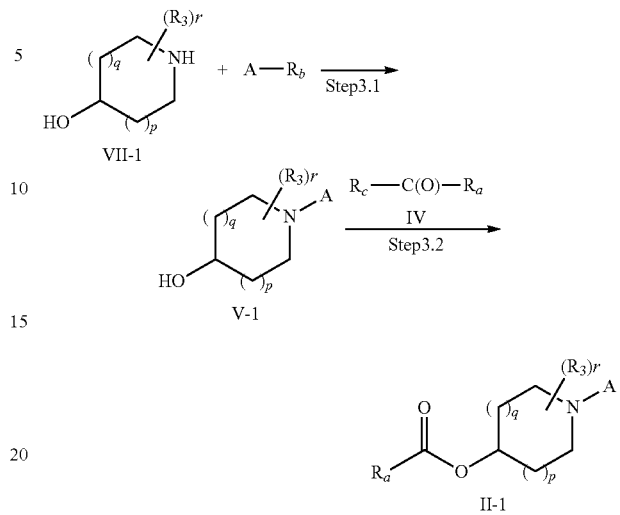

A compound of formula I-2, in which A, $R_1$, $R_2$, $R_3$, m, n, p, q and r are as defined under formula I, may be obtained by reacting a compound of formula II-2, in which A, $R_3$, p, q and r are as defined under formula I, with a compound of formula III, in which in which $R_1$, $R_2$, m and n are as defined under formula I, in the presence of carbonyldiimidazole, a suitable base, e.g. diisopropylethylamine, and a suitable solvent, e.g. dimethylformamide.

Further compounds of formula I or their precursors may be obtainable from compounds of formula I-1 or I-2, prepared as described according to scheme 1 or 2, or their precursors (e.g. compounds of formulae II-1, II-2 and/or III) by reduction, oxidation and/or other functionalization of resulting compounds and/or by cleavage of any protecting group(s) optionally present, and of recovering the so obtainable compound of the formula I. Compounds of the formula I can also be prepared by further conventional processes, e.g. as described in the Examples, which processes are further aspects of the invention.

The invention also contemplates that compounds of formula (I) may be formed by in vivo biotransformation from pro-drugs.

The reactions can be effected according to conventional methods, for example as described in the Examples.

The work-up of the reaction mixtures and the purification of the compounds thus obtainable may be carried out in accordance with known procedures.

Acid addition salts may be produced from the free bases in known manner, and vice-versa.

Starting materials, e.g. compounds of the formulae II-1, II-2 and III may be known or prepared according to conventional procedures starting from known compounds, for example as described in the Examples.

In a further aspect, the invention also provides a process for the production of compounds of the formula II-1. Compounds of the formula II-1 are obtainable according to the following process as described in scheme 3:

Step 3.1:
A compound of formula V-1, in which A, $R_3$, p, q and r are as defined under formula I, may be obtained by reacting a compound of formula VII-1, in which $R_3$, p, q and r are as defined under formula I, with a compound of formula VI, in which A is as defined under formula I and $R_b$ is halogen, for example chloro, in the presence of a suitable base, e.g. diisopropylethylamine, and optionally in the presence of a suitable solvent.

Step 3.2:
A compound of formula II-1, in which A, $R_1$, $R_2$, $R_3$, m, n, p, q and r are as defined under formula I, may be obtained by reacting the compound of V-1 with a compound of formula IV, in which $R_c$ is halogen, for example chloro, and $R_a$ is a leaving group, e.g. halogen or 4-nitrophenyloxy (preferably $R_a$ is 4-nitrophenyloxy), in the presence of a suitable base, e.g. diisopropylethylamine, and in the presence of a suitable solvent, e.g. pyridine.

In a further aspect, the invention also provides a novel compound of formula II-1

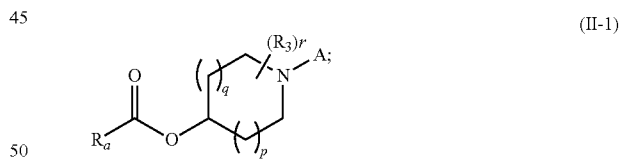

(II-1)

or a salt thereof; in which p, q, r and $R_3$ are as defined under formula I; $R_a$ is a leaving group, e.g. halogen, such as chloro, or a group selected from

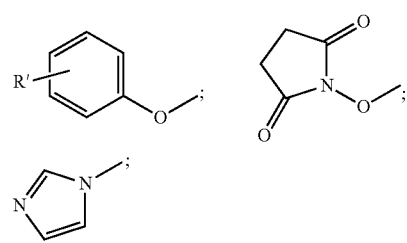

wherein R' is hydrogen or nitro; preferably $R_a$ is 4-nitrophenyloxy; A is a five- to six-membered monocyclic aromatic ring system, wherein said ring system may contain from 1 to 3 hetero atoms selected from nitrogen, oxygen and sulfur, and wherein said ring system may be substituted once or more than once by $R_5$; wherein each $R_5$ independently is halogen; cyano; —C(O)NH$_2$; or —X$_2$—R$_6$; X$_2$ is selected from bond; carbonyl; oxygen; —C(O)—NH—; and —C(O)—O—; and $R_6$ is $C_{1-6}$alkyl; $C_{1-6}$halogenalkyl; or $C_{1-4}$alkoxy-$C_{1-6}$alkyl.

In one embodiment of said further aspect, the invention provides a compound of formula II-1, wherein
p is 1 and q is 1;
p is 0 and q is 1; or
p is 0 and q is 0;
r is 0, 1 or 2 and wherein each $R_2$ independently is halogen, $C_{1-4}$alkyl, $C_{1-4}$halogenalkyl, $C_{1-4}$alkoxy, $C_{1-4}$halogenalkoxy or $C_{3-4}$cycloalkyl; or two $R_2$ at the same carbon atom form together with said carbon atom a $C_{3-4}$cycloalkyl;
A is a five- to six-membered monocyclic aromatic ring system, wherein said ring system may contain from 1 to 3 hetero atoms selected from nitrogen, oxygen and sulfur, and wherein said ring system may be substituted once or more than once by $R_5$;
each $R_5$ independently is halogen; cyano; —C(O)NH$_2$; or —X$_2$—R$_6$;
$X_2$ is selected from bond; carbonyl; oxygen; —C(O)—NH—; and —C(O)—O—; and
$R_6$ is $C_{1-6}$alkyl; $C_{1-6}$halogenalkyl; or $C_{1-4}$alkoxy-$C_{1-6}$alkyl.

In one embodiment of said further aspect, the invention provides a compound of formula II-1, wherein $R_1$ is isopropyl; m is 1; $X_1$ is oxygen; p is 1 and q is 1; n is 0; p is 1 and q is 1; A is $A_1$; each of $R_{5-1}$, $R_{5-3}$ and $R_{5-4}$ is hydrogen; $R_{5-2}$ is halogen; cyano; —C(O)NH$_2$; or —X$_2$—R$_6$; $X_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl.

In another aspect, the invention provides a pharmaceutical composition comprising a compound of the invention and a pharmaceutically acceptable carrier. The pharmaceutical composition can be formulated for particular routes of administration such as oral administration, parenteral administration, and rectal administration, etc. In addition, the pharmaceutical compositions of the invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with
a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets.

These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides anhydrous pharmaceutical compositions and dosage forms comprising the compounds of the invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the invention as an active ingredient will decompose. Such agents, which are referred to herein as "stabilizers," include, but are not limited to, antioxidants such as ascorbic acid, pH buffers, or salt buffers, etc.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The compounds of formula I or pharmaceutical acceptable salts thereof exhibit valuable pharmacological properties and are therefore useful as pharmaceuticals.

Furthermore, compounds of formula I may be useful for research on H3 receptors, e.g. as tool compounds.

In particular, compounds of formula I exhibit a H3 receptor antagonistic action at human H3 receptors.

As used herein, the term "H3 receptor antagonist" encompasses H3 receptor inverse agonists and H3 receptor neutral antagonists.

H3 receptor antagonistic action can be determined in vitro, for example, at recombinant human H3 receptors, using different procedures like, for example, measurement of the inhibition of the agonist induced elevation of intracellular cAMP concentration, e.g. as described herein.

The compounds of the invention may be therefore useful in the prevention, treatment or delay of progression of disorders mediated by H3 receptors.

Disorders mediated by H3 receptors may be for example
i) disorders of sleep and wakefulness with excessive daytime sleepiness; such as narcolepsy, e.g. narcolepsy with or without cataplexy; secondary narcoleptic syndromes; central sleep apnea syndrome; or obstructive sleep apnea syndrome;
ii) disorders or conditions associated with increased fatigue or hypersomnolence; such as fatigue associated with autoimmune disease, e.g. Multiple Sclerosis or Rheumatoid Arthritis; fatigue associated with neurodegenerative disorders, e.g. as Parkinson's disease, Multisystem atrophy, Shy-Drager-Syndrome or Progressive Supranuclear Palsy; fatigue associated with other medical conditions or their treatment, such as depression, burnout syndrome, or adjustment disorder; stress-associated disorders with fatigue, e.g. acute stress disorder or posttraumatic stress disorder; cancer-associated fatigue; chemotherapy-associated fatigue; fatigue associated with shift-work; jet lag; chronic fatigue syndrome; fibromyalgia; postinfectious fatigue; postoperative fatigue or dizziness;
iii) disorders or conditions with impaired cognition; such as Alzheimers Disease; Mild Cognitive Impairment; Diffuse-Lewy body dementia; vascular dementia; Huntington's disease; Wilson's disease; frontotemporal dementia; other forms of organic dementia or organic cognitive impairment; multiple sclerosis; schizophrenia; schizoaffective disorder; bipolar-affective disorder;
iv) disorders of substance abuse or addiction; such as to alcohol, cocaine, opioids, cannabinoids, nicotine or other substances with abuse or addiction potential;
v) non-substance abuse conditions; such as pathological gambling;
vi) disorders associated with dysfunctional feeding behaviours and/or metabolic syndrome; such as antipsychotic drug-associated weight gain; Prader-Willi-Sndrome; Moon-Bardet-Biedl Syndrome; obesity; atypical depression; bulimia nervosa; or binge eating disorder;
vii) disorders with increased anxiety; such as general anxiety disorder; social anxiety disorder; or panic disorder;
viii) other neuropsychiatric or neurological disorders; such as Tourette syndrome; primary tic disorders; secondary tic disorders; attention deficit hyperactivity disorders; obsessive-compulsive disorders; headache disorders, e.g. episodic migraine, chronic migraine, cluster headache, or tension-type headache; acute disorders associated with neuronal loss, e.g. stroke; REM-sleep behavioural disorder; restless-legs syndrome; or epilepsy;
ix) other medical conditions or disorders; such as disorders with impaired hearing; vertigo; Menieres Disease; itch; pruritus; inflammatory pain; neuropathic pain; diabetes mellitus; cancer; atherosclerosis; allergies; or allergic rhinitis;

Of particular importance is the treatment of narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; or Attention-deficit hyperactivity disorder.

For the above-mentioned indications (the conditions and disorders) the appropriate dosage will vary depending upon, for example, the compound employed, the host, the mode of administration and the nature and severity of the condition being treated. However, in general, satisfactory results in animals are indicated to be obtained at a daily dosage of from about 0.001 to about 500 mg/kg body weight, preferably from about 0.1 to about 10 mg/kg body weight, e.g. 1 mg/kg. In larger mammals, for example humans, an indicated daily dosage is in the range from about 0.1 to about 1000 mg, preferably from about 0.1 to about 400 mg, most preferably from about 0.1 to about 100 mg of the compound of the invention conveniently administered, for example, in divided doses up to four times a day.

For use according to the invention, a compound of the invention may be administered as single active agent or in combination with other active agents, in any usual manner, e.g. orally, for example in the form of tablets or capsules, or parenterally, for example in the form of injection solutions or suspensions. A combination comprising a compound of the invention and one or more other therapeutically active agents will be referred to as "combination of the invention".

In the case of narcolepsy, the compound of the invention may be combined at least with one active agent selected from the group consisting of
a noradrenaline-dopamine reuptake inhibitor, such as modafinil or armodafinil;
a tri- or tetracyclic antidepressant, such as clomipramine;
a serotonin-noradrenaline reuptake inhibitor, such as venlafaxine or duloxetine;
a selective serotonin reuptake inhibitor, such as paroxetine;
a noradrenaline reuptake inhibitor, such as reboxetine or atomoxetine;
a MAO-B inhibitor such as selegiline;
a gamma-hydroxy-butyrate; and
a psychostimulant, such as methylphenidate.

Said combination of the invention is useful to treat narcolepsy.

In the case of fatigue associated with multiple sclerosis, the compound of the invention may be combined at least with one active agent selected from the group consisting of
a sphingosine-1-phosphate analog, such as fingolimod; and
another immunosuppressive agent, such as prednisolone or methotrexate.

In the case of fatigue associated with Parkinson's disease, the compound of the invention may be combined at least with one active agent selected from the group consisting of
L-Dopa with or without a Decarboxylase inhibitor, such as Benzerazid or Carbidopa, and/or with or without a catechol-O-Methyltransferase inhibitor, such as entacapone or tolcapone;
a dopamine receptor agonist, such as ropinirole or pergolide; and
a MAO-B inhibitor, such as selegiline.

In the case of cognitive impairment associated with schizophrenia, the compound of the invention may be combined at least with one antipsychotic agent, such as haloperidol, olanzapine; risperidone; quetiapine; amisulpiride; or aripirazole.

In the case of cognitive impairment associated with Alzheimer's disease, the compound of the invention may be combined at least with one active agent selected from the group consisting of
a cholinergic agent, such as an acetylcholinesterase inhibitor, e.g. donepezil, rivastigmine or galantamine; and
an antiglutamatergic agent, such as memantine.

In the case of Tourette's syndrome, the compound of the invention may be combined at least with one active agent selected from the group consisting of
an alpha receptor agonist, such as clonidine;
an antipsychotic agent, such as fluphenazine, haloperidol, pimozide, aripirazole, of risperidone; and
a dopamine depleting agent, such as tetrabenazine.

In the case of attention-deficit hyperactivity disorder, the compound of the invention may be combined at least with one active agent selected from the group consisting of
a noradrenaline-dopamine reuptake inhibitor, such as modafinil or armodafinil;
a tri- or tetracyclic antidepressant, such as clomipramine;
a psychostimulant, such as methylphenidate
a noradrenaline-serotonin reuptake inhibitor, such as venlafaxine or duloxetine;
a selective serotonin reuptake inhibitor, such as paroxetine; and
a noradrenaline reuptake inhibitor, such as reboxetine or atomoxetine.

The compounds of the invention may be useful for the prevention of the above-mentioned conditions and disorders.

The compounds of the invention may be useful for the treatment of the above-mentioned conditions and disorders.

The compounds of the invention may be useful for the delay of progression of the above-mentioned conditions and disorders.

The usefulness of the compounds of the invention in the treatment of the above-mentioned disorders can be confirmed in a range of standard tests including those indicated below:

The in vivo activity of the compounds of the invention can be assessed by measuring the effects on brain histamine release (quantification of the histamine metabolite tele-methylhistamine) and/or by testing the effects on wakefulness in rats with EEG electrodes.

Compounds of the invention may be especially useful in the treatment of an indication selected from: narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

Thus, as a further embodiment, the invention provides the use of a compound of formula (I) or a pharmaceutically acceptable salt thereof as a medicament.

As a further embodiment, the invention provides the use of a compound of formula (I) or a pharmaceutically acceptable salt thereof in therapy.

In a further embodiment, the therapy is selected from a disease which is ameliorated by inhibition of H3 receptor action. In another embodiment, the disease is selected from the afore-mentioned list, e.g. is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

In another embodiment, the invention provides a method of treating a disease which is ameliorated by inhibition of H3 receptors comprising administration of a therapeutically acceptable amount of a compound of formula (I) or a pharmaceutically acceptable salt thereof. In a further embodiment, the disease is selected from the afore-mentioned list, e.g. is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

The term "a therapeutically effective amount" of a compound of the invention refers to an amount of the compound of the invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the invention that, when administered to a subject, is effective to (1) at least partially alleviating, inhibiting, preventing and/or ameliorating a condition, or a disorder or a disease (i) mediated by H3 receptors, or (ii) associated with H3 receptor activity, or (iii) characterized by abnormal activity of H3 receptors; or (2) reducing or inhibiting the activity of H3 receptors; or (3) reducing or inhibiting the expression of H3 receptors. In another non-limiting embodiment, the term "a therapeutically effective amount" refers to the amount of the compound of the invention that, when administered to a cell, or a tissue, or a non-cellular biological material, or a medium, is effective to at least partially reducing or inhibiting the activity of H3 receptors; or at least partially reducing or inhibiting the expression of H3 receptors.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The pharmaceutical composition or combination of the invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between e.g. about 0.001-500 mg/kg, or between e.g. about 0.1-100 mg/kg.

The activity of a compound of the invention can be assessed by in vitro & in vivo methods described herein.

The compound of the invention may be administered either simultaneously with, or before or after, at least one other therapeutic agent. The compound of the invention may be administered separately, by the same or different route of administration, or together in the same pharmaceutical composition.

The following Examples illustrate the invention, but do not limit it.

EXAMPLES

Abbreviations

AcOH acetic acid
BINAP 2,2'-bis(diphenylphosphino)-1,1'-binaphthyl
Boc tert-butoxycarbonyl
BTC triphosgene
CDI carbonyldiimidazole
DCM dichloromethane
DIPEA N-ethyl-N-isopropylpropan-2-amine (Diisopropylethylamine)
DMF dimethylformamide
Et3N triethyl amine
EtOH ethanol
EtOAc ethyl acetate
h hour(s)
HPLC high pressure liquid chromatography
LCMS liquid chromatography mass spectroscopy
min minute(s)
MeOH methanol
NMR nuclear magnetic resonance spectrometry
$Pd_2(dba)_3$ tris(dibenzylideneacetone)dipalladium(0)
Rt retention time
rt room temperature
t-BuOK Potassium tert-butanolate
TBAF tetrabutylammonium fluoride
TBSCl tert-Butyldimethylsilyl chloride
THF tetrahydrofuran
TLC thin layer chromatography
LCMS Conditions (%=Percent by Volume):
Method A ($Rt_A$=Retention Time A)

Agilent 1200 HPLC/6110 SQ system; Mobile Phase: A: water (10 mM $NH_4HCO_3$) B: Acetonitrile; Gradient: 5% B for 0.2 min, increase to 95% B within 1.2 min; 95% B for 1.5 min, back to 5% B within 0.01 min; Flow Rate: 1.8 ml/min; Column: XBridge C18, 4.6*50 mm, 3.5 um; Oven Temperature: 50° C.

Method B ($Rt_B$=Retention Time B)

Agilent 1200 HPLC/6110 SQ system; Mobile Phase: A: Water (0.01% $NH_3.H_2O$), B: Acetonitrile; Gradient: 5%-95% B in 1.4 min; Flow Rate: 1.8 ml/min; Column: XBridge C18, 4.6*50 mm, 3.5 μm; Oven Temperature: 50° C.

Method C ($Rt_C$=Retention Time C)

Agilent 1200 HPLC/6110 SQ system; Mobile Phase: A: water (0.05% TFA) B: Acetonitrile (0.05% TFA); Gradient: 5% B for 0.2 min, increase to 95% B within 1.2 min, 95% B for 1.6 min, back to 5% B within 0.01 min; Flow Rate: 1.8 mL/min; Column: Sunfire, 3.5 um, 50*4.6 mm; Oven Temperature: 50° C.

Method D ($Rt_C$=Retention Time D)

Agilent 1200 HPLC/6130 SQ system; Mobile Phase: A: water (0.05% TFA) B: Acetonitrile (0.05% TFA); Gradient: B from 1% increase to 99% within 1.0 min, 95% B for 1 min; Flow Rate: 1.8 mL/min; Column: Merck RP-18e, 2 mm*50 mm; Oven Temperature: 40° C.

$^1$H NMR Instruments:

Bruker AVANCE III (500 MHz), Bruker AVANCE III (400 MHz)

Example 1.1

1-(5-carbamoylpyridin-2-yl)-piperidin-4-yl-4-isopropylpiperazine-1-carboxylate (Method A)

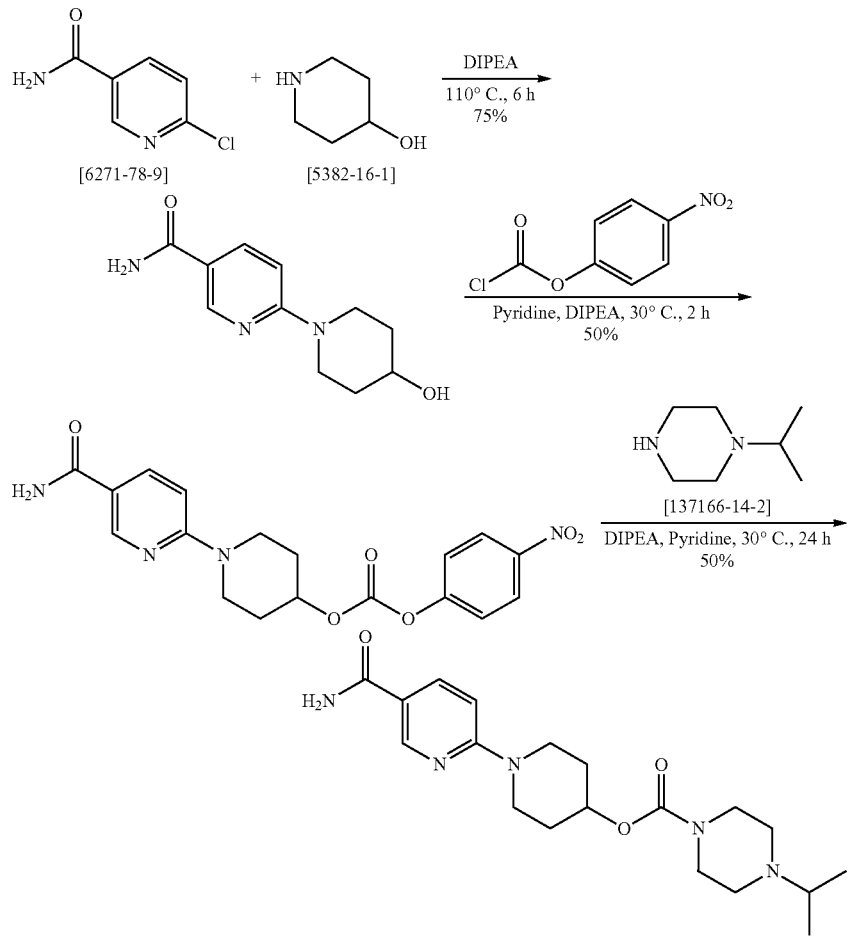

a) 6-(4-hydroxypiperidin-1-yl)nicotinamide

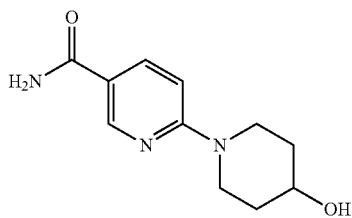 [SMILES: NC(=O)c1ccc(N2CCC(O)CC2)nc1]

To the solution of 6-chloronicotinamide (5.0 g, 32 mmol) in DIPEA (50 mL), piperidin-4-ol (3.2 mg, 32 mmol) was added and the mixture was stirred at 110° C. for 8 h. The reaction mixture was concentrated under reduced pressure to afford the crude product. The residue was further purified by silica gel chromatography (DCM: MeOH=20:1) to afford the title compound (5.3 g, 75%) as a yellowish solid. [LCMS $Rt_B$=1.39 min, $[M+H]^+$=222.1].

b) 1-(5-carbamoylpyridin-2-yl)-piperidin-4-yl 4-nitrophenyl carbonate

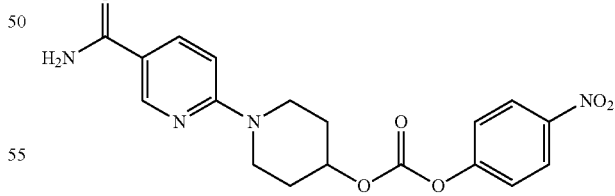

To the solution of 6-(4-hydroxypiperidin-1-yl)nicotinamide (3.32 g, 15 mmol) in pyridine (10 mL) was added DIPEA (3.87 g, 30.0 mmol) and 4-nitrophenyl carbonochloridate (6.03 g, 30 mmol). The resulting mixture was stirred at 30° C. for 2 h before it was concentrated under reduced pressure to afford the crude product. The residue was further purified by silica gel chromatography (DCM: MeOH=100:0 to 20:1) to afford the title compound (3 g, 50%) as a white solid. [LCMS $Rt_B$=1.79 min, $[M+H]^+$=387.0].

c) 1-(5-carbamoylpyridin-2-yl)piperidin-4-yl 4-isopropylpiperazine-1-carboxylate

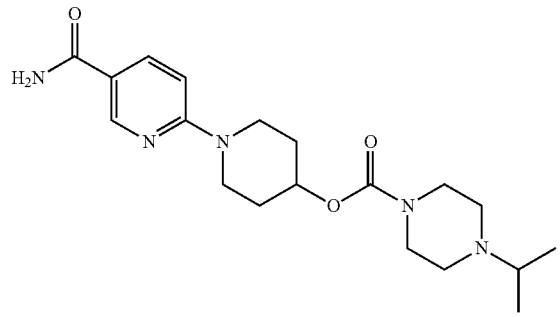 [SMILES: CC(C)N1CCN(C(=O)OC2CCN(c3ccc(C(N)=O)cn3)CC2)CC1]

To the solution of 1-(5-carbamoylpyridin-2-yl)-piperidin-4-yl 4-nitrophenyl carbonate (3.0 g, 7.77 mmol) in pyridine (50 ml) was added 1-isopropylpiperazine (1.05 g, 8.16 mmol) and DIPEA (2.01 g, 15.5 mmol). The resulting mixture was stirred at 30° C. for 2 h before it was concentrated to dryness. The residue was further purified by silica gel chromatography (DCM: MeOH=50:1 to 5:1) to afford the title compound as a white solid (1.46 g, 50%). MP: 200.1-203.6° C. [$^1$H NMR (DMSO, 500 MHz): δ 8.61 (d, J=2 Hz, 1H), 7.95 (dd, J=2.5 Hz, 9 Hz, 1H), 7.53 (s, 1H), 7.12 (s, 1H), 6.87 (d, J=9.5 Hz, 1H), 4.83 (m, 1H), 3.90-3.85 (m, 2H), 3.54-3.49 (m, 2H), 3.34 (s, 4H), 2.67-2.64 (m, 1H), 2.38 (m, 4H), 1.89-1.85 (m, 2H), 1.58-1.54 (m, 2H), 0.95 (d, J=6.5 Hz, 6H); LCMS Rt$_A$=1.61 min, [M+H]$^+$=376.3].

Example 2.1

1-(5-carbamoylpyridin-2-yl)-pyrrolidin-3-yl-4-isopropylpiperazine-1-carboxylate (Method B)

a) 6-(3-hydroxypyrrolidin-1-yl)nicotinamide

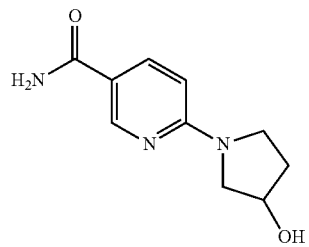 [SMILES: NC(=O)c1ccc(N2CCC(O)C2)nc1]

To a solution of 6-chloronicotinamide (0.16 g, 1 mmol) and pyrrolidin-3-ol (0.87 g, 1 mmol) in DMF (5 ml) was added K$_2$CO$_3$ (0.41 g, 3 mmol). The resulting solution was stirred under nitrogen at 125° C. for 24 h, and then allowed to cool to ambient temperature. The reaction mixture was then filtered and the filter cake was washed with ethyl acetate. The combined filtrates were concentrated to afford the title compound (0.145 g, 70%) as a yellow solid. [LCMS Rt$_A$=1.23 min, [M+H]$^+$=208.1].

b) 1-(5-carbamoylpyridin-2-yl)-pyrrolidin-3-yl 4-nitrophenyl carbonate

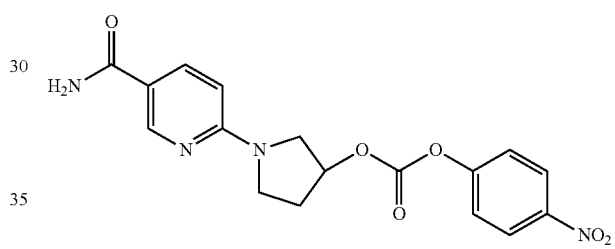

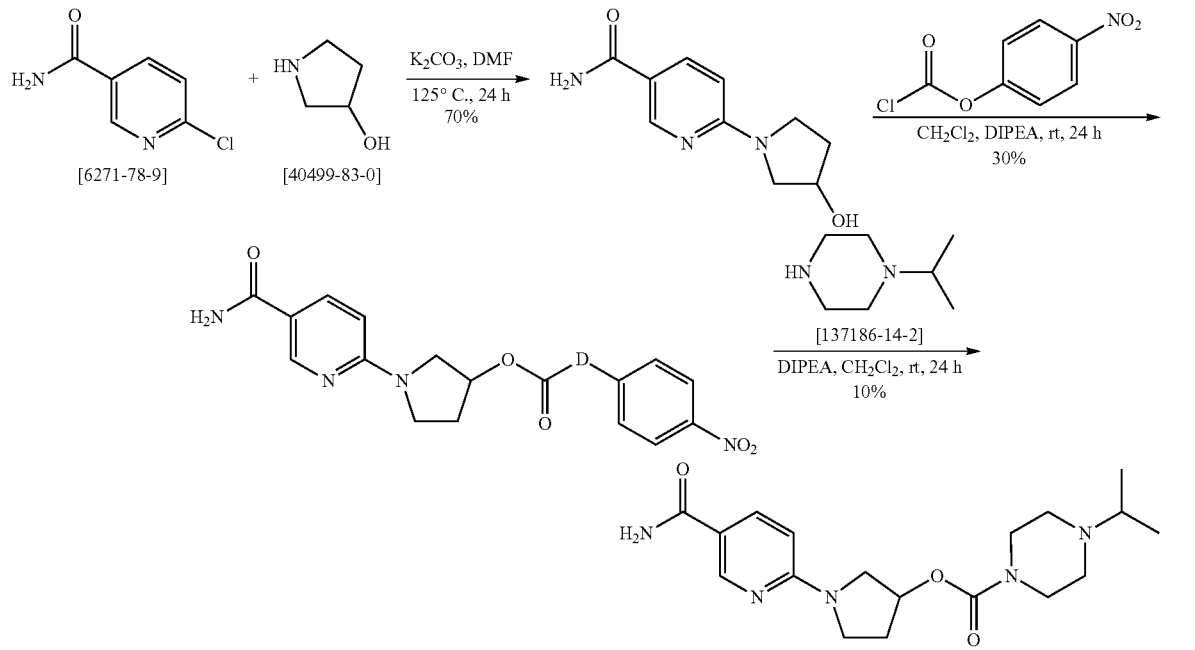

To a solution of 6-(3-hydroxypyrrolidin-1-yl)nicotinamide (0.27 g, 1 mmol) in DCM (5 ml) was added 4-nitrophenyl carbonochloridate (0.20 g, 1 mmol). The resulting solution was stirred under N$_2$ at room temperature for 24 h. The reaction mixture was then filtered and the filter cake was washed with DCM. The combined filtrates were concentrated to afford the title compound (0.11 g, 30%) as a yellow liquid. [LCMS Rt$_A$=1.71 min, [M+H]$^+$=373.1].

c) 1-(5-carbamoylpyridin-2-yl)pyrrolidin-3-yl 4-isopropylpiperazine-1-carboxylate

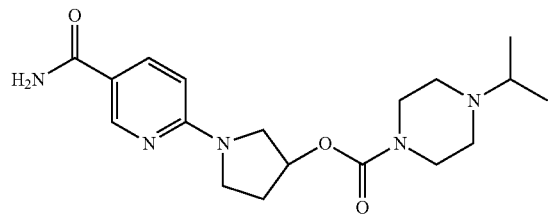 [SMILES: CC(C)N1CCN(C(=O)OC2CCN(c3ccc(C(N)=O)cn3)C2)CC1]

To a solution of 1-(5-carbamoylpyridin-2-yl)-pyrrolidin-3-yl 4-nitrophenyl carbonate (0.37 g, 1 mmol) in DCM (5 ml) was added 1-isopropylpiperazine (0.13 g, 1 mmol). The resulting solution was stirred under N$_2$ at room temperature for 24 h. The reaction mixture was then filtered and the filter cake was washed with DCM. The combined filtrates were concentrated to afford the crude product. After further purified by preparative HPLC, the title compound was obtained as a yellow solid (36 mg, 10%). [$^1$H NMR (500 MHz, CDCl$_3$) δ8.60 (d, 1H), 7.94 (dd, 1H), 7.72 (s, 1H), 7.09 (s, 1H), 6.48 (d, 1H), 5.25 (s, 1H), 3.66 (m, 2H), 3.55 (m, 2H), 3.31 (m, 4H), 2.63 (m, 1H), 2.36 (m, 4H), 2.21 (m, 1H), 2.10 (m, 1H), 0.92 (d, 6H, J=6.5 Hz); LCMS Rt$_A$=1.58 min, [M+H]$^+$=362.2].

Example 3.1

1-(5-carbamoylpyridin-2-yl)-azetidin-3-yl 4-isopropylpiperazine-1-carboxylate (Method C)

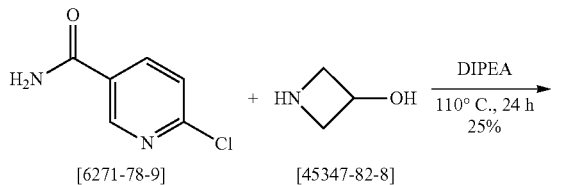

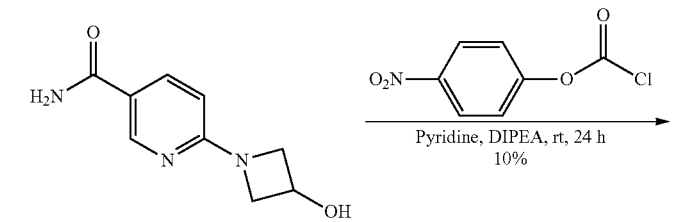

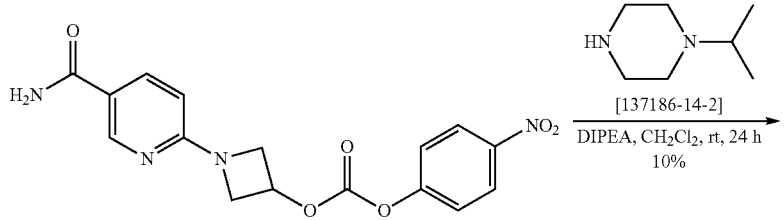

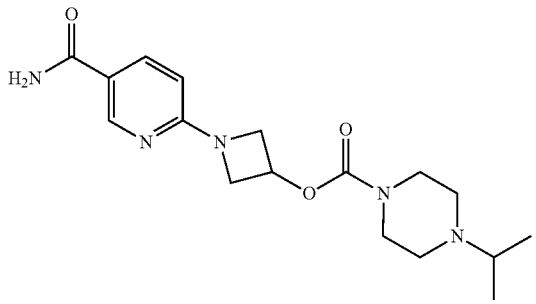

a) 6-(3-hydroxyazetidin-1-yl)nicotinamide

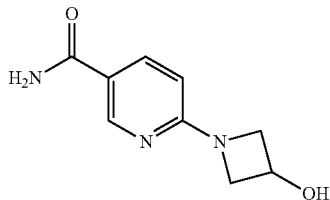 [SMILES: NC(=O)c1ccc(N2CC(O)C2)nc1]

To a solution of 6-chloronicotinamide (0.16 g, 1 mmol) and azetidin-3-ol (73 mg, 1 mmol) in DMF (5 ml) under nitrogen was added K$_2$CO$_3$ (0.41 g, 3 mmol). The resulting solution was stirred under nitrogen at 125° C. for 24 h. After all the starting materials were consumed, the reaction mixture was allowed to cool to ambient temperature. The reaction mixture was then filtered and the filter cake was washed with ethyl acetate. The combined filtrates were concentrated to afford the title compound (50 mg, 25%) as a yellow solid. [LCMS Rt$_A$=0.81 min, [M+H]$^+$=194.1].

b) 1-(5-carbamoylpyridin-2-yl)-azetidin-3-yl 4-nitrophenyl carbonate

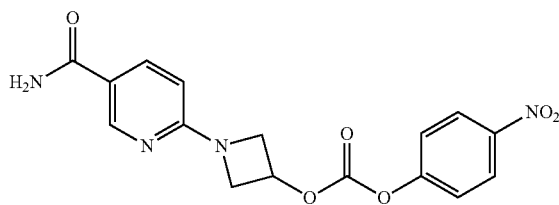 [SMILES: NC(=O)c1ccc(N2CC(OC(=O)Oc3ccc([N+](=O)[O-])cc3)C2)nc1]

To a solution of 6-(3-hydroxyazetidin-1-yl)nicotinamide (0.19 g, 1 mmol) in DCM (5 mL) under nitrogen was added 4-nitrophenyl carbonochloridate (0.20 g, 1 mmol). The resulting solution was stirred under N$_2$ at room temperature for 24 h. The reaction mixture was then filtered and the filter cake was washed with DCM. The combined filtrates were concentrated to afford the title compound (36 mg, 10%) as a yellow liquid. [LCMS Rt$_A$=1.71 min, [M+H]$^+$=359.0].

c) 1-(5-carbamoylpyridin-2-yl)azetidin-3-yl 4-isopropylpiperazine-1-carboxylate

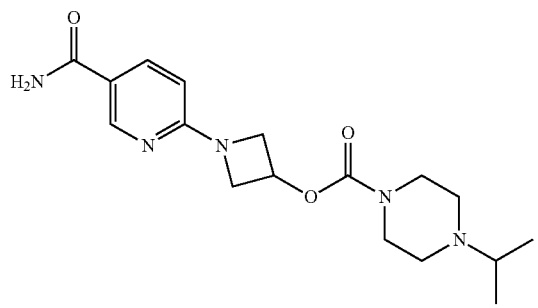 [SMILES: CC(C)N1CCN(C(=O)OC2CN(c3ccc(C(N)=O)cn3)C2)CC1]

To a solution of 1-(5-carbamoylpyridin-2-yl)-azetidin-3-yl 4-nitrophenyl carbonate (0.36 g, 1 mmol) in DCM (5 mL) under nitrogen was added 1-isopropylpiperazine (0.13 g, 1 mmol). The resulting solution was stirred under N$_2$ at room temperature for 24 h. The reaction mixture was then filtered and the filter cake was washed with DCM. The combined filtrates were concentrated to afford the crude product. After further purified by preparative HPLC, the title compound (35 mg, 10%) was obtained as a yellow solid. [$^1$HNMR (500 MHz, CDCl$_3$) δ8.58 (d, 1H), 7.96 (dd, 1H), 7.76 (s, 1H), 7.77 (s, 1H), 7.15 (s, 1H), 6.41 (d, 1H), 5.21 (m, 1H), 4.32 (m, 2H), 3.92 (m, 2H), 3.41 (m, 4H), 2.65 (m, 1H), 2.40 (m, 4H), 0.95 (d, 6H); LCMS Rt$_A$=1.59 min, [M+H]$^+$=348.2].

Example 4.1

N-(1-(5-carbamoylpyridin-2-yl)piperidin-4-yl)-4-isopropylpiperazine-1-carboxamide (Method D)

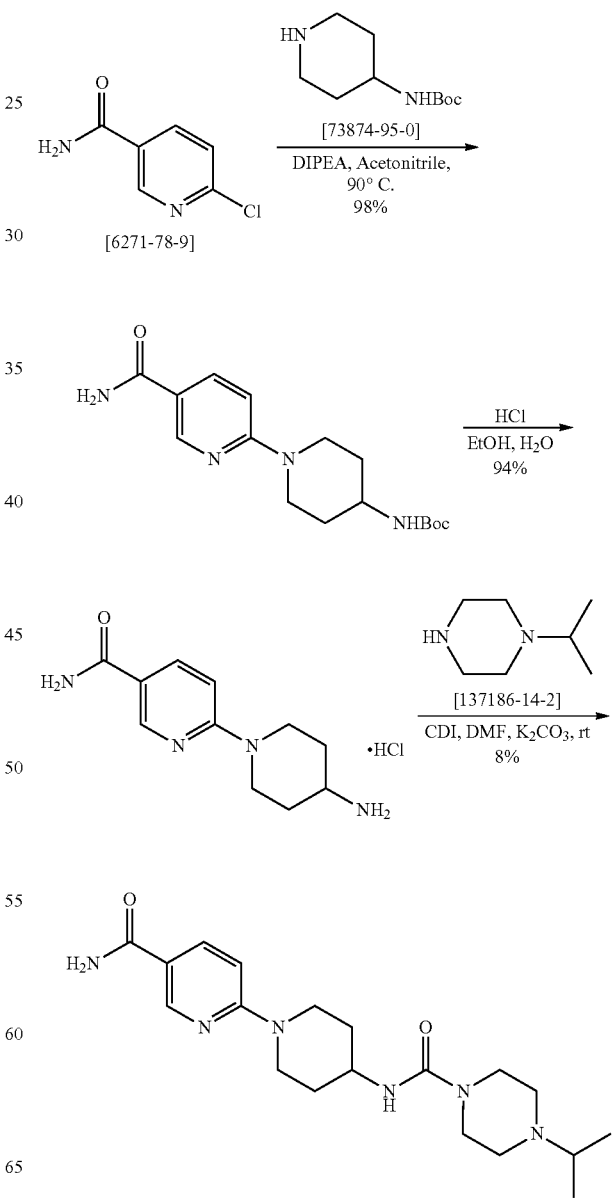

a) tert-butyl 1-(5-carbamoylpyridin-2-yl)piperidin-4-ylcarbamate

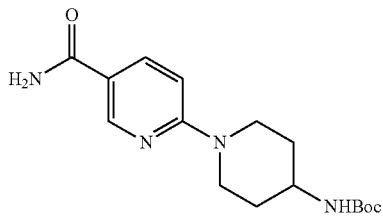 [SMILES: CC(C)(C)OC(=O)NC1CCN(c2ccc(C(N)=O)cn2)CC1]

To a stirred solution of 6-chloronicotinamide (200 mg, 1.28 mmol) in CH$_3$CN (5 ml) was added 4-N-Boc-piperidinamine (270 mg, 1.34 mmol) and DIPEA (530 mg, 3.83 mmol). The reaction mixture was stirred at reflux for 48 h. The solid was collected by filtration and washed with CH$_3$CN. After drying in vacuo, the title compound was obtained as a white solid (400 mg, 98%). [LCMS Rt$_A$=1.71 min, [M+H]$^+$=321].

b) 6-(4-aminopiperidin-1-yl)nicotinamide hydrochloride

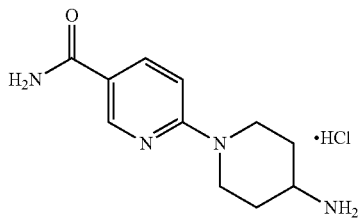 [SMILES: NC(=O)c1ccc(N2CCC(N)CC2)nc1 ; Cl]

To a stirred solution of HCl/EtOAc (9 ml, 3N) was added tert-butyl 1-(5-carbamoylpyridin-2-yl)piperidin-4-ylcarbamate (400 mg) and the mixture was stirred at room temperature for 4 h. The solid was collected by filtration and washed with EtOAc to give a white solid (300 mg, 94%). [LCMS Rt$_A$=0.85 min, [M+H]$^+$=221.1].

c) N-(1-(5-carbamoylpyridin-2-yl)piperidin-4-yl)-4-isopropylpiperazine-1-carboxamide

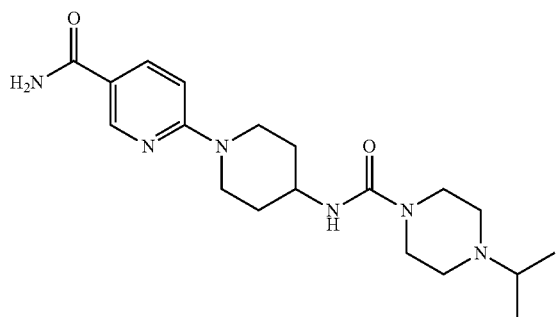 [SMILES: CC(C)N1CCN(C(=O)NC2CCN(c3ccc(C(N)=O)cn3)CC2)CC1]

To a cooled solution (0-5° C.) of 6-(4-aminopiperidin-1-yl)nicotinamide hydrochloride (293 mg, 1 mmol) in 5 ml DMF was added DIPEA (645 mg, 2.2 mmol) and 1,1'-carbonyldiimidazole (170 mg, 1.05 mmol). After stirring for 1 h, 1-isopropylpiperazine (154 mg, 1.2 mmol) was added and the resulting mixture was warmed to room temperature for 16 h. The crude mixture was filtered through Celite and the filtrate was purified by preparative HPLC to give title compound (30 mg, 8%) as an off-white solid. [$^1$HNMR (400 MHz, DMSO-d6) δ 8.60 (d, 1H), 7.94 (m, 1H), 7.73 (s, 1H), 7.10 (s, 1H), 6.86 (d, 1H), 6.21 (d, 1H), 4.37 (d, 2H), 3.65 (m, 1H), 3.23 (t, 4H), 2.94 (t, 2H) 2.62 (m, 1H), 2.34 (t, 4H), 1.78 (d, 2H), 1.36 (m, 2H), 0.96 (d, 6H); LCMS Rt$_B$=1.53 min, [M+H]$^+$=375.2].

Example 1.18

1-(5-(hydroxymethyl)pyridin-2-yl)piperidin-4-yl 4-isopropyl pipera-zine-1-carboxylate (Method E)

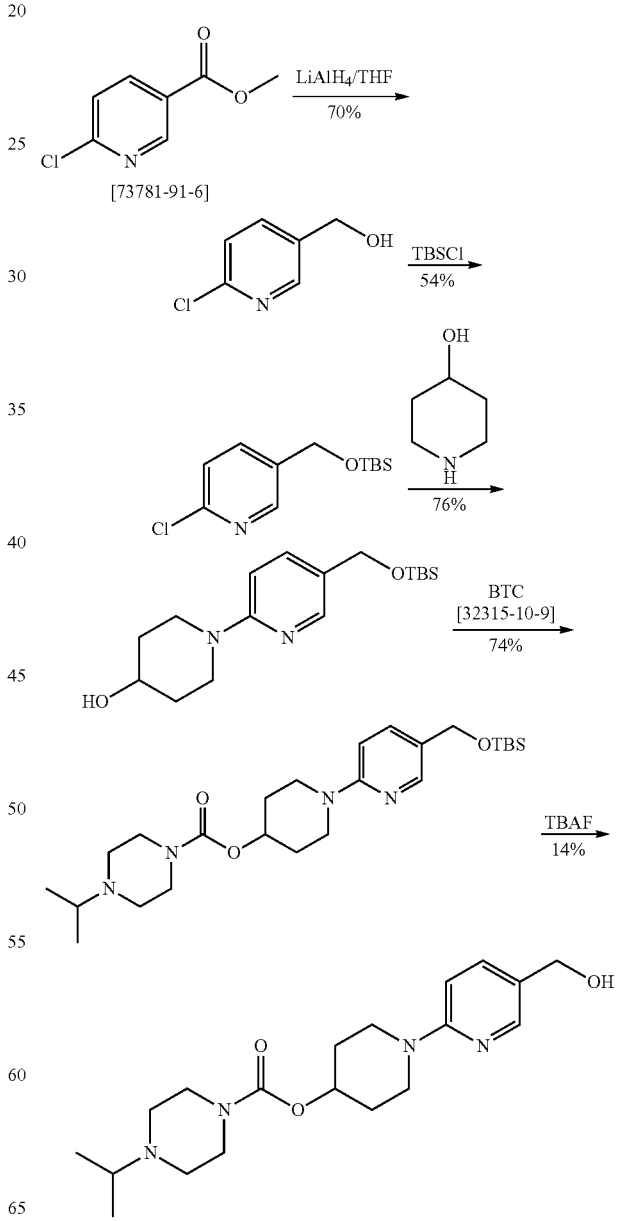

a) (6-chloropyridin-3-yl)methanol

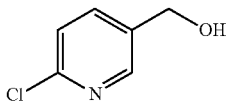

To a suspension of LiAlH$_4$ (1.5 g, 40 mmol) in THF (80 mL) was added methyl 6-chloronicotinate (1.56 g, 10 mmol) slowly at 0-5□ under N$_2$ atmosphere. The reaction mixture was stirred at rt for 3 h before it was quenched with 15% NaOH and water. The mixture was filtered through Celite® and the cake was washed with EtOAc (100 mL×3). The filtrate was washed with brine (200 mL), dried and concentrated to give the desired product as yellow oil (1 g, 70%). [LCMS: Rt$_A$=0.88 min, m/z 144.2 [M+H]$^+$].

b) 5-((tert-butyldimethylsilyloxy)methyl)-2-chloropyridine

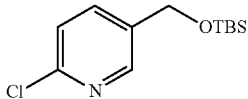

A solution of (6-chloropyridin-3-yl)methanol (800 mg, 5.6 mmol) and TBSCl (1000 mg, 6.7 mmol) in THF (15 mL) was added imidazole (455 mg, 6.7 mmol) and the reaction mixture was stirred at rt for 24 h. The mixture was concentrated under vacuum to about ¼ of the original volume and then diluted with EtOAc (30 mL). The resulting mixture was washed with water, aqueous 5% KH$_2$PO$_4$ (30 mL), saturated NaHCO$_3$ (20 mL) and brine (20 mL) sequentially. The organic phase was dried, filtered and concentrated to give the desired product as colorless oil (800 mg, 54%). [LCMS: Rt$_A$=1.89 min, m/z 258.2 [M+H]$^+$].

c) 1-(5-((tert-butyldimethylsilyloxy)methyl)pyridin-2-yl)piperidin-4-ol

A mixture of 5-((tert-butyldimethylsilyloxy)methyl)-2-chloropyridine (650 mg, 2.5 mmol) in toluene (20 mL) was degassed with argon for 5 min, followed by adding piperidin-4-ol (303 mg, 3 mmol), t-BuOK (426 mg, 3.8 mmol), Pd$_2$(dba)$_3$ (23 mg, 0.0025 mmol) and BINAP (31 mg, 0.05 mmol). The resulting mixture was stirred at 90□ overnight under argon atmosphere. After cooling to rt, solid was removed by filtration and the filtrate was concentrated to dryness. The residue was dissolved in EtOAc (50 mL) and the mixture was washed with brine (50 mL), dried and concentrated to yield the desired product as dark oil (620 mg, 76%). [LCMS: Rt$_A$=1.59 min, m/z 323.2 [M+H]$^+$].

d) 1-(5-((tert-butyldimethylsilyloxy)methyl)pyridin-2-yl)piperidin-4-yl-4-isopropyl-piperazine-1-carboxylate

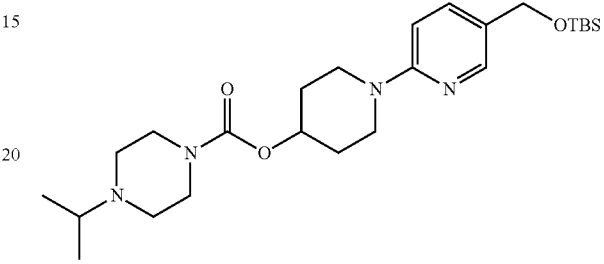

To a solution of 1-(5-((tert-butyldimethylsilyloxy)methyl)pyridin-2-yl)-piperidin-4-ol (257 mg, 1 mmol) in DCM (8 mL) was added BTC (297 mg, 1 mmol) and Et$_3$N (152 mg, 1.5 mmol). The mixture was stirred at rt for 1 h before 1-isopropylpiperazine (128 mg, 1 mmol) was added and the resulting mixture was stirred at rt overnight. The mixture was diluted with DCM (20 mL), washed with saturated K$_2$CO$_3$ (20 mL) solution and brine (20 mL), dried and concentrated to give the desired product as yellow oil (350 mg, 74%). [LCMS: Rt$_A$=1.95 min, m/z 477.2 [M+H]$^+$].

e) 1-(5-(hydroxymethyl)pyridin-2-yl)piperidin-4-yl 4-isopropylpiperazine-1-carboxylate

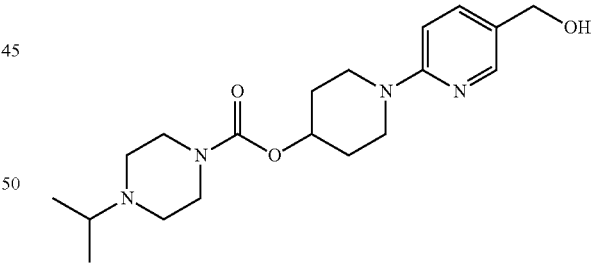

To a solution of 1-(5-((tert-butyldimethylsilyloxy)methyl)pyridin-2-yl)-piperidin-4-yl-4-isopropylpiperazine-1-carboxylate (476 mg, 1 mmol) in DCM (30 mL) was added TBAF in THF (4 mmol, 2 mL) and the mixture was stirred at rt for 48 h. The mixture was washed with brine (20 mL), dried and concentrated. The residue was purified by preparative TLC (MeOH/DCM=1/10) to give the desired product as a yellow solid (50 mg, 14%). $^1$H NMR (400 MHz, MeOD-d4): δ 8.09 (d, J=2.4 Hz, 1H) 7.61 (dd, 1H), 6.89 (d, J=8.8 Hz, 1H), 4.91 (m, 1H), 4.50 (s, 2H), 3.84 (m, 2H), 3.43~3.52 (m, 6H), 2.74 (m, 1H), 2.52 (m, 4H), 2.00 (m, 2H), 1.74 (m, 2H), 1.11 (d, J=6.4 Hz, 6H). [LCMS: Rt$_A$=1.4 min, m/z 363.2 [M+H]$^+$].

Example 2.4

1-(6-carbamoylpyridin-3-yl)pyrrolidin-3-yl 4-isopropylpiperazine-1-carboxylate (Method F)

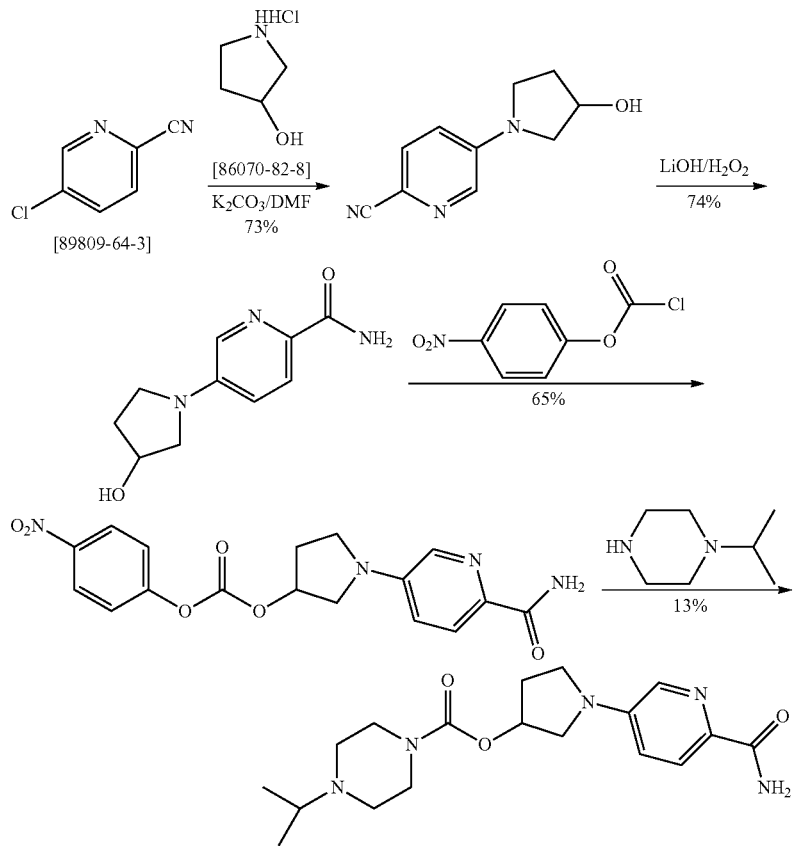

a) 5-(3-hydroxypyrrolidin-1-yl)picolinonitrile

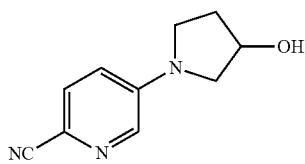 [SMILES: N#Cc1ccc(N2CCC(O)C2)cn1]

A mixture of 5-chloropicolinonitrile (2 g, 14.4 mmol), pyrrolidin-3-ol hydrochloride (2 g, 25.9 mmol) and $K_2CO_3$ (4 g, 28.9 mmol) in DMF (15 mL) was stirred at 140□ for 16 h. The organic solvent was removed under vacuum and the residue was taken into DCM (200 mL). Solid was removed by filtration and the filtrate was concentrated to give crude product (2.0 g yield 73%) as a yellow solid. [LCMS: $Rt_A$=1.19 min, m/z 190.2 [M+H]⁺].

b) 5-(3-hydroxypyrrolidin-1-yl)picolinamide

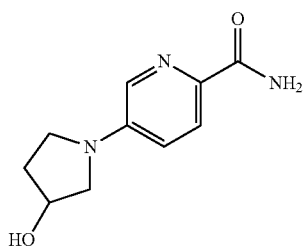 [SMILES: NC(=O)c1ccc(N2CCC(O)C2)cn1]

A mixture of 5-(3-hydroxypyrrolidin-1-yl)picolinonitrile (2.7 g, 14.3 mmol) in $H_2O_2$ (30 mL) was added $LiOH·H_2O$ (1.8 g, 42.9 mmol) and the mixture was stirred at rt for 16 h. The precipitate was collected by filtration and the cake was washed with water (20 mL) to give the desired product (2.2 g, 74%) as a yellow solid. [LCMS: $Rt_A$=1.05 min, m/z 208.2 [M+H]⁺].

c) 1-(6-carbamoylpyridin-3-yl)pyrrolidin-3-yl 4-nitrophenyl carbonate

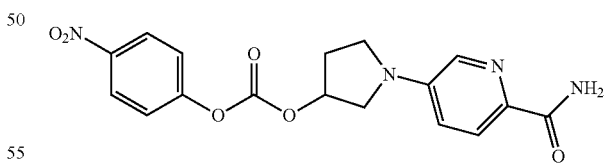

To a solution of 5-(3-hydroxypyrrolidin-1-yl)picolinamide (1 g, 4.83 mmol) and 4-nitrophenyl carbonochloridate (1.46 g, 8.3 mmol) in pyridine (30 mL) was added DIPEA (1.25 g, 11 mmol) and the resulting mixture was stirred at rt for 3 days. The precipitate was collected by filtration and the cake was washed with DCM (20 mL) to give the desired compound (1.0 g, 56%) as a pale yellow solid. [LCMS: $Rt_A$=1.48 min, m/z 373.2 [M+H]⁺].

d) 1-(6-carbamoylpyridin-3-yl)pyrrolidin-3-yl 4-isopropylpiperazine-1-carboxylate

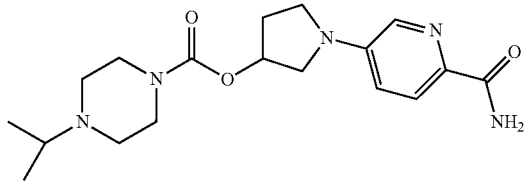 [SMILES: CC(C)N1CCN(C(=O)OC2CCN(c3ccc(C(N)=O)nc3)C2)CC1]

To a solution of 1-(6-carbamoylpyridin-3-yl)pyrrolidin-3-yl-4-nitrophenyl carbonate (171 mg, 0.46 mmol) and 1-isopropylpiperazine (62 mg, 0.48 mmol) in pyridine (5 mL) was added DIPEA (118 mg, 0.92 mmol) and the resulting mixture was stirred at rt for 2 h. The mixture was concentrated to dryness and the residue was purified by preparative TLC (MeOH/DCM=1/10) to give the desired compound (20 mg, 13%) as a pale yellow solid. $^1$HNMR (400 MHz, MeOD): δ 7.96 (m, 2H) 7.01 (m, 1H), 5.39 (s, 1H), 3.70 (m, 1H), 3.46~3.55 (m, 7H), 2.69 (m, 1H), 2.50 (br, 4H), 2.29 (m, 2H), 1.06 (d, J=6.4, 6H). [LCMS: $Rt_A$=1.33 min, m/z 362.2 [M+H]$^+$].

Table 1 shows compounds of formula (I). Examples 1.1 to 1.17, 1.19-1.31, 1.33-1.54 and 1.56-1.95 were synthesized according to Method A; Examples 2.1 to 2.3 were synthesized according to Method B; Examples 3.1 to 3.3 were synthesized according to Method C; Example 4.1 was synthesized according to Method D; Examples 1.18, 1.32 and 1.55 were synthesized according to Method E; and Example 2.4 was synthesized according to Method F.

TABLE 1

| Ex. | Structure | Name | LCMS Rt [min], method | [M + H]$^+$ |
|---|---|---|---|---|
| 1.1 | 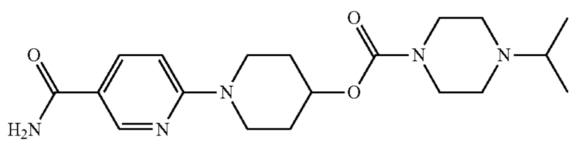 | 1-(5-carbamoylpyridin-2-yl)piperidin-4-yl 4-isopropylpiperazine-1-carboxylate | 1.61(A) | 376.3 |
| 1.2 | 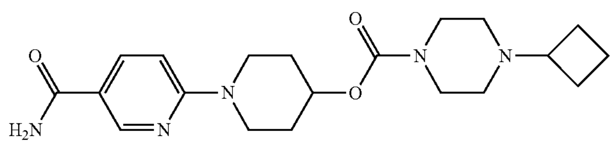 [SMILES: NC(=O)c1ccc(N2CCC(OC(=O)N3CCN(C4CCC4)CC3)CC2)nc1] | 1-(5-carbamoylpyridin-2-yl)piperidin-4-yl 4-cyclobutylpiperazine-1-carboxylate | 1.65(A) | 388.3 |
| 1.3 | 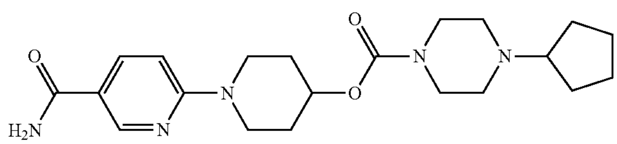 | 1-(5-carbamoylpyridin-2-yl)piperidin-4-yl 4-cyclopentylpiperazine-1-carboxylate | 1.71(A) | 402.2 |
| 1.4 | 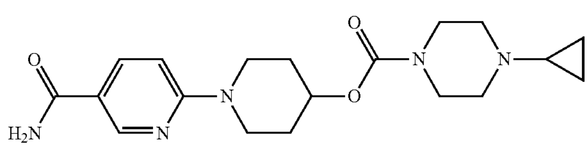 [SMILES: NC(=O)c1ccc(N2CCC(OC(=O)N3CCN(C4CC4)CC3)CC2)nc1] | 1-(5-carbamoylpyridin-2-yl)piperidin-4-yl 4-cyclopropylpiperazine-1-carboxylate | 1.63(A) | 374.2 |
| 1.5 | 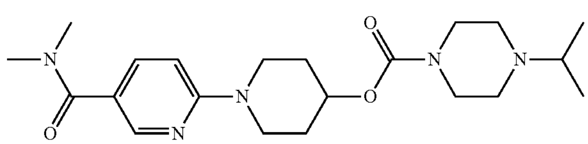 [SMILES: CC(C)N1CCN(C(=O)OC2CCN(c3ccc(C(=O)N(C)C)cn3)CC2)CC1] | 1-(5-(dimethylcarbamoyl)pyridin-2-yl)piperidin-4-yl 4-isopropylpiperazine-1-carboxylate | 1.62(B) | 404.1 |
| 1.6 | 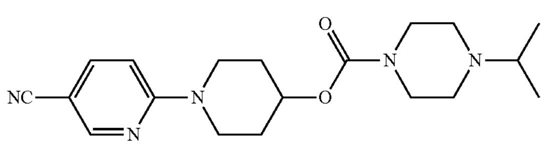 [SMILES: CC(C)N1CCN(C(=O)OC2CCN(c3ccc(C#N)cn3)CC2)CC1] | 1-(5-cyanopyridin-2-yl)piperidin-4-yl 4-isopropylpiperazine-1-carboxylate | 1.53(C) | 358.1 |
| 1.7 | 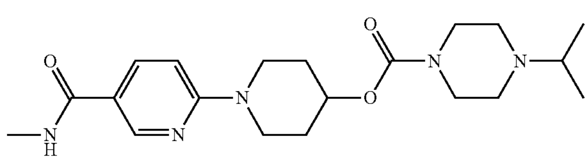 [SMILES: CNC(=O)c1ccc(N2CCC(OC(=O)N3CCN(C(C)C)CC3)CC2)nc1] | 1-(5-(methylcarbamoyl)pyridin-2-yl)piperidin-4-yl 4-isopropylpiperazine-1-carboxylate | 1.66(A) | 390.2 |

TABLE 1-continued

| Ex. | Structure | Name | LCMS Rt [min], method | [M + H]+ |
|---|---|---|---|---|
| 1.8 | 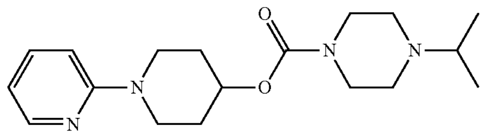 [SMILES: CC(C)N1CCN(C(=O)OC2CCN(c3ccccn3)CC2)CC1] | 1-(pyridin-2-yl)piperidin-4-yl 4-isopropylpiperazine-1-carboxylate | 1.88(A) | 333.2 |
| 1.9 | 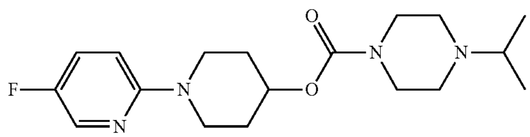 [SMILES: CC(C)N1CCN(C(=O)OC2CCN(c3ccc(F)cn3)CC2)CC1] | 1-(5-fluoropyridin-2-yl)piperidin-4-yl 4-isopropylpiperazine-1-carboxylate | 1.95(A) | 351.2 |
| 1.10 | 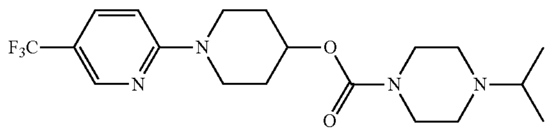 [SMILES: CC(C)N1CCN(C(=O)OC2CCN(c3ccc(C(F)(F)F)cn3)CC2)CC1] | 1-(5-(trifluoromethyl)pyridin-2-yl)piperidin-4-yl 4-isopropylpiperazine-1-carboxylate | 2.09(A) | 401.2 |
| 1.11 | 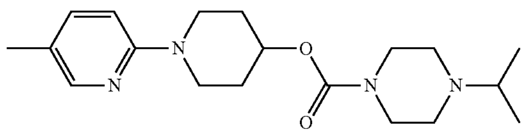 [SMILES: Cc1ccc(N2CCC(OC(=O)N3CCN(C(C)C)CC3)CC2)nc1] | 1-(5-methylpyridin-2-yl)piperidin-4-yl 4-isopropylpiperazine-1-carboxylate | 1.96(A) | 347.2 |
| 1.12 | 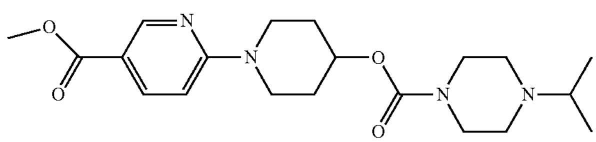 [SMILES: COC(=O)c1ccc(N2CCC(OC(=O)N3CCN(C(C)C)CC3)CC2)nc1] | 1-(5-(methoxycarbonyl)pyridin-2-yl)piperidin-4-yl 4-isopropylpiperazine-1-carboxylate | 1.91(A) | 391.2 |
| 1.13 | 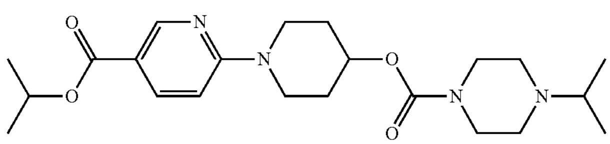 [SMILES: CC(C)OC(=O)c1ccc(N2CCC(OC(=O)N3CCN(C(C)C)CC3)CC2)nc1] | 1-(4-(isopropoxycarbonyl)pyridin-2-yl)piperidin-4-yl 4-isopropylpiperazine-1-carboxylate | 2.05(A) | 419.2 |
| 1.14 | 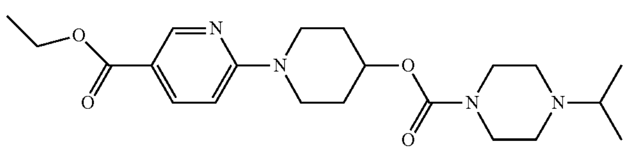 [SMILES: CCOC(=O)c1ccc(N2CCC(OC(=O)N3CCN(C(C)C)CC3)CC2)nc1] | 1-(5-(ethoxycarbonyl)pyridin-2-yl)piperidin-4-yl 4-isopropylpiperazine-1-carboxylate | 1.99(A) | 405.2 |
| 1.15 | 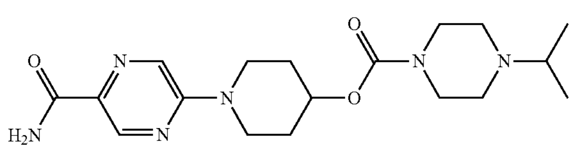 [SMILES: CC(C)N1CCN(C(=O)OC2CCN(c3cnc(C(N)=O)cn3)CC2)CC1] | 1-(5-carbamoylpyrazin-2-yl)piperidin-4-yl 4-isopropylpiperazine-1-carboxylate | 1.66(A) | 377.2 |
| 1.16 | 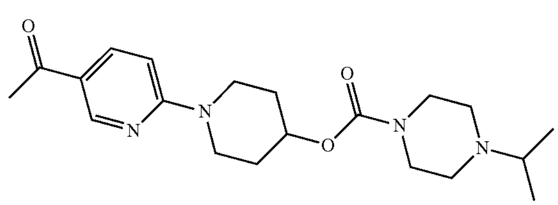 [SMILES: CC(=O)c1ccc(N2CCC(OC(=O)N3CCN(C(C)C)CC3)CC2)nc1] | 1-(5-acetylpyridin-2-yl)piperidin-4-yl 4-isopropylpiperazine-1-carboxylate | 1.82(A) | 375.2 |
| 1.17 | 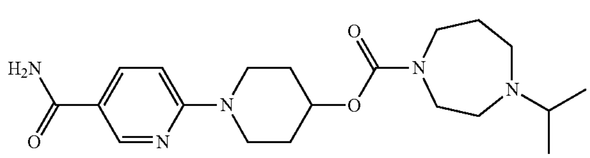 [SMILES: CC(C)N1CCCN(C(=O)OC2CCN(c3ccc(C(N)=O)cn3)CC2)CC1] | 1-(5-carbamoylpyridin-2-yl)piperidin-4-yl 4-isopropyl-1,4-diazepane-1-carboxylate | 1.25(A) | 390.2 |

TABLE 1-continued

| Ex. | Structure | Name | LCMS Rt [min], method | [M + H]+ |
|---|---|---|---|---|
| 1.18 | 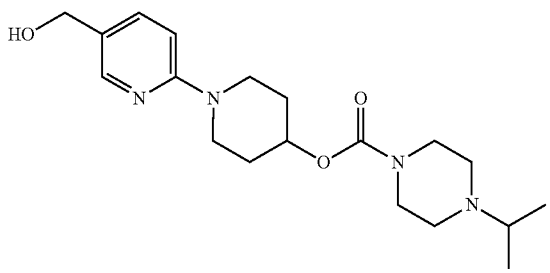 [SMILES: CC(C)N1CCN(C(=O)OC2CCN(c3ccc(CO)cn3)CC2)CC1] | 1-(5-(hydroxymethyl)pyridin-2-yl)piperidin-4-yl 4-isopropylpiperazine-1-carboxylate | 1.10(A) | 363.3 |
| 1.19 | 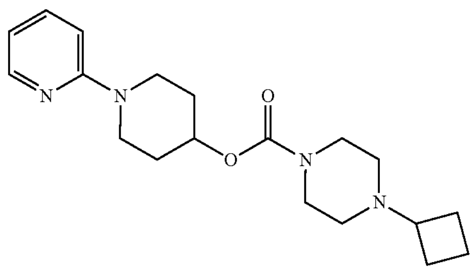 [SMILES: O=C(OC1CCN(c2ccccn2)CC1)N1CCN(C2CCC2)CC1] | 1-(pyridin-2-yl)piperidin-4-yl 4-cyclobutylpiperazine-1-carboxylate | 1.66(A) | 345.4 |
| 1.20 | 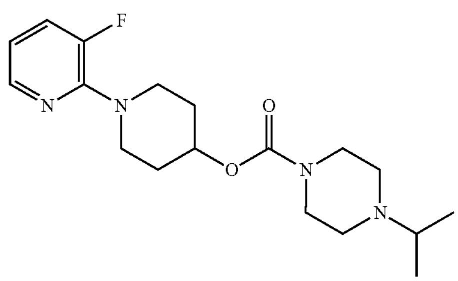 [SMILES: CC(C)N1CCN(C(=O)OC2CCN(c3ncccc3F)CC2)CC1] | 1-(3-fluoropyridin-2-yl)piperidin-4-yl 4-isopropylpiperazine-1-carboxylate | 1.65(A) | 351.2 |
| 1.21 | 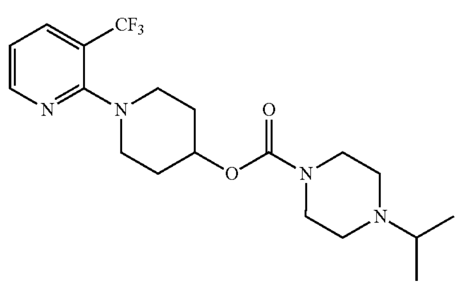 [SMILES: CC(C)N1CCN(C(=O)OC2CCN(c3ncccc3C(F)(F)F)CC2)CC1] | 1-(3-(trifluoromethyl)pyridin-2-yl)piperidin-4-yl 4-isopropylpiperazine-1-carboxylate | 1.94(A) | 400.9 |
| 1.22 | 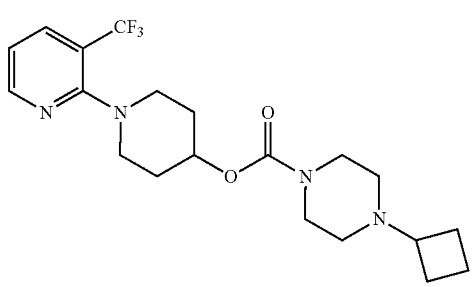 [SMILES: O=C(OC1CCN(c2ncccc2C(F)(F)F)CC1)N1CCN(C2CCC2)CC1] | 1-(3-(trifluoromethyl)pyridin-2-yl)piperidin-4-yl 4-cyclobutylpiperazine-1-carboxylate | 1.94(A) | 413.1 |

TABLE 1-continued

| Ex. | Structure | Name | LCMS Rt [min], method | [M + H]+ |
|---|---|---|---|---|
| 1.23 | 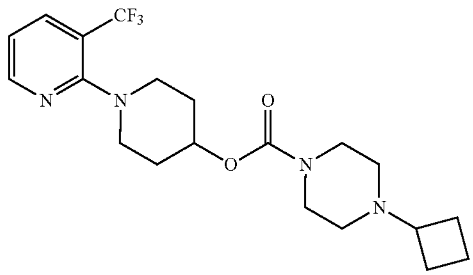 [SMILES: O=C(OC1CCN(c2ncccc2C(F)(F)F)CC1)N1CCN(C2CCC2)CC1] | 1-(3-cyanopyridin-2-yl)piperidin-4-yl 4-cyclobutylpiperazine-1-carboxylate | 1.75(A) | 370.1 |
| 1.24 | 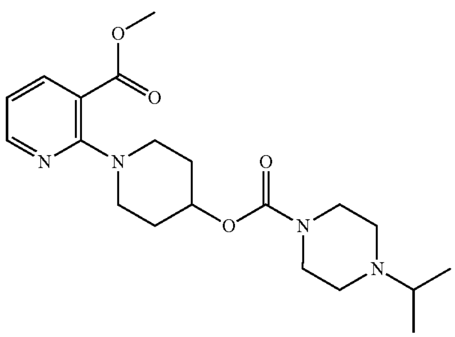 [SMILES: COC(=O)c1cccnc1N1CCC(OC(=O)N2CCN(C(C)C)CC2)CC1] | 1-(3-(methoxycarbonyl)pyridin-2-yl)piperidin-4-yl 4-isopropylpiperazine-1-carboxylate | 1.60(A) | 391.2 |
| 1.25 | 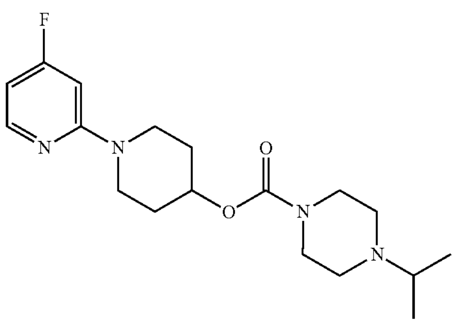 [SMILES: CC(C)N1CCN(C(=O)OC2CCN(c3cc(F)ccn3)CC2)CC1] | 1-(4-fluoropyridin-2-yl)piperidin-4-yl 4-isopropylpiperazine-1-carboxylate | 1.41(A) | 351.2 |
| 1.26 | 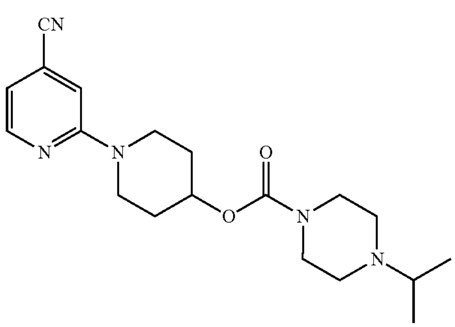 [SMILES: CC(C)N1CCN(C(=O)OC2CCN(c3cc(C#N)ccn3)CC2)CC1] | 1-(4-cyanopyridin-2-yl)piperidin-4-yl 4-isopropylpiperazine-1-carboxylate | 1.73(A) | 358.1 |
| 1.27 | 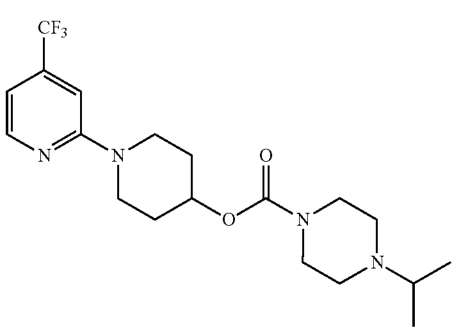 | 1-(4-(trifluoromethyl)pyridin-2-yl)piperidin-4-yl 4-isopropylpiperazine-1-carboxylate | 1.90(A) | 401 |

TABLE 1-continued

| Ex. | Structure | Name | LCMS Rt [min], method | [M + H]+ |
|---|---|---|---|---|
| 1.28 | 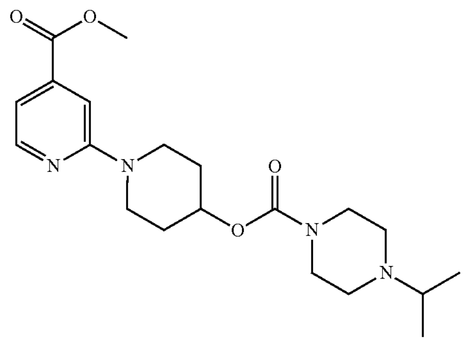 [SMILES: COC(=O)c1ccnc(N2CCC(OC(=O)N3CCN(C(C)C)CC3)CC2)c1] | 1-(4-(methoxycarbonyl)pyridin-2-yl)piperidin-4-yl 4-isopropylpiperazine-1-carboxylate | 1.40(A) | 391.2 |
| 1.29 | 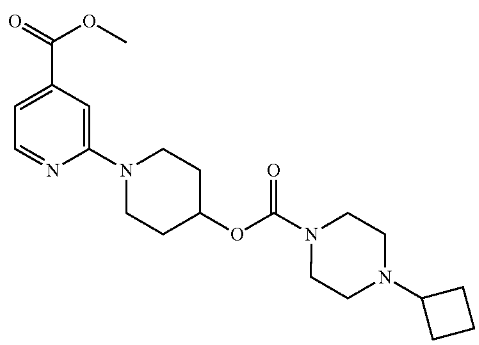 [SMILES: COC(=O)c1ccnc(N2CCC(OC(=O)N3CCN(C4CCC4)CC3)CC2)c1] | 1-(4-(methoxycarbonyl)pyridin-2-yl)piperidin-4-yl 4-cyclobutylpiperazine-1-carboxylate | 1.46(A) | 403.2 |
| 1.30 | 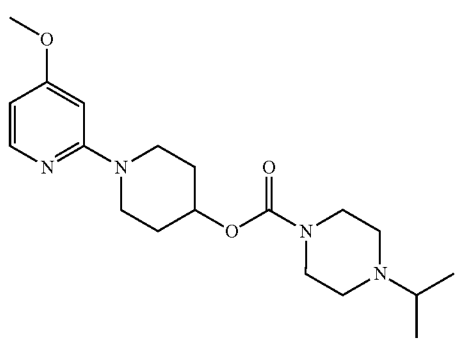 [SMILES: COc1ccnc(N2CCC(OC(=O)N3CCN(C(C)C)CC3)CC2)c1] | 1-(4-methoxypyridin-2-yl)piperidin-4-yl 4-isopropylpiperazine-1-carboxylate | 1.86(A) | 363.1 |
| 1.31 | 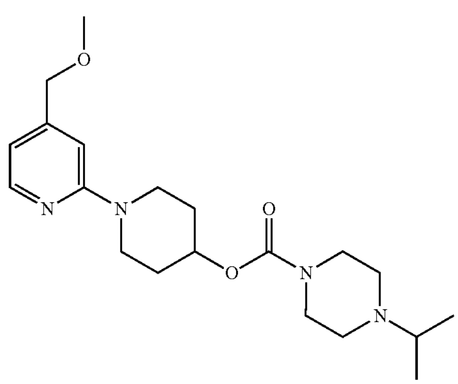 [SMILES: COCc1ccnc(N2CCC(OC(=O)N3CCN(C(C)C)CC3)CC2)c1] | 1-(4-(methoxymethyl)pyridin-2-yl)piperidin-4-yl 4-isopropylpiperazine-1-carboxylate | 1.67(A) | 377.1 |

TABLE 1-continued

| Ex. | Structure | Name | LCMS Rt [min], method | [M + H]+ |
|---|---|---|---|---|
| 1.32 | 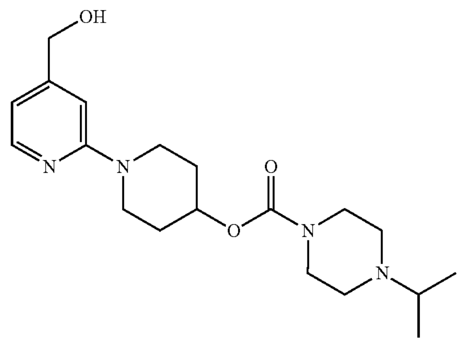 [SMILES: CC(C)N1CCN(C(=O)OC2CCN(c3cc(CO)ccn3)CC2)CC1] | 1-(4-(hydroxymethyl)pyridin-2-yl)piperidin-4-yl 4-isopropylpiperazine-1-carboxylate | 1.11(A) | 363.3 |
| 1.33 | 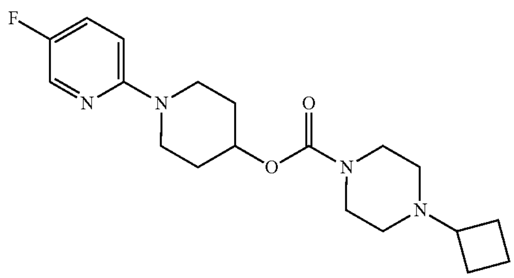 [SMILES: O=C(OC1CCN(c2ccc(F)cn2)CC1)N1CCN(C2CCC2)CC1] | 1-(5-fluoropyridin-2-yl)piperidin-4-yl 4-cyclobutylpiperazine-1-carboxylate | 1.90(A) | 363.2 |
| 1.34 | 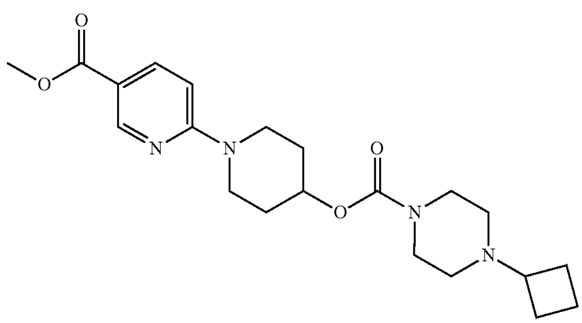 [SMILES: COC(=O)c1ccc(N2CCC(OC(=O)N3CCN(C4CCC4)CC3)CC2)nc1] | 1-(5-(methoxycarbonyl)pyridin-2-yl)piperidin-4-yl 4-cyclobutylpiperazine-1-carboxylate | 1.41(A) | 403.2 |
| 1.35 | 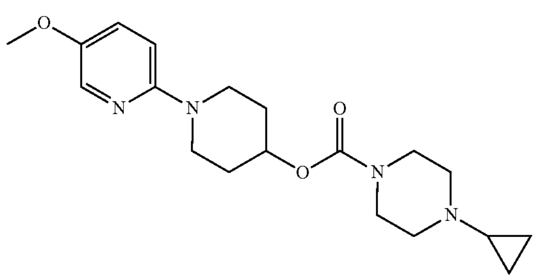 [SMILES: COc1ccc(N2CCC(OC(=O)N3CCN(C4CC4)CC3)CC2)nc1] | 1-(5-methoxypyridin-2-yl)piperidin-4-yl 4-cyclopropylpiperazine-1-carboxylate | 1.34(A) | 361.2 |
| 1.36 | 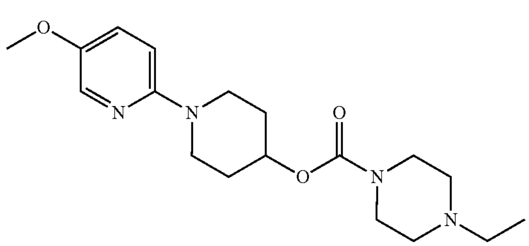 [SMILES: CCN1CCN(C(=O)OC2CCN(c3ccc(OC)cn3)CC2)CC1] | 1-(5-methoxypyridin-2-yl)piperidirv4-yl 4-ethylpiperazine-1-carboxylate | 1.81(A) | 349.2 |

TABLE 1-continued

| Ex. | Structure | Name | LCMS Rt [min], method | [M + H]+ |
|---|---|---|---|---|
| 1.37 | 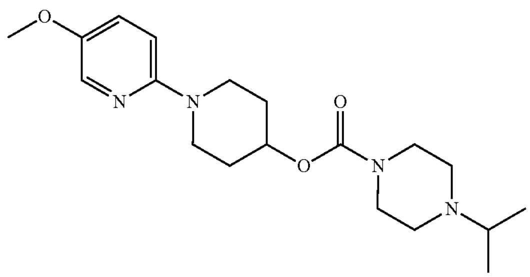 [SMILES: COc1ccc(N2CCC(OC(=O)N3CCN(C(C)C)CC3)CC2)nc1] | 1-(5-methoxypyridin-2-yl)piperidin-4-yl 4-isopropylpiperazine-1-carboxylate | 1.90(A) | 363.3 |
| 1.38 | 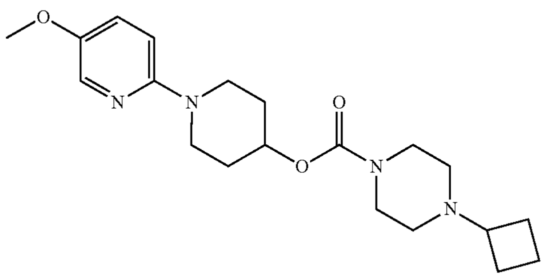 [SMILES: COc1ccc(N2CCC(OC(=O)N3CCN(C4CCC4)CC3)CC2)nc1] | 1-(5-methoxypyridin-2-yl)piperidin-4-yl 4-cyclobutylpiperazine-1-carboxylate | 2.05(A) | 375.3 |
| 1.39 | 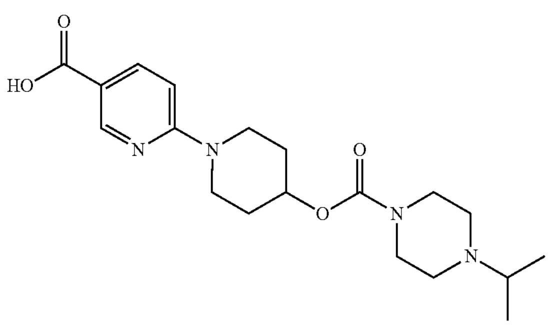 [SMILES: CC(C)N1CCN(C(=O)OC2CCN(c3ccc(C(=O)O)cn3)CC2)CC1] | 6-(4-(4-isopropylpiperazine-1-carbonyloxy)piperidin-1-yl)nicotinic acid | 1.19(A) | 377.3 |
| 1.40 | 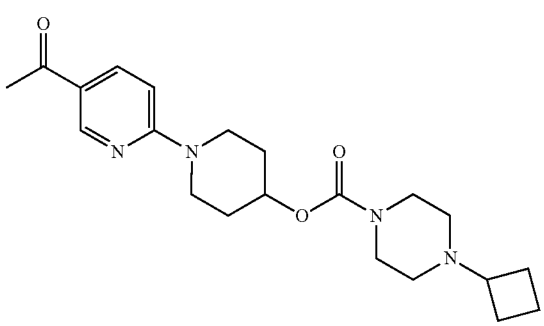 [SMILES: CC(=O)c1ccc(N2CCC(OC(=O)N3CCN(C4CCC4)CC3)CC2)nc1] | 1-(5-acetylpyridin-2-yl)piperidin-4-yl 4-cyclobutylpiperazine-1-carboxylate | 1.70(A) | 387 |
| 1.41 | 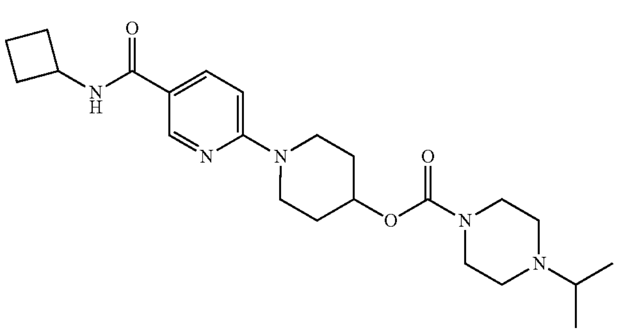 [SMILES: CC(C)N1CCN(C(=O)OC2CCN(c3ccc(C(=O)NC4CCC4)cn3)CC2)CC1] | 1-(5-(cyclobutylcarbamoyl)pyridin-2-yl)piperidin-4-yl 4-isopropylpiperazine-1-carboxylate | 1.83(A) | 430.3 |

TABLE 1-continued

| Ex. | Structure | Name | LCMS Rt [min], method | [M + H]+ |
|---|---|---|---|---|
| 1.42 | 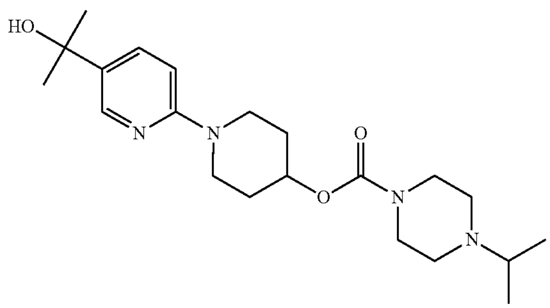 [SMILES: CC(C)N1CCN(C(=O)OC2CCN(c3ccc(C(C)(C)O)cn3)CC2)CC1] | 1-(5-(2-hydroxypropan-2-yl)pyridin-2-yl)piperidin-4-yl 4-isopropylpiperazine-1-carboxylate | 1.21(A) | 391.2 |
| 1.43 | 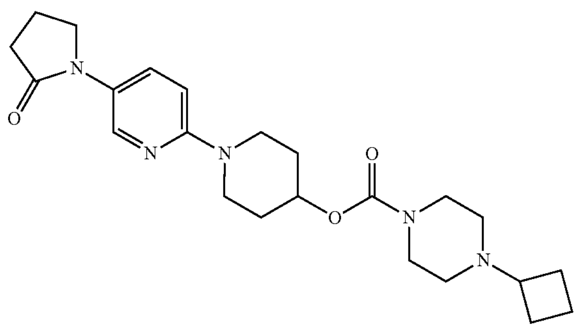 [SMILES: O=C(OC1CCN(c2ccc(N3CCCC3=O)cn2)CC1)N1CCN(C2CCC2)CC1] | 1-(5-(2-oxopyrrolidin-1-yl)pyridin-2-yl)piperidin-4-yl 4-cyclobutylpiperazine-1-carboxylate | 1.55(A) | 428.3 |
| 1.44 | 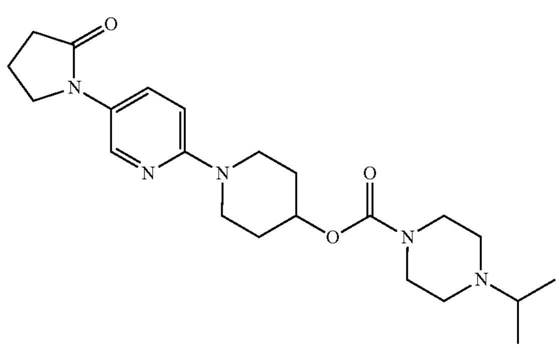 [SMILES: CC(C)N1CCN(C(=O)OC2CCN(c3ccc(N4CCCC4=O)cn3)CC2)CC1] | 1-(5-(2-oxopyrrolidin-1-yl)pyridin-2-yl)piperidin-4-yl 4-isopropylpiperazine-1-carboxylate | 1.56(A) | 416 |
| 1.45 | 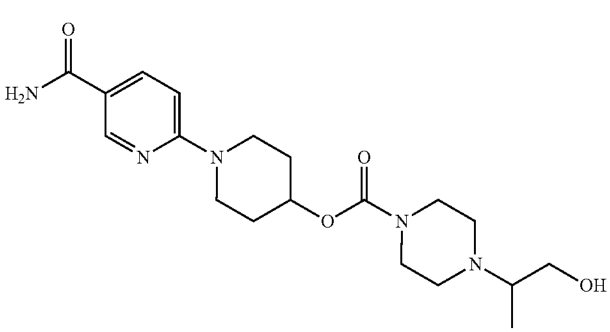 [SMILES: CC(CO)N1CCN(C(=O)OC2CCN(c3ccc(C(N)=O)cn3)CC2)CC1] | 1-(5-carbamoylpyridin-2-yl)piperidin-4-yl 4-(1-hydroxypropan-2-yl)piperazine-1-carboxylate | 0.92(A) | 392.2 |

TABLE 1-continued

| Ex. | Structure | Name | LCMS Rt [min], method | [M + H]+ |
|---|---|---|---|---|
| 1.46 | 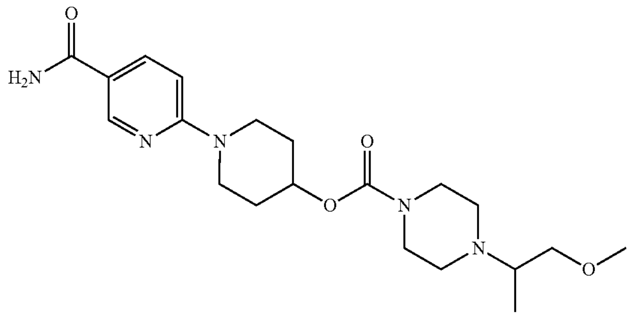 [SMILES: COCC(C)N1CCN(C(=O)OC2CCN(c3ccc(C(N)=O)cn3)CC2)CC1] | 1-(5-carbamoylpyridin-2-yl)piperidin-4-yl 4-(1-methoxypropan-2-yl)piperazine-1-carboxylate | 1.04(A) | 406.2 |
| 1.47 | 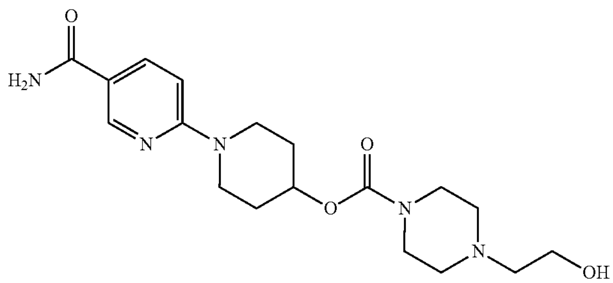 [SMILES: NC(=O)c1ccc(N2CCC(OC(=O)N3CCN(CCO)CC3)CC2)nc1] | 1-(5-carbamoylpyridin-2-yl)piperidin-4-yl 4-(2-hydroxyethyl)piperazine-1-carboxylate | 0.87(A) | 378.2 |
| 1.48 | 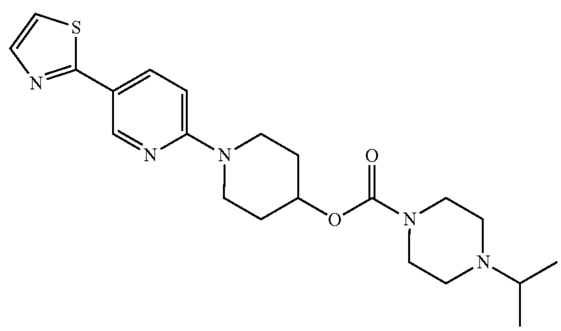 [SMILES: CC(C)N1CCN(C(=O)OC2CCN(c3ccc(-c4nccs4)cn3)CC2)CC1] | 1-(5-(thiazol-2-yl)pyridin-2-yl)piperidin-4-yl 4-isopropylpiperazine-1-carboxylate | 1.96(A) | 416.2 |
| 1.49 | 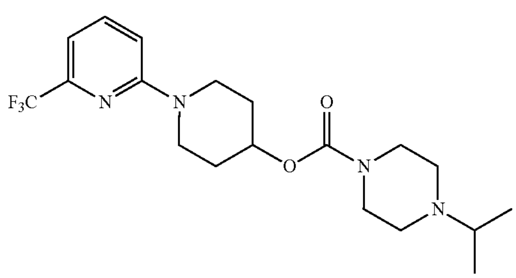 [SMILES: CC(C)N1CCN(C(=O)OC2CCN(c3cccc(C(F)(F)F)n3)CC2)CC1] | 1-(6-(trifluoromethyl)pyridin-2-yl)piperidin-4-yl 4-isopropylpiperazine-1-carboxylate | 1.96(A) | 400.9 |
| 1.50 | 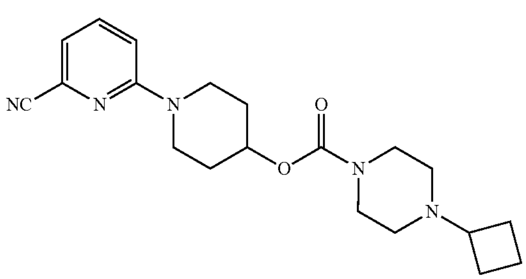 [SMILES: N#Cc1cccc(N2CCC(OC(=O)N3CCN(C4CCC4)CC3)CC2)n1] | 1-(6-cyanopyridin-2-yl)piperidin-4-yl 4-cyclobutylpiperazine-1-carboxylate | 1.43(A) | 370.2 |

TABLE 1-continued

| Ex. | Structure | Name | LCMS Rt [min], method | [M + H]+ |
|---|---|---|---|---|
| 1.51 | 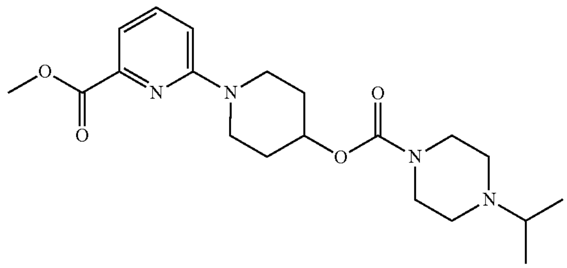 [SMILES: COC(=O)c1cccc(N2CCC(OC(=O)N3CCN(C(C)C)CC3)CC2)n1] | 1-(6-(methoxycarbonyl)pyridin-2-yl)piperidin-4-yl 4-isopropylpiperazine-1-carboxylate | 1.7(A) | 391.1 |
| 1.52 | 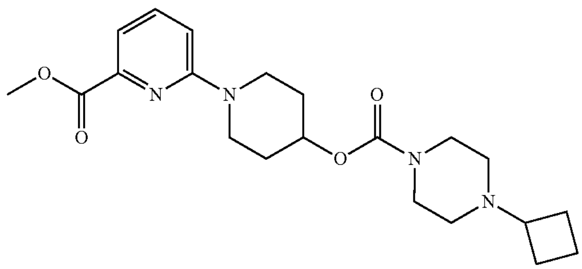 [SMILES: COC(=O)c1cccc(N2CCC(OC(=O)N3CCN(C4CCC4)CC3)CC2)n1] | 1-(6-(methoxycarbonyl)pyridin-2-yl)piperidin-4-yl 4-cyclobutylpiperazine-1-carboxylate | 1.75(A) | 403 |
| 1.53 | 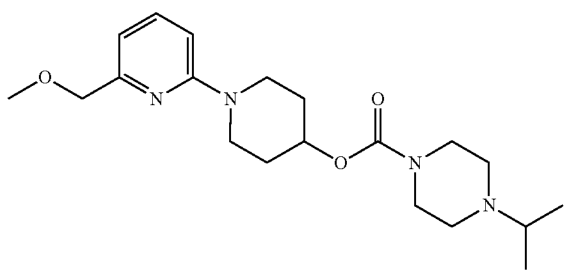 [SMILES: COCc1cccc(N2CCC(OC(=O)N3CCN(C(C)C)CC3)CC2)n1] | 1-(6-(methoxymethyl)pyridin-2-yl)piperidin-4-yl 4-isopropylpiperazine-1-carboxylate | 1.42(A) | 377.2 |
| 1.54 | 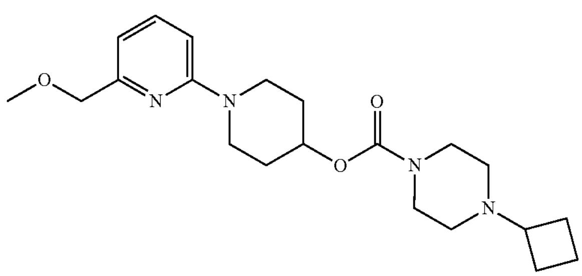 [SMILES: COCc1cccc(N2CCC(OC(=O)N3CCN(C4CCC4)CC3)CC2)n1] | 1-(6-(methoxymethyl)pyridin-2-yl)piperidin-4-yl 4-cyclobutylpiperazine-1-carboxylate | 1.81(A) | 389.2 |
| 1.55 | 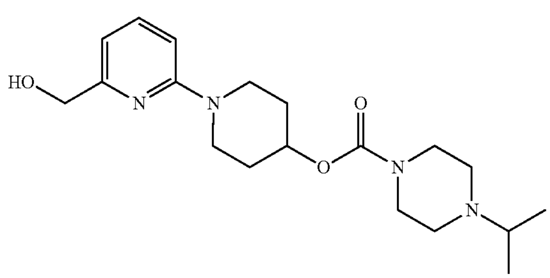 [SMILES: CC(C)N1CCN(C(=O)OC2CCN(c3cccc(CO)n3)CC2)CC1] | 1-(6-(hydroxymethyl)pyridin-2-yl)piperidin-4-yl 4-isopropylpiperazine-1-carboxylate | 1.49(A) | 363.3 |

TABLE 1-continued

| Ex. | Structure | Name | LCMS Rt [min], method | [M + H]+ |
|---|---|---|---|---|
| 1.56 | 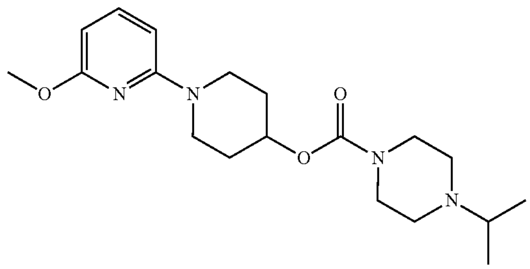 [SMILES: COc1cccc(N2CCC(OC(=O)N3CCN(C(C)C)CC3)CC2)n1] | 1-(6-methoxypyridin-2-yl)piperidin-4-yl 4-isopropylpiperazine-1-carboxylate | 1.86(A) | 363.1 |
| 1.57 | 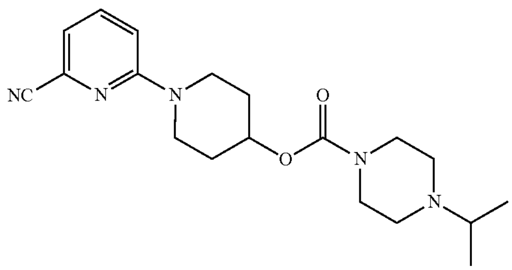 [SMILES: CC(C)N1CCN(C(=O)OC2CCN(c3cccc(C#N)n3)CC2)CC1] | 1-(6-cyanopyridin-2-yl)piperidin-4-yl 4-isopropylpiperazine-1-carboxylate | 1.75(A) | 358.1 |
| 1.58 | 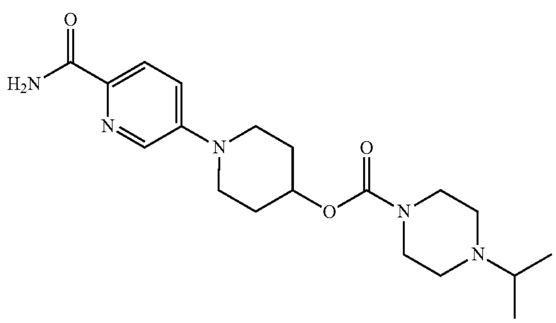 [SMILES: CC(C)N1CCN(C(=O)OC2CCN(c3ccc(C(N)=O)nc3)CC2)CC1] | 1-(6-carbamoylpyridin-3-yl)piperidin-4-yl 4-isopropylpiperazine-1-carboxylate | 1.46(A) | 376.1 |
| 1.59 | 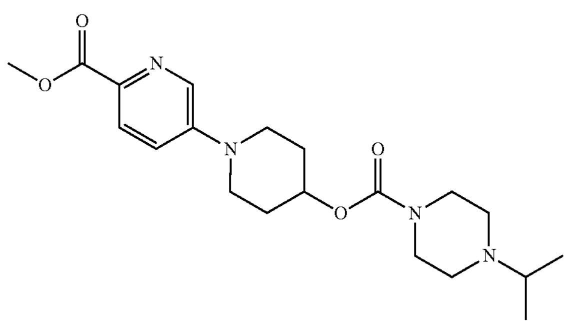 [SMILES: COC(=O)c1ccc(N2CCC(OC(=O)N3CCN(C(C)C)CC3)CC2)cn1] | 1-(6-(methoxycarbonyl)pyridin-3-yl)piperidin-4-yl 4-isopropylpiperazine-1-carboxylate | 1.45(A) | 391.3 |
| 1.60 | 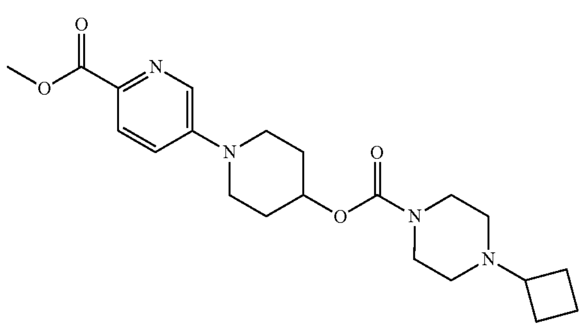 [SMILES: COC(=O)c1ccc(N2CCC(OC(=O)N3CCN(C4CCC4)CC3)CC2)cn1] | 1-(6-(methoxycarbonyl)pyridin-3-yl)piperidin-4-yl 4-cyclobutylpiperazine-1-carboxylate | 1.53(A) | 403.3 |

TABLE 1-continued

| Ex. | Structure | Name | LCMS Rt [min], method | [M + H]+ |
|---|---|---|---|---|
| 1.61 | 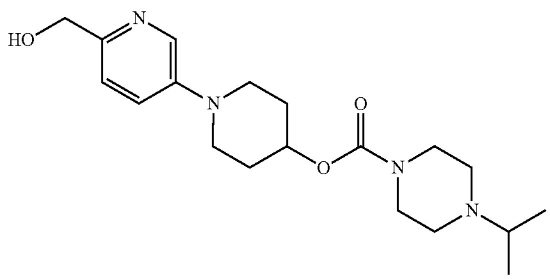 [SMILES: CC(C)N1CCN(C(=O)OC2CCN(c3ccc(CO)nc3)CC2)CC1] | 1-(6-(hydroxymethyl)pyridin-3-yl)piperidin-4-yl 4-isopropylpiperazine-1-carboxylate | 1.32(A) | 363.3 |
| 1.62 | 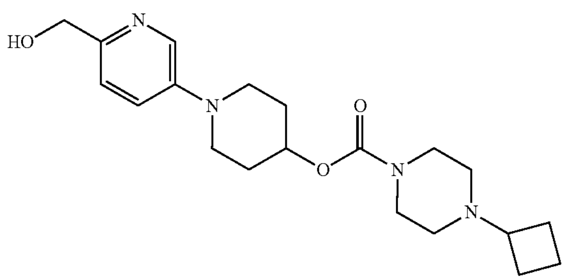 [SMILES: O=C(OC1CCN(c2ccc(CO)nc2)CC1)N1CCN(C2CCC2)CC1] | 1-(6-(hydroxymethyl)pyridin-3-yl)piperidin-4-yl 4-cyclobutylpiperazine-1-carboxylate | 1.38(A) | 375.2 |
| 1.63 | 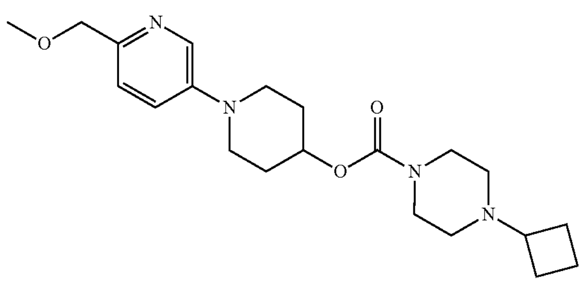 [SMILES: COCc1ccc(N2CCC(OC(=O)N3CCN(C4CCC4)CC3)CC2)cn1] | 1-(6-(methoxymethyl)pyridin-3-yl)piperidin-4-yl 4-cyclobutylpiperazine-1-carboxylate | 1.50(A) | 389.3 |
| 1.64 | 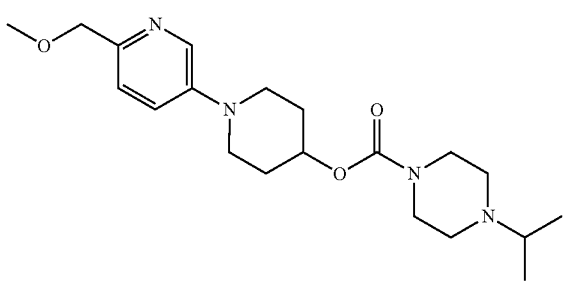 [SMILES: COCc1ccc(N2CCC(OC(=O)N3CCN(C(C)C)CC3)CC2)cn1] | 1-(6-(methoxymethyl)pyridin-3-yl)piperidin-4-yl 4-isopropylpiperazine-1-carboxylate | 1.50(A) | 377.3 |
| 1.65 | 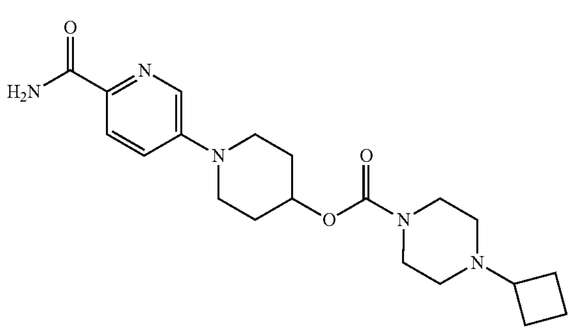 | 1-(6-carbamoylpyridin-3-yl)piperidin-4-yl 4-cyclobutylpiperazine-1-carboxylate | 1.41(A) | 388.1 |

TABLE 1-continued

| Ex. | Structure | Name | LCMS Rt [min], method | [M + H]+ |
|---|---|---|---|---|
| 1.66 | 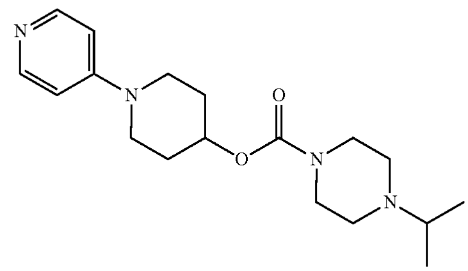 [SMILES: CC(C)N1CCN(C(=O)OC2CCN(c3ccncc3)CC2)CC1] | 1-(pyridin-4-yl)piperidin-4-yl 4-isopropylpiperazine-1-carboxylate | 1.14(A) | 333.2 |
| 1.67 | 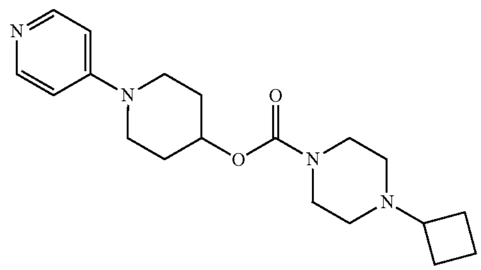 [SMILES: O=C(OC1CCN(c2ccncc2)CC1)N1CCN(C2CCC2)CC1] | 1-(pyridin-4-yl)piperidin-4-yl 4-cyclobutylpiperazine-1-carboxylate | 1.20(A) | 345.2 |
| 1.68 | 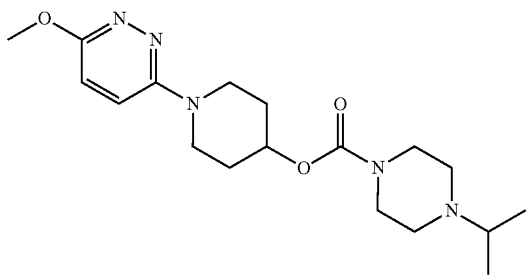 [SMILES: COc1ccc(N2CCC(OC(=O)N3CCN(C(C)C)CC3)CC2)nn1] | 1-(6-methoxypyridazin-3-yl)piperidin-4-yl 4-isopropylpiperazine-1-carboxylate | 1.20(A) | 364.3 |
| 1.69 | 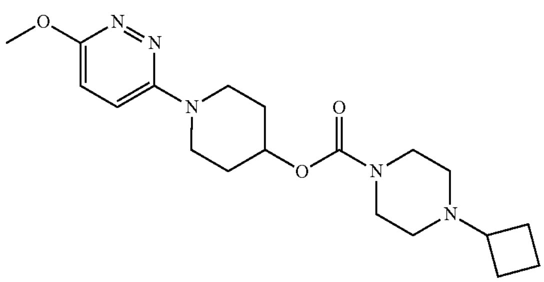 [SMILES: COc1ccc(N2CCC(OC(=O)N3CCN(C4CCC4)CC3)CC2)nn1] | 1-(6-methoxypyridazin-3-yl)piperidin-4-yl 4-cyclobutylpiperazine-1-carboxylate | 1.52(A) | 376.3 |
| 1.70 | 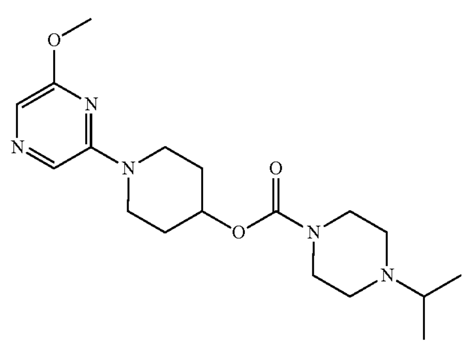 [SMILES: COc1cncc(N2CCC(OC(=O)N3CCN(C(C)C)CC3)CC2)n1] | 1-(6-methoxypyrazin-2-yl)piperidin-4-yl 4-isopropylpiperazine-1-carboxylate | 1.34(A) | 364.2 |

TABLE 1-continued
| Ex. | Structure | Name | LCMS Rt [min], method | [M + H]+ |
|---|---|---|---|---|
| 1.71 | 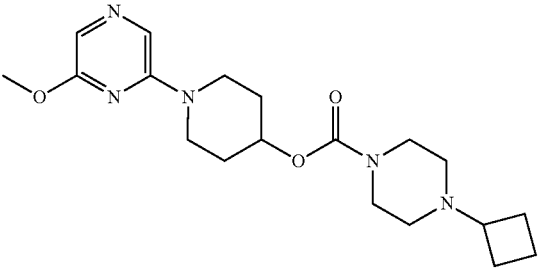 [SMILES: COc1cncc(N2CCC(OC(=O)N3CCN(C4CCC4)CC3)CC2)n1] | 1-(6-methoxypyrazin-2-yl)piperidin-4-yl 4-cyclobutylpiperazine-1-carboxylate | 1.39(A) | 376.2 |
| 1.72 | 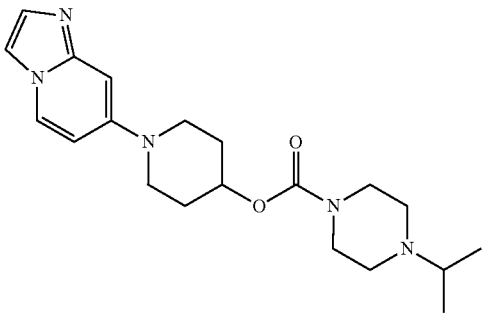 [SMILES: CC(C)N1CCN(C(=O)OC2CCN(c3ccn4ccnc4c3)CC2)CC1] | 1-(imidazo[1,2-a]pyridin-7-yl)piperidin-4-yl 4-isopropylpiperazine-1-carboxylate | 1.12(A) | 372.2 |
| 1.73 | 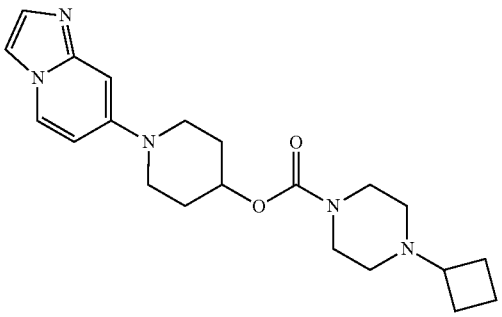 [SMILES: O=C(OC1CCN(c2ccn3ccnc3c2)CC1)N1CCN(C2CCC2)CC1] | 1-(imidazo[1,2-a]pyridin-7-yl)piperidin-4-yl 4-cyclobutylpiperazine-1-carboxylate | 1.24(A) | 384.2 |
| 1.74 | 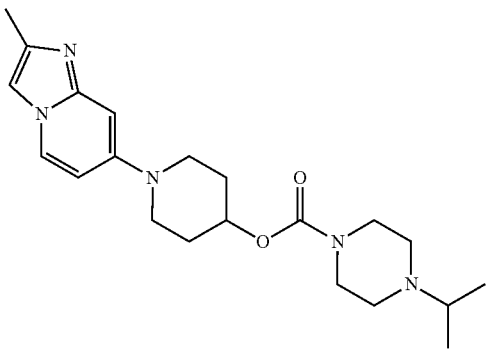 [SMILES: Cc1cn2ccc(N3CCC(OC(=O)N4CCN(C(C)C)CC4)CC3)cc2n1] | 1-(2-methylimidazo[1,2-a]pyridin-7-yl)piperidin-4-yl 4-isopropylpiperazine-1-carboxylate | 0.88(D) | 386.2 |

TABLE 1-continued

| Ex. | Structure | Name | LCMS Rt [min], method | [M + H]+ |
|---|---|---|---|---|
| 1.75 | 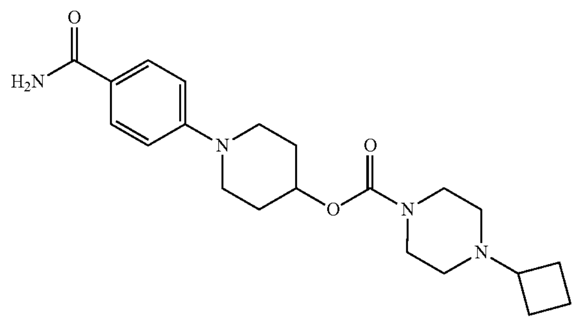 [SMILES: NC(=O)c1ccc(N2CCC(OC(=O)N3CCN(C4CCC4)CC3)CC2)cc1] | 1-(4-carbamoylphenyl)piperidin-4-yl 4-cyclobutylpiperazine-1-carboxylate | 1.40(A) | 387.1 |
| 1.76 | 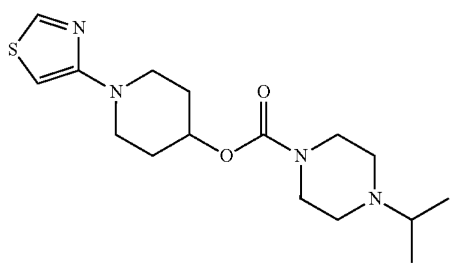 [SMILES: CC(C)N1CCN(C(=O)OC2CCN(c3cscn3)CC2)CC1] | 1-(thiazol-4-yl)piperidin-4-yl 4-isopropylpiperazine-1-carboxylate | 1.65(A) | 339 |
| 1.77 | 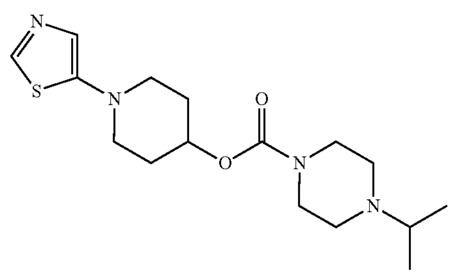 [SMILES: CC(C)N1CCN(C(=O)OC2CCN(c3cncs3)CC2)CC1] | 1-(thiazol-5-yl)piperidin-4-yl 4-isopropylpiperazine-1-carboxylate | 1.58(A) | 339 |
| 1.78 | 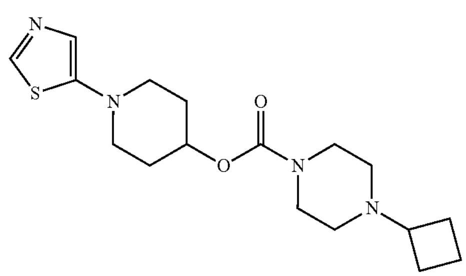 [SMILES: O=C(OC1CCN(c2cncs2)CC1)N1CCN(C2CCC2)CC1] | 1-(thiazol-5-yl)piperidin-4-yl 4-cyclobutylpiperazine-1-carboxylate | 1.68(A) | 351.2 |
| 1.79 | 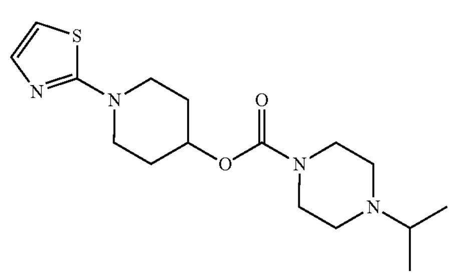 [SMILES: CC(C)N1CCN(C(=O)OC2CCN(c3nccs3)CC2)CC1] | 1-(thiazol-2-yl)piperidin-4-yl 4-isopropylpiperazine-1-carboxylate | 1.54(A) | 339.2 |

TABLE 1-continued

| Ex. | Structure | Name | LCMS Rt [min], method | [M + H]+ |
|---|---|---|---|---|
| 1.80 | 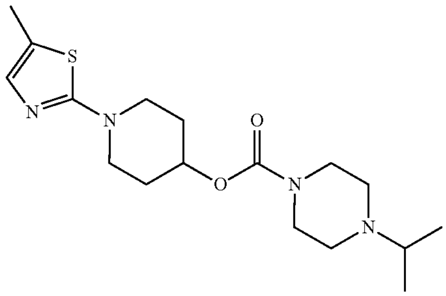 [SMILES: Cc1cnc(N2CCC(OC(=O)N3CCN(C(C)C)CC3)CC2)s1] | 1-(5-methylthiazol-2-yl)piperidin-4-yl 4-isopropylpiperazine-1-carboxylate | 1.37(A) | 353.2 |
| 1.81 | 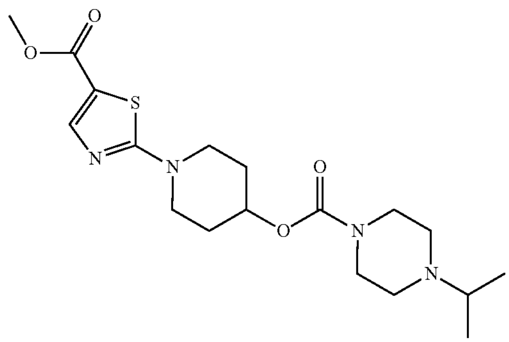 [SMILES: COC(=O)c1cnc(N2CCC(OC(=O)N3CCN(C(C)C)CC3)CC2)s1] | methyl 2-(4-(4-isopropylpiperazine-1-carbonyloxy)piperidin-1-yl)thiazole-5-carboxylate | 1.32(A) | 397.2 |
| 1.82 | 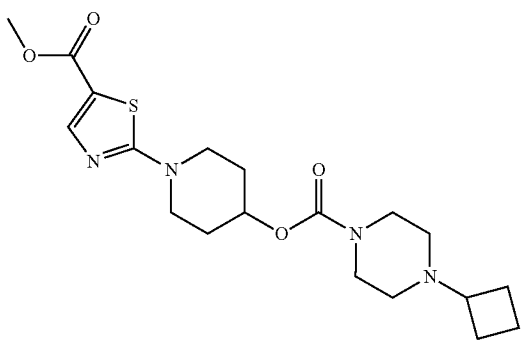 [SMILES: COC(=O)c1cnc(N2CCC(OC(=O)N3CCN(C4CCC4)CC3)CC2)s1] | methyl 2-(4-(4-cyclobutylpiperazine-1-carbonyloxy)piperidin-1-yl)thiazole-5-carboxylate | 1.37(A) | 409.2 |
| 1.83 | 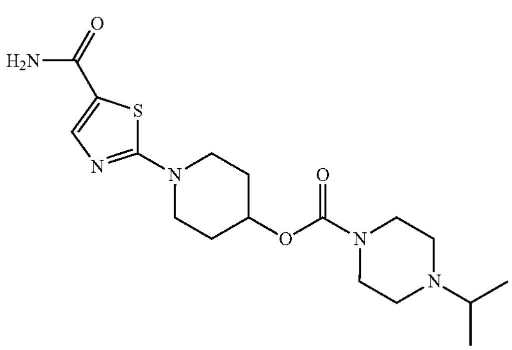 [SMILES: CC(C)N1CCN(C(=O)OC2CCN(c3ncc(C(N)=O)s3)CC2)CC1] | 1-(5-carbamoylthiazol-2-yl)piperidin-4-yl 4-isopropylpiperazine-1-carboxylate | 1.34(A) | 382.2 |

TABLE 1-continued

| Ex. | Structure | Name | LCMS Rt [min], method | [M + H]+ |
|---|---|---|---|---|
| 1.84 | 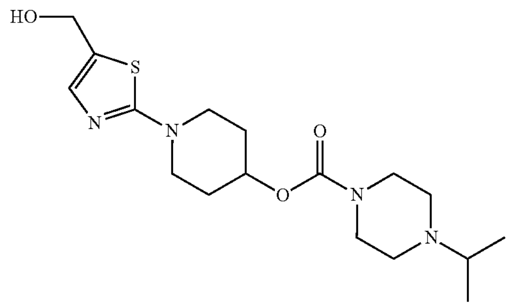 [SMILES: CC(C)N1CCN(C(=O)OC2CCN(c3ncc(CO)s3)CC2)CC1] | 1-(5-(hydroxymethyl)thiazol-2-yl)piperidin-4-yl 4-isopropylpiperazine-1-carboxylate | 1.38(A) | 369.2 |
| 1.85 | 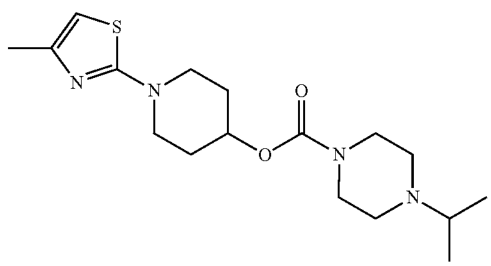 [SMILES: Cc1csc(N2CCC(OC(=O)N3CCN(C(C)C)CC3)CC2)n1] | 1-(4-methylthiazol-2-yl)piperidin-4-yl 4-isopropylpiperazine-1-carboxylate | 1.73(A) | 353 |
| 1.86 | 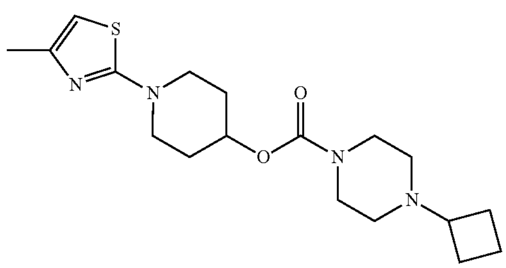 [SMILES: Cc1csc(N2CCC(OC(=O)N3CCN(C4CCC4)CC3)CC2)n1] | 1-(4-methylthiazol-2-yl)piperidin-4-yl 4-cyclobutylpiperazine-1-carboxylate | 1.42(A) | 365.2 |
| 1.87 | 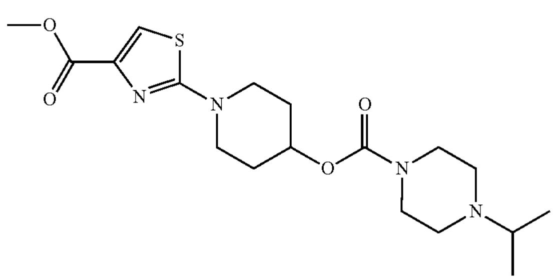 [SMILES: COC(=O)c1csc(N2CCC(OC(=O)N3CCN(C(C)C)CC3)CC2)n1] | methyl 2-(4-(4-isopropylpiperazine-1-carbonyloxy)piperidin-1-yl)thiazole-4-carboxylate | 1.57(A) | 397.2 |
| 1.88 | 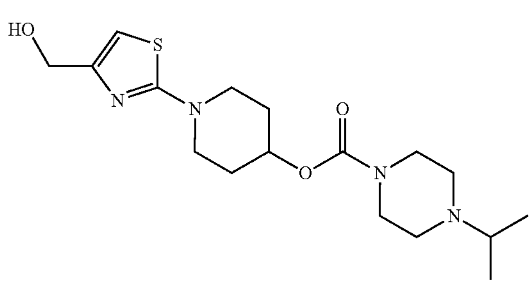 [SMILES: CC(C)N1CCN(C(=O)OC2CCN(c3nc(CO)cs3)CC2)CC1] | 1-(4-(hydroxymethyl)thiazol-2-yl)piperidin-4-yl 4-isopropylpiperazine-1-carboxylate | 1.54(A) | 369.2 |

TABLE 1-continued

| Ex. | Structure | Name | LCMS Rt [min], method | [M + H]+ |
|---|---|---|---|---|
| 1.89 | 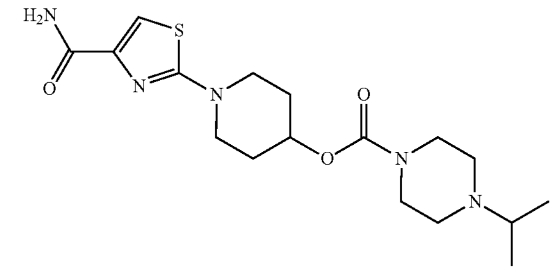 [SMILES: CC(C)N1CCN(C(=O)OC2CCN(c3nc(C(N)=O)cs3)CC2)CC1] | 1-(4-carbamoylthiazol-2-yl)piperidin-4-yl 4-isopropylpiperazine-1-carboxylate | 1.40(A) | 382.1 |
| 1.90 | 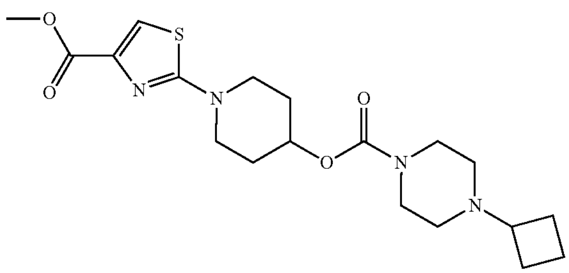 [SMILES: COC(=O)c1csc(N2CCC(OC(=O)N3CCN(C4CCC4)CC3)CC2)n1] | methyl 2-(4-(4-cyclobutylpiperazine-1-carbonyloxy)piperidin-1-yl)thiazole-4-carboxylate | 2.01(A) | 409.3 |
| 1.91 | 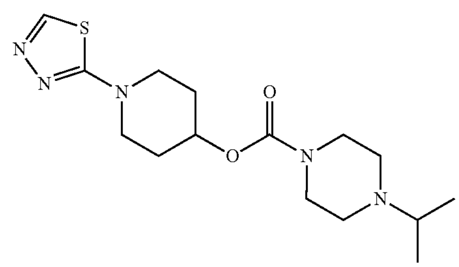 [SMILES: CC(C)N1CCN(C(=O)OC2CCN(c3nncs3)CC2)CC1] | 1-(1,3,4-thiadiazol-2-yl)piperidin-4-yl 4-isopropylpiperazine-1-carboxylate | 1.09(A) | 340.2 |
| 1.92 | 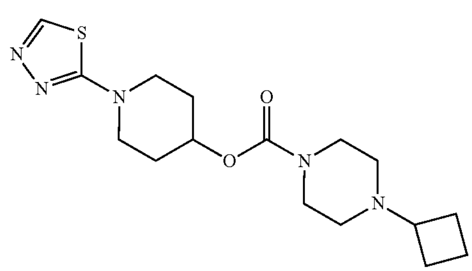 [SMILES: O=C(OC1CCN(c2nncs2)CC1)N1CCN(C2CCC2)CC1] | 1-(1,3,4-thiadiazol-2-yl)piperidin-4-yl 4-cyclobutylpiperazine-1-carboxylate | 1.15(A) | 352.2 |
| 1.93 | 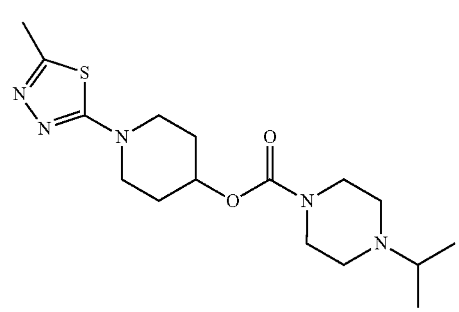 [SMILES: Cc1nnc(N2CCC(OC(=O)N3CCN(C(C)C)CC3)CC2)s1] | 1-(5-methyl-1,3,4-thiadiazol-2-yl)piperidin-4-yl 4-isopropylpiperazine-1-carboxylate | 1.50(A) | 354.1 |

TABLE 1-continued

| Ex. | Structure | Name | LCMS Rt [min], method | [M + H]+ |
|---|---|---|---|---|
| 1.94 | 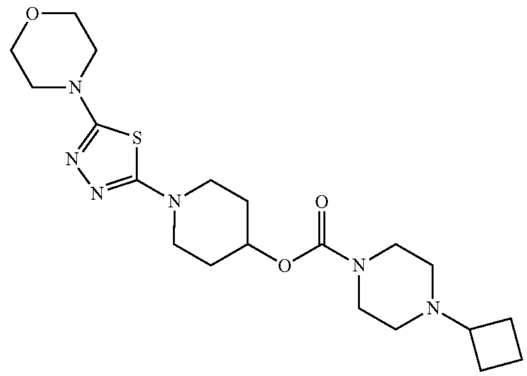 [SMILES: O=C(OC1CCN(c2nnc(N3CCOCC3)s2)CC1)N1CCN(C2CCC2)CC1] | 1-(5-morpholino-1,3,4-thiadiazol-2-yl)piperidin-4-yl 4-cyclobutylpiperazine-1-carboxylate | 1.48(A) | 437.6 |
| 1.95 | 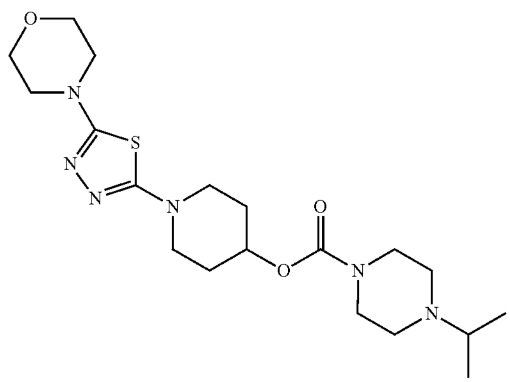 [SMILES: CC(C)N1CCN(C(=O)OC2CCN(c3nnc(N4CCOCC4)s3)CC2)CC1] | 1-(5-morpholino-1,3,4-thiadiazol-2-yl)piperidin-4-yl 4-isopropylpiperazine-1-carboxylate | 1.44(A) | 425.3 |
| 2.1 | 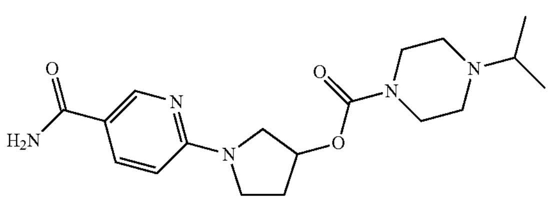 [SMILES: CC(C)N1CCN(C(=O)OC2CCN(c3ccc(C(N)=O)cn3)C2)CC1] | racemic 1-(5-carbamoylpyridin-2-yl)pyrrolidin-3-yl 4-isopropylpiperazine-1-carboxylate | 1.58(A) | 362.2 |
| 2.2 | 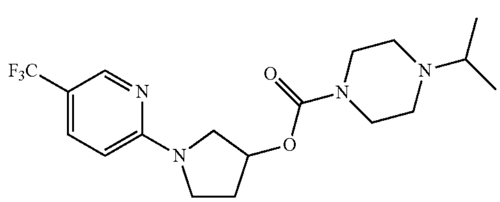 [SMILES: CC(C)N1CCN(C(=O)OC2CCN(c3ccc(C(F)(F)F)cn3)C2)CC1] | racemic 1-(5-(trifluoromethyl)pyridin-2-yl)pyrrolidin-3-yl 4-isopropylpiperazine-1-carboxylate | 2.00(A) | 387.2 |
| 2.3 | 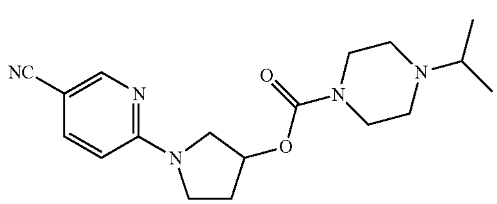 [SMILES: CC(C)N1CCN(C(=O)OC2CCN(c3ccc(C#N)cn3)C2)CC1] | racemic 1-(5-cyanopyridin-2-yl)pyrrolidin-3-yl 4-isopropylpiperazine-1-carboxylate | 1.79(A) | 344.2 |

TABLE 1-continued

| Ex. | Structure | Name | LCMS Rt [min], method | [M + H]+ |
|---|---|---|---|---|
| 2.4 | 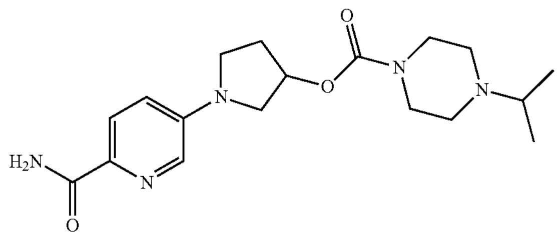 [SMILES: CC(C)N1CCN(C(=O)OC2CCN(c3ccc(C(N)=O)nc3)C2)CC1] | 1-(6-carbamoylpyridin-3-yl)pyrrolidin-3-yl 4-isopropylpiperazine-1-carboxylate | 1.33(A) | 362.2 |
| 3.1 | 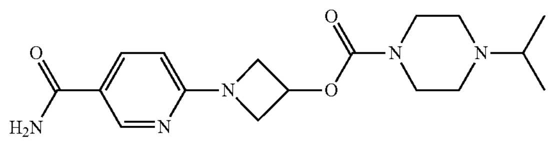 | 1-(5-carbamoylpyridin-2-yl)azetidin-3-yl 4-isopropylpiperazine-1-carboxylate | 1.59(A) | 348.2 |
| 3.2 | 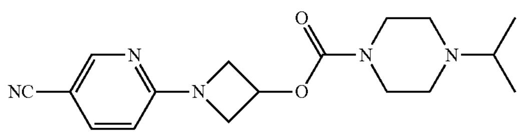 [SMILES: CC(C)N1CCN(C(=O)OC2CN(c3ccc(C#N)cn3)C2)CC1] | 1-(5-cyanopyridin-2-yl)azetidin-3-yl 4-isopropylpiperazine-1-carboxylate | 1.77(A) | 330.2 |
| 3.3 | 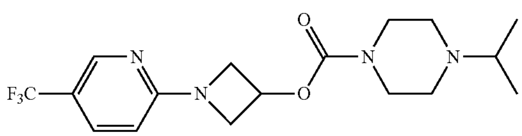 [SMILES: CC(C)N1CCN(C(=O)OC2CN(c3ccc(C(F)(F)F)cn3)C2)CC1] | 1-(5-(trifluoromethyl)pyridin-2-yl)azetidin-3-yl 4-isopropylpiperazine-1-carboxylate | 1.96(A) | 373.2 |
| 4.1 | 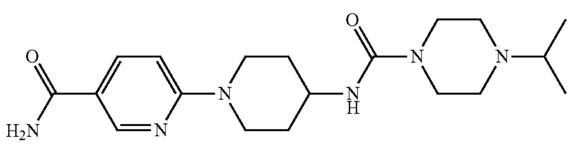 | N-(1-(5-carbamoylpyndin-2-yl)piperidin-4-yl)-4-isopropylpiperazine-1-carboxamide | 1.54(B) | 375.2 |

Biological Testing
1.1 In-Vitro Testing
A) Potency Assessment

The potency of compounds of the invention as H3 receptor antagonists can be assessed by measuring the blockade of (R)-alpha-methylhistamine-mediated cAMP production utilizing a LANCE Ultra cAMP kit (PE #TRF0263) in CHO cells expressing human H3 receptors (GenBank: BC096840; Strausberg R L et al, Proc. Natl. Acad. Sci. U.S.A. 99(26), 16899-16903; 2002).

Protocol:
1. Preparation of the stimulation buffer (30 ml): 29.4 ml HBSS (GIBCO #14025), 150 µl 1 M HEPES (GIBCO #15630), 30 µl 500 mM IBMX (CALBIOCHEM #410957) and 400 µl 7.5% BSA (GIBCO #10438-026).
2. Preparation of assay plate: Different concentrations of the compounds of the invention (0.01-1000 nM), H3 positive controls and cAMP calibration standards; 3 mM Forskolin (CALBIOCHEM #344270); 5 µM (R)-alpha-methylhistamine (H3 receptor agonist); 1% DMSO (SIGMA #D2650); total volume: 95 nl.
3. Preparation of the cell solution: Collect cells with stimulation buffer, final density: 100,000 cells/ml.
4. Reaction: (a) transfer 10 µl of cell solution to assay plate, (b) centrifuge at 600 rpm for 3 min and incubate 50 min at room temperature, (c) add 5 µL 4× Eu-cAMP tracer solution (60 µl Eu-cAMP tracer stock solution+2.94 ml cAMP detection buffer) and 5 µL 4× ULight™-anti-cAMP solution (20 µl Eu-cAMP tracer stock solution+2.98 ml cAMP detection buffer) to assay plate.
5. Reading plate on EnVision: flash energy: 100%; excitation filter: 111 UV2 320; emission filter: 203 (Eu 615) and 205 (APC 665); number of laser flashes: 20; window: 100 µs; laser mirror module: 445 or 446; laser cycle: 16,600 µs.
6. Data analysis by GraphPad Prism: log(compound concentration) vs. response; variable slope.

B) Affinity Assessment

The affinity of compounds of the invention to the H3 receptor can be assessed by measuring displacement of binding of the radioligand [3H]-N-α-Methylhistamine (PerkinElmer, #NET1027250UC) to membranes containing human H3 receptors (PerkinElmer, #ES-392-M400UA; GenBank: NM_007232.2; Hill S J et al, International Union of Pharmacology XIII. Classification of histamine receptors, Pharmacol Rev, 49(3), 253-278, 1997).

Protocol:
1. Preparation of binding assay buffer (500 ml): 25 ml 1 M Tris-HCl pH 7.5 (Invitrogen, #15567-027), 2.5 ml 1 M MgCl2 (Sigma, #M1028-100ML), 472.5 ml ddH2O.
2. Compound serial dilution: Dilution was performed by BioTek Precision on compound dilution plate. Compound concentrations start at 5 or 10 µM, 10 point dose titrations with 3- or 5-fold serial dilutions.
3. Preparation of 2× membrane solution (25 ml): 1.25 ml human Histamine H3 receptor stock, 23.75 ml assay buffer.

4. Preparation of 2× solution of [3H]-N-α-methylhistamine (25 ml): 4.27 μl [3H]-N-α-methylhistamine stock, 25 ml assay buffer.
5. Assemble binding reaction: (a) transfer 1 μl of compound solution, 1 μl 100% DMSO and 1 μl 1 M (R)(-)-α-Methylhistamine (Sigma, #H128) to the reaction plate at room temperature, (b) transfer 50 μl of 2× protein solution to reaction plate, (c) transfer 49 μl of 2× radioligand solution to reaction plate (Corning® 96 well EIA/RIA plate; Sigma, #CLS3797).
6. Cover the reaction plate with a TopSeal™-A film (Perkin Elmer, #6005185) and incubate at 28° C. for 120 min. Equilibrate Zeba Spin Desalting Plates (Thermo Scientific, #89808) to room temperature for 120 min.
7. Remove the sealing material from the bottom of the filtration plate. Place the plate on a wash plate. Centrifuge at 1000 g for 2 min to remove the storage buffer at room temperature.
8. Transfer 70 μl binding reaction from reaction plate into filtration plates. Place the filtration plates on top of collection plate. Centrifuge the plate assembly at 1000 g for 2 min to collect the protein with bound radioligand. Add 200 μl of Microscint-40 (PerkinElmer, #6013641-1L) to each well of the collection plate. Cover the plates with TopSeal™-A film.
9. Read the plates on Wallac Microbeta Trilux 2450, Instrument settings: counting mode: CPM, counting time: 2 min.
10. Data analysis: GraphPad Prism: log(compound concentration) vs. response; variable slope. The Ki is calculated based on Chang and Prusoff: Ki=IC50/{1+([radioligand]/Kd)}

Table 2 represents Ki values from above described potency/affinity assessments of compounds of the invention against human H3 receptors.

TABLE 2

| Example | Potency Ki (nM) | Affinity Ki (nM) | Example | Potency Ki (nM) | Affinity Ki (nM) |
|---|---|---|---|---|---|
| 1.1 | 1.8 | 37 | 1.53 | 1.6 | 31 |
| 1.2 | 1.4 | 33 | 1.54 | 0.7 | 8.9 |
| 1.3 | 1.7 | 101 | 1.55 | 1.6 | 15 |
| 1.4 | 5.5 | 52 | 1.56 | 0.5 | 3.5 |
| 1.5 | 3.7 | 20 | 1.57 | 0.7 | 6.5 |
| 1.6 | 2.9 | 30 | 1.58 | 0.6 | 3.1 |
| 1.7 | 3.5 | 41 | 1.59 | 0.2 | 2.5 |
| 1.8 | 1.5 | 36 | 1.60 | 0.1 | 1.4 |
| 1.9 | 1.5 | 40 | 1.61 | 0.4 | n.t. |
| 1.10 | 9 | 26 | 1.62 | 0.2 | n.t. |
| 1.11 | 2.1 | 45 | 1.63 | 0.2 | n.t. |
| 1.12 | 3.3 | 41 | 1.64 | 0.3 | n.t. |
| 1.13 | 2.9 | 23 | 1.65 | 121 | n.t. |
| 1.14 | 2.9 | 67 | 1.66 | 1.1 | 8.4 |
| 1.15 | 3.8 | 117 | 1.67 | 0.4 | 3.1 |
| 1.16 | 4.5 | 60 | 1.68 | 1.7 | 47 |
| 1.17 | 6.0 | 96 | 1.69 | 1.1 | 19 |
| 1.18 | 5.1 | 31 | 1.70 | 1.1 | 17 |
| 1.19 | 0.4 | n.t. | 1.71 | 0.5 | 12 |
| 1.20 | 2.2 | 29 | 1.72 | 1.7 | 13 |
| 1.21 | 2.3 | 30 | 1.73 | 0.4 | 2.7 |
| 1.22 | 1.1 | 10 | 1.74 | 0.4 | 1.8 |
| 1.23 | 1.6 | 45 | 1.75 | 94 | n.t. |
| 1.24 | 1.7 | 15 | 1.76 | 1.1 | 17 |
| 1.25 | 1.7 | 8.4 | 1.77 | 1.5 | 22 |
| 1.26 | 4.1 | 82 | 1.78 | 0.3 | n.t. |
| 1.27 | 9.9 | 71 | 1.79 | 4.9 | 14 |
| 1.28 | 3.6 | 68 | 1.80 | 2.2 | 23 |
| 1.29 | 1.6 | 61 | 1.81 | 7.3 | 41 |
| 1.30 | 2.5 | 30 | 1.82 | 3.8 | 36 |
| 1.31 | 3 | 26 | 1.83 | 6.2 | 59 |
| 1.32 | 4.1 | 36 | 1.84 | 5.8 | 47 |
| 1.33 | 0.4 | n.t. | 1.85 | 4.2 | 18 |
| 1.34 | 1.7 | 14 | 1.86 | 1.5 | 15 |
| 1.35 | 4 | 77 | 1.87 | 4.3 | 31 |
| 1.36 | 2.6 | 50 | 1.88 | 4.2 | 35 |
| 1.37 | 0.5 | 7.4 | 1.89 | 3.3 | 40 |

TABLE 2-continued

| Example | Potency Ki (nM) | Affinity Ki (nM) | Example | Potency Ki (nM) | Affinity Ki (nM) |
|---|---|---|---|---|---|
| 1.38 | 0.3 | n.t. | 1.90 | 2.7 | 29 |
| 1.39 | 33 | 276 | 1.91 | 4.7 | 39 |
| 1.40 | 1.7 | 27 | 1.92 | 1.1 | 32 |
| 1.41 | 2 | 38 | 1.93 | 5.2 | 48 |
| 1.42 | 1.7 | 11 | 1.94 | 2 | 24 |
| 1.43 | 0.7 | n.t. | 1.95 | 2.7 | 27 |
| 1.44 | 3.1 | 33 | 2.1 | 25 | 340 |
| 1.45 | 93 | n.t. | 2.2 | 16 | 139 |
| 1.46 | 45 | 518 | 2.3 | 14 | 258 |
| 1.47 | 182 | n.t. | 2.4 | 5.4 | n.t. |
| 1.48 | 0.9 | 14 | 3.1 | 40 | 235 |
| 1.49 | 1 | 15 | 3.2 | 9.2 | 132 |
| 1.50 | 0.4 | 12 | 3.3 | 12 | 164 |
| 1.51 | 1.4 | 8.3 | 4.1 | 39 | 797 |
| 1.52 | 0.4 | 12 | | | | n.t. Not tested

C) Inverse Agonist Activity Assessment

For assessment of inverse agonism activity, the GTPγS assay can be used (Laitinen J T and Jokinen M, J Neurochem, 71(2), 1998, 808-816).

Table 3 represents data from inverse agonist activity assessments. "% response at 10 μM" displays inhibition of basal H3 receptor activity in the presence of 10 μM of the compound of the invention. The antagonist mode was tested using 30 nM of (R)-alpha-methylhistamine as agonist. Similarly, "% inhibition at 10 μM" displays inhibition of agonist-induced H3 receptor activity in the presence of 10 μM of the compound of the invention

TABLE 3

| | Agonist mode | | Antagonist mode | |
|---|---|---|---|---|
| Example | EC50 (nM) | % response at 10 μM | IC50 (nM) | % inhibition at 10 μM |
| 1.1 | 4.7 | −69 | 103 | 172 |

1.2 In-Vivo Testing

A) Effects on Brain Tele-Methylhistamine Levels

Compounds of the invention were dissolved in 20% 2-hydroxyl-beta-cyclodextran (HBC) and then sonicated briefly until there is little or no suspension in the solution. Animals (male Sprague-Dawley rats at the age of 8 weeks) were orally dosed with test compounds 1 hour or other longer time points before they were sacrificed using $CO_2$.

Blood Sample Collection:

A cardiac puncture was performed to collect blood sample from the cardiac cavity. The collected blood was immediately mixed with EDTA-K2 20 μl/ml to avoid blood clotting. The blood samples in tubes were then centrifuged (15 mim, 6000 rpm) and the plasma transferred to new tubes and then temporarily kept in dry ice until they were stored in a −70° C. freezer.

CSF collection: CSF samples were taken from the foramen magnum of the animal (using a #0.5 intravenous needle), and the CSF sample were kept in dry ice.

Brain Tissue Collection:

The rat brain were taken out of the skull and rinsed with ice-cold saline first. The frontal cortex was separated from the rest of the brain on top of a petri dish with ice underneath. The wet weight of the frontal cortex was weighed and recorded immediately. The frontal cortex sample was then kept in dry ice until they are transferred to a −70° C. freezer.

Bioanalytical Methods for Tele-Methyl Histamine and Compounds:
  Instrument: Agilent 6410, triple quadrupole mass spectrometer
  Matrix: rat plasma, frontal cortex homogenate and cerebrospinal fluid (CSF)
  Analyte: H3 compounds.
  Internal standard: Dexamethasone
HPLC Conditions Mobile Phase A: H2O— 0.1% NH3.H2O:
  Mobile phase B: MeOH— 0.1% NH3.H2O
  Column: Ultimate XB-C18 (2.1×50 mm, 5 μm)
  Flow rate: 0.45 mL/min, temperature: 40° C.
MS Conditions:
  ESI: positive ion
  MRM detection
  Dexamethasone: [M+H]+m/z 393.3→373.2; CE:4; Fragmentor:110
Sample Preparation:
  Frontal Cortex:
    the brain sample was homogenized for 2 min with 3 volumes (v/w) of homogenizing solution (EtOH:PBS=85:15), and then centrifuged at 12,000 rpm for 5 min. The 30 μL supernatant of brain homogenate sample was added with 30 μL of the internal standard (Dexamethasone, 300 ng/mL) and then followed by 150 μL ACN for protein precipitation. The mixture was vortexed for 2 min and centrifuged at 12000 rpm for 5 min. The 5 μL supernatant was injected onto LC-MS/MS for analysis.
  Plasma and CSF:
    an aliquot of 30 μL sample was added with 30 μL of the internal standard (300 ng/mL Dexamethasone) and then followed by 150 μL ACN for protein precipitation. The mixture was vortexed for 2 min and centrifuged at 12000 rpm for 5 min. The 5 μL supernatant was injected onto LC-MS/MS for analysis.

Table 4 represents data from measurements of the tele-methylhistamine level in brain.

TABLE 4

| Example | % change in telemethylhistamine brain levels |
|---|---|
| 1.1 | 58.0 |

B) Effects on Wakefulness

Animals: Male Sprague-Dawly rats (280-320 g) were housed individually under an ambient temperature of 22±0.5° C. with a relative humidity of 60±2% and an automatically controlled 12-h light/12-h dark cycle (light on at 07:00, illumination intensity≈100 lux). The animals had free access to food and water.

EEG recording set up, Polygraphic Recordings and Vigilance State Analysis: Under pentobarbital anesthesia (50 mg/kg, i.p.), rats were chronically implanted with EEG and electromyogram (EMG) electrodes for polysomnographic recordings (Huang et al, J Neurosci, 23, 5975-5983, 2003). Two stainless steel screws (1 mm in diameter) EEG electrodes (the first screw: anteroposterior (AP), +2 mm; left-right (LR), −2 mm; and the second: AP, −2 mm; LR, −2 mm, AP from bregma, LR from lambda) and a reference electrode (opposite to EEG screw side, AP, +3 mm; LR, 3 mm) were surgically implanted and 3 stainless steel screws for anchorage to the skull. Two insulated stainless steel, Teflon-coated wires were bilaterally placed into both trapezius muscles and served as EMG electrodes for rats. All electrodes were attached to a micro connector and fixed to the skull with dental cement.

The EEG and EMG recordings were carried out by means of a slip ring designed so that behavioral movement of the rat would not be restricted. After an 8-day recovery period, the rats were housed individually in transparent barrels and habituated to the recording cable for 3-4 days before polygraphic recording.

For the study of spontaneous sleep-wakefulness cycles, each animal was recorded for 24 h beginning at 19:00 P.M., the offset of the light period. The animals then entered the pharmacological phase of the study, in which sleep-wakefulness parameters were recorded for 72 h. The data collected during the first 24 h also served as baseline comparison data for the second experimental day.

Cortical EEG and EMG signals were amplified, filtered (EEG, 0.5-30 Hz; EMG, 20-200 Hz), digitized at a sampling rate of 128 Hz, and recorded by using SLEEPSIGN (Kissei Comtec, Nagano, Japan). When complete, polygraphic recordings were automatically scored offline by 4-sec epochs as wake, REM, and NREM sleep by SleepSign according to standard criteria (Huang et al, Nat Neurosci, 8, 858-859, 2005). As a final step, defined sleep-wake stages were examined visually and corrected, if necessary. EEG power density curve was plotted for each stage during 4 h after drug administration. The power of each 0.25 Hz bin was averaged across the sleep or wake stage and normalized as a group by calculating the percentage of each bin from the total power (0.25-25 Hz).

Pharmacological Treatments: Tested compounds, caffeine (positive reference compound) or compounds of the invention were prepared in 20% 2-hydroxyl-beta-cyclodextran (HBC). On the vehicle-treated day, all animals were administered with vehicle at 9:00 A.M. On the drug-treated day, the test compound, caffeine, or vehicle was given at 9:00 A.M. Thereafter, continuous recording was kept to the 3rd day. The volume was injected oral, or intraperitoneally at 2 ml/kg. Separate groups of rats were used for each dose (n=8 rats per group).

Time-course changes in the amounts of sleep-wake, sleep/wake stage transition number, as well as number and duration of sleep/wake bouts in light/dark phases, were analyzed by the paired t test, with each animal serving as its own control.

Table 5 represents data from measurements of percent increase in wakefulness in rats. Date is given for first 4 hours after oral compound administration.

TABLE 5

| Example | % increase in wakefulness at 0.1 mg/kg | % increase in wakefulness at 0.3 mg/kg | % increase in wakefulness at 1 mg/kg | % increase in wakefulness at 10 mg |
|---|---|---|---|---|
| 1.1 | +31.6 | +27.4 * | +42.2 ** | +56.2 ** |

* $p < 0.5$,
** $p < 0.01$ (comparison with vehicle group)

In one embodiment, the invention provides a method of inhibiting H3 receptors in a subject, wherein the method comprises administering to the subject a therapeutically effective amount of a compound of formula I or a pharmaceutically acceptable salt thereof.

In a further embodiment, the invention provides a method of treating a disorder or a disease in a subject mediated by H3 receptors, wherein the method comprises administering to the subject a therapeutically effective amount of a compound of formula I or a pharmaceutically acceptable salt thereof. Preferably said disorder or said disease is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

In yet a further embodiment, the invention provides the use of a compound of formula I or a pharmaceutically acceptable salt thereof, for the treatment of a disorder or disease in a subject mediated by H3 receptors.

In yet a further embodiment, the invention provides the use of a compound of formula I or a pharmaceutically acceptable salt thereof, for the treatment of a disorder or disease in a subject characterized by an abnormal activity of H3 receptors. Preferably said disorder or said disease is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

In yet a further embodiment, the invention provides the use of a compound of formula I or a pharmaceutically acceptable salt thereof, for the treatment of a disorder or disease in a subject associated with irregularities of H3 receptor-modulated signal transmission. Preferably said disorder or said disease is selected from narcolepsy; fatigue associated with multiple sclerosis; fatigue associated with Parkinson's disease; cognitive impairment associated with schizophrenia; cognitive impairment associated with Alzheimer's disease; mild cognitive impairment; Tourette syndrome; and Attention-deficit hyperactivity disorder; very especially narcolepsy.

The invention claimed is:
1. A compound of the formula I

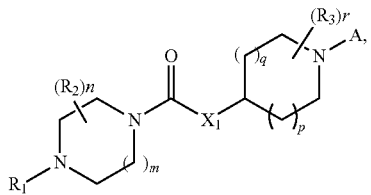

(I)

or a salt thereof, wherein $R_1$ is $C_{1-6}$alkyl, $C_{2-6}$alkenyl, $C_{2-6}$alkinyl, $C_{3-6}$cycloalkyl, $C_{5-6}$cycloalkenyl or $C_{3-6}$cycloalkyl-$C_{1-4}$alkyl; wherein said $C_{1-6}$alkyl, $C_{2-6}$alkenyl, $C_{2-6}$alkinyl or $C_{3-6}$cycloalkyl-$C_{1-4}$alkyl may be substituted once or more than once by halogen, hydroxyl or $C_{1-4}$alkoxy; and wherein said $C_{3-6}$cycloalkyl or $C_{5-6}$cycloalkenyl may be substituted once or more than once by halogen, hydroxyl, $C_{1-4}$alkyl, $C_{1-4}$halogenalkyl, $C_{1-4}$hydroxyalkyl or $C_{1-4}$alkoxy;

m is 1 or 2;

n is 0, 1, 2, 3 or 4;

each $R_2$ independently is halogen, hydroxyl, amino, cyano, nitro, $C_{1-6}$alkyl, $C_{1-6}$halogenalkyl, $C_{1-6}$hydroxyalkyl, $C_{1-4}$alkoxy-$C_{1-6}$alkyl, amino-$C_{1-6}$alkyl, $C_{1-4}$alkyl-amino-$C_{1-6}$alkyl, di($C_{1-4}$alkyl)-amino-$C_{1-6}$alkyl, $C_{1-6}$alkoxy, $C_{1-6}$halogenalkoxy, $C_{1-6}$alkylamino, di($C_{1-6}$ alkyl)amino, $C_{2-6}$alkenyl, $C_{2-6}$halogenalkenyl, $C_{2-6}$alkinyl or $C_{2-6}$halogenalkinyl;

or $C_{3-6}$cycloalkyl, wherein one carbon atom may be replaced by an oxygen atom, wherein the $C_{3-6}$cycloalkyl may be attached directly to the methylene or via a $C_{1-2}$alkylene, and wherein the $C_{3-6}$cycloalkyl may be substituted once or more than once by halogen;

or two $R_2$ at the same carbon atom form together with said carbon atom a $C_{3-6}$cycloalkyl;

$X_1$ is oxygen;

p is 1 and q is 1;

p is 0 and q is 1; or p is 0 and q is 0;

r is 0, 1, 2, 3 or 4;

each $R_3$ independently is halogen, hydroxyl, amino, cyano, nitro, $C_{1-6}$alkyl, $C_{1-6}$halogenalkyl, $C_{1-6}$hydroxyalkyl, $C_{1-4}$alkoxy-$C_{1-6}$alkyl, amino-$C_{1-6}$alkyl, $C_{1-4}$alkyl-amino-$C_{1-6}$alkyl, di($C_{1-4}$alkyl)-amino-$C_{1-6}$alkyl, $C_{1-6}$alkoxy, $C_{1-6}$halogenalkoxy, $C_{1-6}$alkylamino, di($C_{1-6}$ alkyl)amino, $C_{2-6}$alkenyl, $C_{2-6}$halogenalkenyl, $C_{2-6}$alkinyl or $C_{2-6}$halogenalkinyl;

or $C_{3-6}$cycloalkyl, wherein one carbon atom may be replaced by an oxygen atom, wherein the $C_{3-6}$cycloalkyl may be attached directly to the methylene or via a $C_{1-2}$alkylene, and wherein the $C_{3-6}$cycloalkyl may be substituted once or more than once by halogen;

or two $R_3$ at the same carbon atom form together with said carbon atom a $C_{3-6}$cycloalkyl;

A is a five- to six-membered monocyclic or an eight- to ten-membered fused bicyclic aromatic ring system, wherein said ring system may contain from 1 to 4 hetero atoms selected from nitrogen, oxygen and sulfur, and wherein said ring system may be substituted once or more than once by $R_5$;

each $R_5$ independently is halogen; cyano; nitro; hydroxy; amino; —C(O)H; —C(O)NH$_2$; —C(O)OH; —$X_2$—$R_6$; or —$X_3$—$B_1$;

$X_2$ is selected from bond; carbonyl; oxygen; sulfur; —S(O)—; —S(O)$_2$—; amino, which may be substituted by $C_{1-4}$alkyl; —N($R_a$)—C(O)—; —C(O)—N($R_b$)—; —C(O)—O—; —O—C(O)—; —N($R_c$)—S(O)$_2$—; —S(O)$_2$—N($R_d$)—; and —NHC(O)NH—;

$R_a$, $R_b$, $R_c$ and $R_d$ each independently is hydrogen or $C_{1-4}$alkyl;

$R_6$ is $C_{1-6}$alkyl; $C_{1-6}$halogenalkyl; $C_{1-6}$cyanoalkyl; $C_{1-6}$carboxyalkyl; $C_{1-6}$hydroxyalkyl; $C_{1-4}$alkoxy-$C_{1-6}$alkyl; $C_{1-4}$alkoxy-$C_{1-4}$alkoxy-$C_{1-6}$alkyl; $C_{1-4}$alkylcarbonyl-$C_{1-6}$alkyl; $C_{1-4}$alkoxycarbonyl-$C_{1-6}$alkyl; $C_{1-4}$alkylcarbonyloxy-$C_{1-6}$alkyl; $C_{1-6}$aminoalkyl; $C_{1-4}$alkylamino-$C_{1-6}$alkyl; di($C_{1-4}$alkyl)amino-$C_{1-6}$alkyl; aminocarbonyl-$C_{1-6}$alkyl; $C_{1-4}$alkylaminocarbonyl-$C_{1-6}$alkyl; di($C_{1-4}$alkyl)aminocarbonyl-$C_{1-6}$alkyl; $C_{1-4}$alkylcarbonylamino-$C_{1-6}$alkyl; $C_{1-4}$alkylaminosulfonyl-$C_{1-6}$alkyl; di($C_{1-4}$alkyl)aminosulfonyl-$C_{1-6}$alkyl; $C_{2-6}$alkenyl; $C_{2-6}$halogenalkenyl; $C_{2-6}$alkinyl; $C_{2-6}$halogenalkinyl;

$X_3$ is bond or $C_{1-3}$alkylene, wherein one carbon atom of the $C_{1-3}$alkylene may be replaced by a group selected from carbonyl; oxygen; sulfur; —S(O)—; —S(O)$_2$—; amino, which may be substituted by $C_{1-4}$alkyl; N($R_e$)—C(O)—; —C(O)—N($R_f$)—; —C(O)—O—; —O—C(O)—; —N($R_g$)—S(O)$_2$—; —S(O)$_2$—N($R_h$)—; and —NHC(O)NH—;

$R_e$, $R_f$, $R_g$ and $R_h$ each independently is hydrogen or $C_{1-4}$alkyl;

$B_1$ is a three- to seven-membered monocyclic ring system which may be aromatic, saturated or unsaturated non-aromatic and which may contain from 1 to 4 hetero atoms selected from nitrogen, oxygen and sulfur, wherein the ring system may in turn be substituted once or more than once by $R_7$;

each $R_7$ independently is halogen, cyano, $C_{1-4}$alkyl, $C_{1-4}$halogenalkyl, $C_{1-4}$alkoxy, or $C_{1-4}$halogenalkoxy; or two $R_7$ at the same ring atom together are oxo;

or two $R_5$ at adjacent ring atoms atoms form together with said ring atoms a fused five- to seven-membered monocyclic unsaturated non-aromatic ring system which may contain from 1 to 4 hetero atoms selected from nitrogen, oxygen and sulfur, wherein the ring system may in turn be substituted once or more than once by $R_8$, and wherein each $R_8$ independently is halogen, $C_{1-4}$alkyl or $C_{1-4}$alkoxy, or two $R_8$ at the same ring atom together are oxo;

and provided that the compounds

N-[(3R)-1-[7-[[(2,4-dichlorophenyl)methyl]amino]pyrazolo[1,5-a]pyrimidin-5-yl]-3-pyrrolidinyl]-4-methyl-1-piperazinecarboxamide;

4-cyclopentyl-N-[1-[5-(trifluoromethyl)-2-pyridinyl]-3-azetidinyl]-1-piperazinecarboxamide;

4-cyclopentyl-N-[1-[5-(trifluoromethyl)-2-pyridinyl]-3-pyrrolidinyl]-1-piperazinecarboxamide;

4-(1,1-dimethylethyl)hexahydro-N-[1-(2-pyrimidinyl)-4-piperidinyl]-1H-1,4-diazepine-1-carboxamide;

4-ethyl-N-[1-(2-pyrimidinyl)-4-piperidinyl]-1-piperazinecarboxamide;

hexahydro-4-methyl-N-[1-(2-pyrimidinyl)-4-piperidinyl]-1H-1,4-diazepine-1-carboxamide;

4-(2,2-difluoroethyl)-N-[1-(2-pyrimidinyl)-4-piperidinyl]-1-piperazinecarboxamide;

N-(1-(4-acetylphenyl)piperidin-4-yl)-4-cyclopentylpiperazine-1-carboxamide; and

N-(1-(4-acetylphenyl)piperidin-4-yl)-4-cyclobutylpiperazine-1-carboxamide are excluded.

2. A compound of formula I according to claim 1, wherein $X_1$ is oxygen; or a salt thereof.

3. A compound of formula I according to claim 1, wherein p is 1 and q is 1; or a salt thereof.

4. A compound of formula I according to claim 1, wherein $R_1$ is isopropyl, cyclopropyl, cyclobutyl or cyclopentyl and m is 1; or a salt thereof.

5. A compound of formula I according to claim 1, wherein A is a six-membered monocyclic aromatic ring system, wherein said ring system contains from 1 to 3 nitrogen atoms and wherein said ring system may be substituted once or more than once by $R_5$; or a salt thereof.

6. A compound of formula I according to claim 1, wherein $R_1$ is isopropyl; m is 1; $X_1$ is oxygen; p is 1 and q is 1; n is 0; p is 1 and q is 1; A is

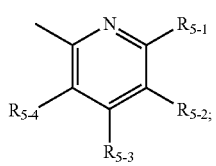

each of $R_{5-1}$, $R_{5-3}$ and $R_{5-4}$ is hydrogen;

$R_{5-2}$ is halogen; cyano; —C(O)NH$_2$; or —X$_2$—R$_6$; X$_2$ is selected from bond; carbonyl; oxygen; —C(O)—NH—; and —C(O)—O—; $R_6$ is $C_{1-6}$alkyl; $C_{1-6}$halogenalkyl; or $C_{1-4}$alkoxy-$C_{1-6}$alkyl;

or a salt thereof.

7. A compound of formula I according to claim 1, wherein said compound is selected from the group consisting of 1-(5-carbamoylpyridin-2-yl)piperidin-4-yl 4-isopropylpiperazine-1-carboxylate;

1-(5-carbamoylpyridin-2-yl)piperidin-4-yl 4-cyclobutylpiperazine-1-carboxylate;

1-(5-carbamoylpyridin-2-yl)piperidin-4-yl 4-cyclopentylpiperazine-1-carboxylate;

1-(5-carbamoylpyridin-2-yl)piperidin-4-yl 4-cyclopropylpiperazine-1-carboxylate;

1-(5-(dimethylcarbamoyl)pyridin-2-yl)piperidin-4-yl 4-isopropylpiperazine-1-carboxylate;

1-(5-cyanopyridin-2-yl)piperidin-4-yl 4-isopropylpiperazine-1-carboxylate;

1-(5-(methylcarbamoyl)pyridin-2-yl)piperidin-4-yl 4-isopropylpiperazine-1-carboxylate;

1-(pyridin-2-yl)piperidin-4-yl 4-isopropylpiperazine-1-carboxylate;

1-(5-fluoropyridin-2-yl)piperidin-4-yl 4-isopropylpiperazine-1-carboxylate;

1-(5-(trifluoromethyl)pyridin-2-yl)piperidin-4-yl 4-isopropylpiperazine-1-carboxylate;

1-(5-methylpyridin-2-yl)piperidin-4-yl 4-isopropylpiperazine-1-carboxylate;

1-(5-(methoxycarbonyl)pyridin-2-yl)piperidin-4-yl 4-isopropylpiperazine-1-carboxylate;

1-(4-(isopropoxycarbonyl)pyridin-2-yl)piperidin-4-yl 4-isopropylpiperazine-1-carboxylate;

1-(5-(ethoxycarbonyl)pyridin-2-yl)piperidin-4-yl 4-isopropylpiperazine-1-carboxylate;

1-(5-carbamoylpyrazin-2-yl)piperidin-4-yl 4-isopropylpiperazine-1-carboxylate;

1-(5-acetylpyridin-2-yl)piperidin-4-yl 4-isopropylpiperazine-1-carboxylate;

1-(5-carbamoylpyridin-2-yl)piperidin-4-yl 4-isopropyl-1,4-diazepane-1-carboxylate;

1-(5-(hydroxymethyl)pyridin-2-yl)piperidin-4-yl 4-isopropylpiperazine-1-carboxylate;

1-(pyridin-2-yl)piperidin-4-yl 4-cyclobutylpiperazine-1-carboxylate;

1-(3-fluoropyridin-2-yl)piperidin-4-yl 4-isopropylpiperazine-1-carboxylate;

1-(3-(trifluoromethyl)pyridin-2-yl)piperidin-4-yl 4-isopropylpiperazine-1-carboxylate;

1-(3-(trifluoromethyl)pyridin-2-yl)piperidin-4-yl 4-cyclobutylpiperazine-1-carboxylate;

1-(3-cyanopyridin-2-yl)piperidin-4-yl 4-cyclobutylpiperazine-1-carboxylate;

1-(3-(methoxycarbonyl)pyridin-2-yl)piperidin-4-yl 4-isopropylpiperazine-1-carboxylate;

1-(4-fluoropyridin-2-yl)piperidin-4-yl 4-isopropylpiperazine-1-carboxylate;

1-(4-cyanopyridin-2-yl)piperidin-4-yl 4-isopropylpiperazine-1-carboxylate;

1-(4-(trifluoromethyl)pyridin-2-yl)piperidin-4-yl 4-isopropylpiperazine-1-carboxylate;

1-(4-(methoxycarbonyl)pyridin-2-yl)piperidin-4-yl 4-isopropylpiperazine-1-carboxylate;

1-(4-(methoxycarbonyl)pyridin-2-yl)piperidin-4-yl 4-cyclobutylpiperazine-1-carboxylate;

1-(4-methoxypyridin-2-yl)piperidin-4-yl 4-isopropylpiperazine-1-carboxylate;

1-(4-(methoxymethyl)pyridin-2-yl)piperidin-4-yl 4-isopropylpiperazine-1-carboxylate;

1-(4-(hydroxymethyl)pyridin-2-yl)piperidin-4-yl 4-isopropylpiperazine-1-carboxylate;

1-(5-fluoropyridin-2-yl)piperidin-4-yl 4-cyclobutylpiperazine-1-carboxylate;
1-(5-(methoxycarbonyl)pyridin-2-yl)piperidin-4-yl 4-cyclobutylpiperazine-1-carboxylate;
1-(5-methoxypyridin-2-yl)piperidin-4-yl 4-cyclopropylpiperazine-1-carboxylate;
1-(5-methoxypyridin-2-yl)piperidin-4-yl 4-ethylpiperazine-1-carboxylate;
1-(5-methoxypyridin-2-yl)piperidin-4-yl 4-isopropylpiperazine-1-carboxylate;
1-(5-methoxypyridin-2-yl)piperidin-4-yl 4-cyclobutylpiperazine-1-carboxylate;
6-(4-(4-isopropylpiperazine-1-carbonyloxy)piperidin-1-yl)nicotinic acid;
1-(5-acetylpyridin-2-yl)piperidin-4-yl 4-cyclobutylpiperazine-1-carboxylate;
1-(5-(cyclobutylcarbamoyl)pyridin-2-yl)piperidin-4-yl 4-isopropylpiperazine-1-carboxylate;
1-(5-(2-hydroxypropan-2-yl)pyridin-2-yl)piperidin-4-yl 4-isopropylpiperazine-1-carboxylate;
1-(5-(2-oxopyrrolidin-1-yl)pyridin-2-yl)piperidin-4-yl 4-cyclobutylpiperazine-1-carboxylate;
1-(5-(2-oxopyrrolidin-1-yl)pyridin-2-yl)piperidin-4-yl 4-isopropylpiperazine-1-carboxylate;
1-(5-carbamoylpyridin-2-yl)piperidin-4-yl 4-(1-hydroxypropan-2-yl)piperazine-1-carboxylate;
(R)-1-(5-carbamoylpyridin-2-yl)piperidin-4-yl 4-(1-hydroxypropan-2-yl)piperazine-1-carboxylate;
(S)-1-(5-carbamoylpyridin-2-yl)piperidin-4-yl 4-(1-hydroxypropan-2-yl)piperazine-1-carboxylate;
1-(5-carbamoylpyridin-2-yl)piperidin-4-yl 4-(1-methoxypropan-2-yl)piperazine-1-carboxylate;
(R)-1-(5-carbamoylpyridin-2-yl)piperidin-4-yl 4-(1-methoxypropan-2-yl)piperazine-1-carboxylate;
(S)-1-(5-carbamoylpyridin-2-yl)piperidin-4-yl 4-(1-methoxypropan-2-yl)piperazine-1-carboxylate;
1-(5-carbamoylpyridin-2-yl)piperidin-4-yl 4-(2-hydroxyethyl)piperazine-1-carboxylate;
1-(5-(thiazol-2-yl)pyridin-2-yl)piperidin-4-yl 4-isopropylpiperazine-1-carboxylate;
1-(6-(trifluoromethyl)pyridin-2-yl)piperidin-4-yl 4-isopropylpiperazine-1-carboxylate;
1-(6-cyanopyridin-2-yl)piperidin-4-yl 4-cyclobutylpiperazine-1-carboxylate;
1-(6-(methoxycarbonyl)pyridin-2-yl)piperidin-4-yl 4-isopropylpiperazine-1-carboxylate;
1-(6-(methoxycarbonyl)pyridin-2-yl)piperidin-4-yl 4-cyclobutylpiperazine-1-carboxylate;
1-(6-(methoxymethyl)pyridin-2-yl)piperidin-4-yl 4-isopropylpiperazine-1-carboxylate;
1-(6-(methoxymethyl)pyridin-2-yl)piperidin-4-yl 4-cyclobutylpiperazine-1-carboxylate;
1-(6-(hydroxymethyl)pyridin-2-yl)piperidin-4-yl 4-isopropylpiperazine-1-carboxylate;
1-(6-methoxypyridin-2-yl)piperidin-4-yl 4-isopropylpiperazine-1-carboxylate;
1-(6-cyanopyridin-2-yl)piperidin-4-yl 4-isopropylpiperazine-1-carboxylate;
1-(6-carbamoylpyridin-3-yl)piperidin-4-yl 4-isopropylpiperazine-1-carboxylate;
1-(6-(methoxycarbonyl)pyridin-3-yl)piperidin-4-yl 4-isopropylpiperazine-1-carboxylate;
1-(6-(methoxycarbonyl)pyridin-3-yl)piperidin-4-yl 4-cyclobutylpiperazine-1-carboxylate;
1-(6-(hydroxymethyl)pyridin-3-yl)piperidin-4-yl 4-isopropylpiperazine-1-carboxylate;
1-(6-(hydroxymethyl)pyridin-3-yl)piperidin-4-yl 4-cyclobutylpiperazine-1-carboxylate;
1-(6-(methoxymethyl)pyridin-3-yl)piperidin-4-yl 4-cyclobutylpiperazine-1-carboxylate;
1-(6-(methoxymethyl)pyridin-3-yl)piperidin-4-yl 4-isopropylpiperazine-1-carboxylate;
1-(6-carbamoylpyridin-3-yl)piperidin-4-yl 4-cyclobutylpiperazine-1-carboxylate;
1-(pyridin-4-yl)piperidin-4-yl 4-isopropylpiperazine-1-carboxylate;
1-(pyridin-4-yl)piperidin-4-yl 4-cyclobutylpiperazine-1-carboxylate;
1-(6-methoxypyridazin-3-yl)piperidin-4-yl 4-isopropylpiperazine-1-carboxylate;
1-(6-methoxypyridazin-3-yl)piperidin-4-yl 4-cyclobutylpiperazine-1-carboxylate;
1-(6-methoxypyrazin-2-yl)piperidin-4-yl 4-isopropylpiperazine-1-carboxylate;
1-(6-methoxypyrazin-2-yl)piperidin-4-yl 4-cyclobutylpiperazine-1-carboxylate;
1-(imidazo[1,2-a]pyridin-7-yl)piperidin-4-yl 4-isopropylpiperazine-1-carboxylate;
1-(imidazo[1,2-a]pyridin-7-yl)piperidin-4-yl 4-cyclobutylpiperazine-1-carboxylate;
1-(2-methylimidazo[1,2-a]pyridin-7-yl)piperidin-4-yl 4-isopropylpiperazine-1-carboxylate;
1-(4-carbamoylphenyl)piperidin-4-yl 4-cyclobutylpiperazine-1-carboxylate;
1-(thiazol-4-yl)piperidin-4-yl 4-isopropylpiperazine-1-carboxylate;
1-(thiazol-5-yl)piperidin-4-yl 4-isopropylpiperazine-1-carboxylate;
1-(thiazol-5-yl)piperidin-4-yl 4-cyclobutylpiperazine-1-carboxylate;
1-(thiazol-2-yl)piperidin-4-yl 4-isopropylpiperazine-1-carboxylate;
1-(5-methylthiazol-2-yl)piperidin-4-yl 4-isopropylpiperazine-1-carboxylate;
methyl 2-(4-(4-isopropylpiperazine-1-carbonyloxy)piperidin-1-yl)thiazole-5-carboxylate;
methyl 2-(4-(4-cyclobutylpiperazine-1-carbonyloxy)piperidin-1-yl)thiazole-5-carboxylate;
1-(5-carbamoylthiazol-2-yl)piperidin-4-yl 4-isopropylpiperazine-1-carboxylate;
1-(5-(hydroxymethyl)thiazol-2-yl)piperidin-4-yl 4-isopropylpiperazine-1-carboxylate;
1-(4-methylthiazol-2-yl)piperidin-4-yl 4-isopropylpiperazine-1-carboxylate;
1-(4-methylthiazol-2-yl)piperidin-4-yl 4-cyclobutylpiperazine-1-carboxylate;
methyl 2-(4-(4-isopropylpiperazine-1-carbonyloxy)piperidin-1-yl)thiazole-4-carboxylate;
1-(4-(hydroxymethyl)thiazol-2-yl)piperidin-4-yl 4-isopropylpiperazine-1-carboxylate;
1-(4-carbamoylthiazol-2-yl)piperidin-4-yl 4-isopropylpiperazine-1-carboxylate;
methyl 2-(4-(4-cyclobutylpiperazine-1-carbonyloxy)piperidin-1-yl)thiazole-4-carboxylate;
1-(1,3,4-thiadiazol-2-yl)piperidin-4-yl 4-isopropylpiperazine-1-carboxylate;
1-(1,3,4-thiadiazol-2-yl)piperidin-4-yl 4-cyclobutylpiperazine-1-carboxylate;
1-(5-methyl-1,3,4-thiadiazol-2-yl)piperidin-4-yl 4-isopropylpiperazine-1-carboxylate;
1-(5-morpholino-1,3,4-thiadiazol-2-yl)piperidin-4-yl 4-cyclobutylpiperazine-1-carboxylate;

1-(5-morpholino-1,3,4-thiadiazol-2-yl)piperidin-4-yl 4-isopropylpiperazine-1-carboxylate;
1-(5-carbamoylpyridin-2-yl)pyrrolidin-3-yl 4-isopropylpiperazine-1-carboxylate;
(R)-1-(5-carbamoylpyridin-2-yl)pyrrolidin-3-yl 4-isopropylpiperazine-1-carboxylate;
(S)-1-(5-carbamoylpyridin-2-yl)pyrrolidin-3-yl 4-isopropylpiperazine-1-carboxylate;
1-(5-(trifluoromethyl)pyridin-2-yl)pyrrolidin-3-yl 4-isopropylpiperazine-1-carboxylate;
(R)-1-(5-(trifluoromethyl)pyridin-2-yl)pyrrolidin-3-yl 4-isopropylpiperazine-1-carboxylate;
(S)-1-(5-(trifluoromethyl)pyridin-2-yl)pyrrolidin-3-yl 4-isopropylpiperazine-1-carboxylate;
1-(5-cyanopyridin-2-yl)pyrrolidin-3-yl 4-isopropylpiperazine-1-carboxylate;
(R)-1-(5-cyanopyridin-2-yl)pyrrolidin-3-yl 4-isopropylpiperazine-1-carboxylate;
(S)-1-(5-cyanopyridin-2-yl)pyrrolidin-3-yl 4-isopropylpiperazine-1-carboxylate;
1-(6-carbamoylpyridin-3-yl)pyrrolidin-3-yl 4-isopropylpiperazine-1-carboxylate;
(R)-1-(6-carbamoylpyridin-3-yl)pyrrolidin-3-yl 4-isopropylpiperazine-1-carboxylate;
(S)-1-(6-carbamoylpyridin-3-yl)pyrrolidin-3-yl 4-isopropylpiperazine-1-carboxylate;
1-(5-carbamoylpyridin-2-yl)azetidin-3-yl 4-isopropylpiperazine-1-carboxylate;
1-(5-cyanopyridin-2-yl)azetidin-3-yl 4-isopropylpiperazine-1-carboxylate; and
1-(5-(trifluoromethyl)pyridin-2-yl)azetidin-3-yl 4-isopropylpiperazine-1-carboxylate;
or salts of these compounds.

8. A pharmaceutical composition comprising a therapeutically effective amount of a compound according to claim 1 and one or more pharmaceutically acceptable carriers.

9. A combination comprising a therapeutically effective amount of the compound according to claim 1 and one or more therapeutically active agents.

10. A compound of formula II-1

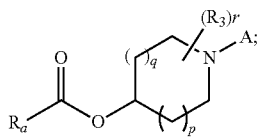

or a salt thereof; in which
p is 1 and q is 1;
p is 0 and q is 1; or
p is 0 and q is 0;
r is 0, 1, 2, 3 or 4;
each $R_3$ independently is halogen, hydroxyl, amino, cyano, nitro, $C_{1-6}$alkyl, $C_{1-6}$halogenalkyl, $C_{1-6}$hydroxyalkyl, $C_{1-4}$alkoxy-$C_{1-6}$alkyl, amino-$C_{1-6}$ alkyl, $C_{1-4}$alkyl-amino-$C_{1-6}$alkyl, di($C_{1-4}$alkyl)-amino-$C_{1-6}$alkyl, $C_{1-6}$alkoxy, $C_{1-6}$halogenalkoxy, $C_{1-6}$alkylamino, di($C_{1-6}$ alkyl)amino, $C_{2-6}$alkenyl, $C_{2-6}$halogenalkenyl, $C_{2-6}$alkinyl or $C_{2-6}$halogenalkinyl;
or $C_{3-6}$cycloalkyl, wherein one carbon atom may be replaced by an oxygen atom, wherein the $C_{3-6}$cycloalkyl may be attached directly to the methylene or via a $C_{1-2}$alkylene, and wherein the $C_{3-6}$cycloalkyl may be substituted once or more than once by halogen;
or two $R_3$ at the same carbon atom form together with said carbon atom a $C_{3-6}$cycloalkyl;
$R_a$ is a leaving group selected from halogen or a group selected from

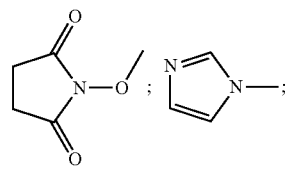

A is a five- to six-membered monocyclic aromatic ring system, wherein said ring system may contain from 1 to 3 hetero atoms selected from nitrogen, oxygen and sulfur, and wherein said ring system may be substituted once or more than once by $R_5$; wherein each $R_5$ independently is halogen; cyano; —C(O)NH$_2$; or —X$_2$—R$_6$; X$_2$ is selected from bond; carbonyl; oxygen; —C(O)—NH—; and —C(O)—O—; and R$_6$ is $C_{1-6}$alkyl; $C_{1-6}$halogenalkyl; or $C_{1-4}$alkoxy-$C_{1-6}$alkyl.

11. A method of ameliorating obesity comprising administration of an effective amount of a compound according to claim 1 to a subject in need of treatment thereof.

12. A method of ameliorating epilepsy comprising administration of an effective amount of a compound according to claim 1 to a subject in need of treatment thereof.

13. A method of ameliorating narcolepsy comprising administration of an effective amount of a compound according to claim 1 to a subject in need of treatment thereof.

14. A method for ameliorating narcolepsy in a subject in need of treatment thereof comprising administration of an effective amount of a compound according to claim 1 in combination with another active agent selected from the group consisting of: a noradrenaline-dopamine reuptake inhibitor, a tri- or tetracyclic antidepressant, a serotonin-noradrenaline reuptake inhibitor, a selective serotonin reuptake inhibitor, a noradrenaline reuptake inhibitor, a MAO-B inhibitor, a gamma-hydroxy-butyrate and a psychostimulant.

15. The method according to claim 14 wherein the other active agent is selected from the group consisting of: modafinil, armodafinil, clomipramine, venlafaxine, duloxetine, paroxetine, reboxetine, atomoxetine, selegiline and methylphenidate.

* * * * *